(12) United States Patent
McEntire et al.

(10) Patent No.: US 9,925,295 B2
(45) Date of Patent: Mar. 27, 2018

(54) CERAMIC AND/OR GLASS MATERIALS AND RELATED METHODS

(71) Applicant: Amedica Corporation, Salt Lake City, UT (US)

(72) Inventors: Bryan J. McEntire, Sandy, UT (US); Ryan M. Bock, Salt Lake City, UT (US); Giuseppe Pezzotti, Kyoto (JP)

(73) Assignee: Amedica Corporation, Salt Lake City, UT (US)

( * ) Notice: Subject to any disclaimer, the term of this patent is extended or adjusted under 35 U.S.C. 154(b) by 0 days.

(21) Appl. No.: 15/230,305

(22) Filed: Aug. 5, 2016

(65) Prior Publication Data

US 2016/0339144 A1    Nov. 24, 2016

Related U.S. Application Data

(63) Continuation-in-part of application No. 13/890,880, filed on May 9, 2013.
(Continued)

(51) Int. Cl.
*A61L 27/02* (2006.01)
*C23C 16/56* (2006.01)
(Continued)

(52) U.S. Cl.
CPC .......... *A61L 27/025* (2013.01); *A61L 27/10* (2013.01); *A61L 27/306* (2013.01);
(Continued)

(58) Field of Classification Search
CPC .............. B32B 3/00; A61F 2/28; C04B 35/58
(Continued)

(56) References Cited

U.S. PATENT DOCUMENTS

| 4,327,187 A | 4/1982 | Komatsu et al. |
| 4,451,302 A | 5/1984 | Prescott et al. |

(Continued)

FOREIGN PATENT DOCUMENTS

| JP | H02-17062 A | 1/1990 |
| WO | 2012/018264 | 2/2012 |

(Continued)

OTHER PUBLICATIONS

International Search Report for PCT/US2016/045927, dated Oct. 7, 2016, 2 pgs.
(Continued)

*Primary Examiner* — Dah-Wei D Yuan
*Assistant Examiner* — Andrew Bowman
(74) *Attorney, Agent, or Firm* — Polsinelli PC; Ari M. Bai

(57) ABSTRACT

Methods for improving the antibacterial, osteoconductive, and/or osteoinductive characteristics of silicon nitride and/or other ceramic materials, particularly to make them more suitable for use in manufacturing biomedical implants. In some embodiments and implementations, the surface chemistry and/or morphology of a silicon nitride bioceramic may be modulated significantly through thermal, chemical, and/or mechanical treatments to achieve such advantageous results. A portion of the resulting material, such as a glaze or upper layer of the material, may be separately produced as a powder or frit, for example, and used in manufacturing biomedical implants and/or other products, such as by using such portion of the material as a coating or filler. In other embodiments the surface material may be separately manufactured as a silicon oxynitride monolith.

4 Claims, 23 Drawing Sheets

Related U.S. Application Data

(60) Provisional application No. 61/644,906, filed on May 9, 2012, provisional application No. 62/202,687, filed on Aug. 7, 2015, provisional application No. 62/331,177, filed on May 3, 2016.

(51) Int. Cl.

| | |
|---|---|
| *C04B 35/597* | (2006.01) |
| *A61L 27/54* | (2006.01) |
| *A61L 27/10* | (2006.01) |
| *A61L 27/30* | (2006.01) |
| *A61L 27/50* | (2006.01) |
| *A61L 27/44* | (2006.01) |

(52) U.S. Cl.
CPC ............ *A61L 27/446* (2013.01); *A61L 27/50* (2013.01); *A61L 27/54* (2013.01); *C04B 35/597* (2013.01); *C23C 16/56* (2013.01); *A61L 2400/18* (2013.01); *A61L 2430/02* (2013.01); *A61L 2430/12* (2013.01); *C04B 2235/3873* (2013.01)

(58) Field of Classification Search
USPC .......................... 623/16.11; 216/108; 501/98
See application file for complete search history.

(56) References Cited

U.S. PATENT DOCUMENTS

| | | | |
|---|---|---|---|
| 4,476,590 A | | 10/1984 | Scales et al. |
| 4,506,021 A | * | 3/1985 | Jack ...................... C04B 35/597 264/665 |
| 4,640,903 A | | 2/1987 | Matsuhiro et al. |
| 4,775,548 A | | 10/1988 | Lankford, Jr. |
| 4,962,065 A | | 10/1990 | Brown et al. |
| 5,062,798 A | | 11/1991 | Tsuge et al. |
| 6,150,282 A | | 11/2000 | Rath et al. |
| 6,302,913 B1 | | 10/2001 | Ripamonti et al. |
| 6,582,715 B1 | | 6/2003 | Barry et al. |
| 6,756,160 B2 | | 6/2004 | Carcia |
| 6,790,233 B2 | | 9/2004 | Brodke et al. |
| 6,846,327 B2 | | 1/2005 | Khandkar et al. |
| 6,881,229 B2 | | 4/2005 | Khandkar et al. |
| 6,994,727 B2 | | 2/2006 | Khandkar et al. |
| 7,211,271 B2 | | 5/2007 | Risbud et al. |
| 7,666,229 B2 | | 2/2010 | Khandkar |
| 7,695,521 B2 | | 4/2010 | Ely et al. |
| 7,758,646 B2 | | 7/2010 | Khandkar et al. |
| 7,771,481 B2 | | 8/2010 | Khandkar et al. |
| 7,776,085 B2 | | 8/2010 | Bernero et al. |
| 7,780,738 B2 | | 8/2010 | Khandkar et al. |
| 7,906,132 B2 | | 3/2011 | Ziegler et al. |
| 8,016,890 B2 | | 9/2011 | Khandkar et al. |
| 8,067,403 B2 | | 11/2011 | Whiteford et al. |
| 8,105,086 B2 | | 1/2012 | Asgary |
| 8,123,812 B2 | | 2/2012 | Khandkar |
| 8,124,016 B2 | | 2/2012 | Lee et al. |
| 8,133,284 B2 | | 3/2012 | Ely et al. |
| 2002/0173850 A1 | | 11/2002 | Brodke et al. |
| 2003/0019843 A1 | * | 1/2003 | Kawai ................... C04B 35/111 216/108 |
| 2003/0029839 A1 | | 2/2003 | Chou |
| 2003/0153984 A1 | | 8/2003 | Khandkar et al. |
| 2004/0133281 A1 | | 7/2004 | Khandkar et al. |
| 2005/0049706 A1 | | 3/2005 | Brodke et al. |
| 2005/0079200 A1 | | 4/2005 | Rathenow |
| 2005/0107888 A1 | | 5/2005 | Khandkar et al. |
| 2005/0240273 A1 | | 10/2005 | Khandkar et al. |
| 2005/0273176 A1 | | 12/2005 | Ely et al. |
| 2006/0052875 A1 | | 3/2006 | Bernero et al. |
| 2006/0161256 A1 | | 7/2006 | Ziegler et al. |
| 2006/0276788 A1 | | 12/2006 | Berry et al. |
| 2007/0125247 A1 | | 6/2007 | Kunstmann |
| 2007/0191952 A1 | | 8/2007 | Bernero |
| 2007/0198093 A1 | | 8/2007 | Brodke et al. |
| 2008/0033563 A1 | | 2/2008 | Khandkar et al. |
| 2008/0281429 A1 | | 11/2008 | Pawar et al. |
| 2009/0093881 A1 | | 4/2009 | Bandyopadhyay et al. |
| 2010/0049331 A1 | | 2/2010 | Khandkar |
| 2010/0174383 A1 | | 7/2010 | Pawar et al. |
| 2010/0215643 A1 | | 8/2010 | Clevenger et al. |
| 2010/0228354 A1 | | 9/2010 | Ely et al. |
| 2010/0256758 A1 | * | 10/2010 | Gordon ..................... A61F 2/28 623/16.11 |
| 2011/0008407 A1 | | 1/2011 | Gan et al. |
| 2011/0046741 A1 | | 2/2011 | Khandkar et al. |
| 2011/0098818 A1 | | 4/2011 | Brodke et al. |
| 2011/0143127 A1 | | 6/2011 | Gupta et al. |
| 2012/0190114 A1 | | 7/2012 | Moon |
| 2013/0030531 A1 | | 1/2013 | Brodke et al. |
| 2013/0302509 A1 | | 11/2013 | McEntire et al. |
| 2016/0067387 A1 | | 3/2016 | Varanasi et al. |

FOREIGN PATENT DOCUMENTS

| | | |
|---|---|---|
| WO | 2013/030787 | 3/2013 |
| WO | 2013/170059 | 11/2013 |

OTHER PUBLICATIONS

Written Opinion for PCT/US2016/045927, dated Oct. 7, 2016, 4 pgs.

Ilyas et al., Enhanced Interfacial Adhesion and Osteogenesis for Rapid "Bone-like" 1-19 Biomineralization by PECVD-Based Silicon Oxynitride Overlays, ACS Applied Materials & Interfaces, vol. 7, No. 28, Jun. 22, 2015.

Zhang, et al. "Osteoblast Differentiation and Disinfection Induced by Nitrogen Plasma-Trea Ted Surfaces" Bio-Medical Materials and Engineering IOS Press, Amsterdam, NL, vol. 21 No. 2, Jan. 1, 2011 pp. 75-82.

European Search Report for 13788340.1, dated Dec. 8, 2015, 6 pgs.

Anderson et al., Bone Ingrowth Into Porous Silicon Nitiride, May 2009, Journal of Biomedical Materials Research Part A, pp. 1598-1605.

Vasilev, K., Cook, J., & Griesser, H. J. (2009). Antibacterial surfaces for biomedical devices. Expert review of medical devices, 6(5), 553-67.

Vasilev, K., Griesser, S. S., & Griesser, H. J. (2011 ). Antibacterial Surfaces and Coatings Produced by Plasma Techniques. Plasma Processes and Polymers, 8(11 ), 1010-1023.

I. Pawasarat, et al., "Total Joint Arthroplasty Infections Caused by Antibiotic-Resistant Strains: The Economic Perspective," AAOS Poster 196, (2010).

Okada, K., Fukuyama, K., & Kameshima, Y. (1995). Characterization of Surface-Oxidized Phase in Silicon Nitride and Silicon Oxynitride Powders by X-ray Photoelectron Spectroscopy. Journal of the American Ceramic Society, 78(8), 2021-2026.

Zhmud B. Sonnefeld, J. & Bergstrom, L. (1999). Influence of chemical pretreatment on the surface properties of silicon nitride powder. Colloids and Surfaces, 158, 327-341.

Bergstrom et al. (1990). Surface Chemistry of Silicon Nitride Powders: Electrokinetic Behavior and ESCA Studies. Colloids and Surfaces, 49, 183-197.

Cerovic, L. S., Milonjic, S. K., Bahloui-Hourlier, D., & Doucey, B. (2002). Surface Properties of Silicon Nitride Powders. Collids and Surfaces, 197, 147-156.

Mezzasalma, S. (1996). Characterization of Silicon Nitride Surface in Water and Acid Environment: A General Approach to the Colloidal Suspensions. Journal of Colloid and Interface Science, 180{2), 413-420. doi:1 0.1006/icis.1996.0320.

Greil, P., Nitzsche, R., & Friedrich, H. (1991 ). Evaluation of oxygen content on silicon nitride powder surface from the measurement of the isoelectric point. Journal of the European Ceramic Society, 7(6), 353-359.

Hackley, V., Wang, P., & Malgham, S. (1993). Effects of soxhlet extraction nitride powders on the surface oxide layer of silicon. Materials Chemistry and Physics, 36, 112-118.

(56) References Cited

OTHER PUBLICATIONS

Mazzocchi, M., & Bell Os I, A (2008). On the possibility of silicon nitride as a ceramic for structural orthopaedic implants. Part 1: processing, microstructure, mechanical properties, cy1otoxicity. Journal of materials science. Materials in medicine, 19(8), 2881-7.

Mazzocchi. M . . . Gardin I, D., Traverso, P. L., Faga, M.G., & Bellosi, A. (2008). On the possibility of silicon nitride as a ceramix for structural orthopaedic implants. Part II: chemical stability and wear resistance in body environment. Journal of materials science. Materials in medicine, 19(8), 2889-901.

Laarz, E., Meurk, A., Yanez, J. A., & Bergstro, L. (2001 ). Silicon Nitride Colloidal Probe Measurements: Interparticle Forces and the Role of Surface-Segment Interactions in Poly (acrylic acid) Adsorption from Aqueous Solution, 82, 1675-1682.

Odriozola, J. A (1997). Surface characterization of nitrides and oxynitrides of groups IIIA and IVA. Journal of the European Ceramic Society, 17(15-16), 1989-1999.

Ikeda, T., Hirayama, H., Yamaguchi, H., Tazuke, S., & Watanabe, M. (1986). Polycationic biocides with pendant active groups: molecular weight dependence of Polycationic Biocides with Pendant Active Groups: Molecular Weight Dependence of Antibacterial Activity. Antimicrobial Agents and Chemotherapy, 30(1), 132-136.

Montanaro, L., Campoccia, D., & Arc Iola, C. R. (2008). Nanostructured materials for inhibition of bacterial adhesion in orthopedic implants: a minireview. The International journal of artificial organs, 31 (9), 771-6.

Katsikogianni, M.G., & Missirlis, Y. F. (201 0). Interactions of bacteria with specific biomaterial surface chemistries under flow conditions. Acta biomaterialia, 6(3), 1107-18. doi: 10.1 016/j.actbio. 2009.08.006.

Katsikogianni, M.G., & Missirlis, Y. F. (2010). Bacterial adhesion onto materials with specific surface chemistries under flow conditions. Journal of materials science. Materials in medicine, 21 (3), 963-8.

Gristina, A., Shibata, Y., & Giridhar, G. (1994 ). The glycocalyx, biofilm, microbes, and resistant infection. Seminars iin Arthroplasty, 5(4), 160-170.

Lansdown, a B. G. (Apr. 2002). Silver. 1: Its antibacterial properties and mechanism of action. Journal of wound care.

Afanasiev, S. a, Tsapko, L. P., Kurzina, I. a, Chuhlomina, L. N., & Babokin, V. E. (2010). Effect of model biological media of stability of complex of silver nanoparticles applied onto silicon nitride substrate. Bulletin of experimental biology and medicine, 150(1 ), 160-4.

Goodman, S. B., Yao, Z., Keeney, M., & Yang, F. (2013). The future of biologic coatings for orthopaedic implants. Biomaterials, 34(13), 3174-83.

S. J. Peacock. et al. "Bacterial Fibronectin-Binding Proteins and Endothelial Cell Surface Fibronectin Mediate Adherence of *Staphylococcus aureus* to Resting Human Endothelial Cells." Microbiology, 145, 3477-3486, (1999).

S. M. Kuntz, et al., "Infection Burden for Hip and Knee Arthroplasty in the United States," The Journal of Arthroplasty, 23, [7], 984-991 (2008).

Katsikogianni, et al. "Concise Review of Mechanisms of Bacterial Adhesion to Biomaterials and Techniques Used in Estimating Bateria-Materiallnteractions", European Cells and Materials, 8, 37-57 (2004).

International Search Report for PCT/US13/040387, dated Oct. 31, 2013, 2 pgs.

Written Opinion for PCT/US13/040387, dated Oct. 31, 2013, 13 pgs.

Buntz. Used in Space Shuffles, the Next Frontier for Silicon Nitride is Orthopedics. MODI Medical Device and Diagnostic Industry News Products and Suppliers: Orthopedics, Mar. 16, 2012.

Jou, C.-H., Yuan, L., Lin, S., Hwang, M., Chou, W.-L., Yu, D.-G., & Yang, M.-C. (2007). Biocompatibility and antibacterial activity of chitosan and hyaluronic acid immobilized polyester fibers. Journal of Applied Polymer Science, 104, 220-225.

Hamilton, V., Yuan, Y., Rigney, D., Chesnuti, B. , Pucketi, A., Ong, J., Yang, Y., et al. (2007). Bone cell attachment and growth on well-characterized chitosan films. Polymer International, 104(Dec. 2006), 641-647.

Costa-Pinto, A. et al. (2011 ). Scaffolds based bone tissue engineering: the role of chitosan. Tissue Engineering Part B, vol. 17(5).

Choi, H. W., Dauskardt, R. H., Lee, S.-C., Lee, K.-R., & Oh, K. H. (2008). Characteristic of silver doped DLC films on surface properties and protein adsorption. Diamond and Related Materials. 17(3), 252-257.

Knetsch, M. L. W ., & Koole, L. H. (2011 ). New Strategies in the Development of Antimicrobial Coatings: The Example of Increasing Usage of Silver and Silver Nanoparticles. Polymers, 3(1 ). 340-366.

Endrino, J. L., Sanchez-Lopez, J. C., Galindo, R. E., Horwat, D., & Anders, a. (2010). Beneficial silver: antibacterial nanocomposite Ag-DLC coating to reduce osteolysis of orthopaedic implants. Journal of Physics: Conference Series. 252. 012005.

Leckband, D., & Israelachvili, J. (2001 ). Intermolecular forces in biology. Quarterly Reviews of Biophysics (vol. 34, p. 105-267).

Ionescu, V., Lungu, C. P., Osiac, M., & Ciupina, V. (2010). Silver containing carbon amorphous nanocomposite films deposited by termionic vacuum arc technique. Rom. Journ. Phys., 55(1-2), 119-126.

Clement, J. L., & Jarred, P. S. (1994). Antibacterial silver. Metal-based drugs, 1(5-6), 467-82.

Costerton, J. W., Stewart, P. S., & Greenberg, E. P. (1999). Bacterial biofilms: a common cause of persistent infections. Science (New York, N.Y.), 284(5418), 1318-22.

Namavar, F., Jackson, J.D., Sharp, J. G., Mann, E. E., & Bayles, K. E. (2007). Searching for Smart Durable Coatings to Promote Bone Marrow Stromal Cell Growth While Preventing Biofilm Formation. Mater. Res. Soc. Symp. Proc. (vol. 954).

H-L. Huang, et al. Antibacterial TaN—Ag Coatings on Titanium Dental Implants, Surface & Coatings Technology, (2010), doi:1 0.1016/j.surfcoa\.201 0.07.096.

N. E. Epstein, "Preoperative, Intraoperative, and Postoperative Measures to Further Reduce Spinal Infections," Surgical Neurology International, 2:17, (2011 ).

M. A. Olsen, et al. Risk Factors for Surgical Site Infection Following Orthopaedic Spinal Operations, The Journal of Bone and Joint Surgery, 90, [1], 62-69, (2008).

A. Mukherjee, et al. "Antimicrobial Activity of Aluminium Oxide Nanoparticles for Potential Clinical Applications," Foratex, 245-251 (2011 ).

C. P. Avanzato, et al. "Biomimetic Synthesis and Antibacterial Characteristics of Magnesium Oxide-Germanium Dioxide Nanocomposite Powders," J. Composite Materials, vol. 43, No. 8, 897-910, (2009).

M. M. Dowsey, et al., "Infection in Primary Hip and Knee Arthroplasty," Recent Advances in Arthroplasty, ISBN: 378-953-307-990-5,413-438, (2012).

T. F. Moyad, et al., Evaluation and Management of the Infected Total Hip and Knee, Orthopedics, vol. 31, No. 6, 581-590 (Jun. 2008).

W. Y. Matar, et al. "Preventing Infection in Total Joint Arthroplasty," Journal of Bone and Joint Surgery, 92, 36-46, (2010); doi:10.2106/ JBJS.J.01046.

Nakamura et al., Influence of Nitrogen Ion Implantation Energy on the Wear Resistatnce of Silicon Nitride Ceramics with Different Microstructures, Journal of Surface Finishing Society of Japan, vol. 56, No. 12, 2005, pp. 947-950.

U.S. Office Action in U.S. Appl. No. 13/890,876, dated Apr. 12, 2016.

de Lima Monteiro et al., ECS Transactions, 2009, vol. 23 (1 ), pp. 19-27.

Aswath, P.B., et al. (2015) "Enhanced Interfacial Adhesion and Osteogenesis for Rapid 'Bone-like' Biomineralization by PECVD-Based Silicon Oxynitride Overlays" ACS Applied Materials & Interfaces, 7, 15368-15379; doi:10.1021/acsami.5b03319.

Pezzotti G., et al. (2016) "Silicon nitride bioceramics induce chemically driven lysis in Porphyromonas gingivalis" Langmuir, 32 (12), pp. 3024-3035; DOI: 10.1021/acs.langmuir.6b00393.

(56) References Cited

OTHER PUBLICATIONS

Habelitz, S., et al. "Nitrogen-containing Apatite", Journal of European Ceramic Society, vol. 19, Issue 15, Nov. 1999, pp. 2685-2694.
Office Action issued in corresponding Japanese Patent Application No. 2015-511711, dated Feb. 20, 2017, 7 pages.

* cited by examiner

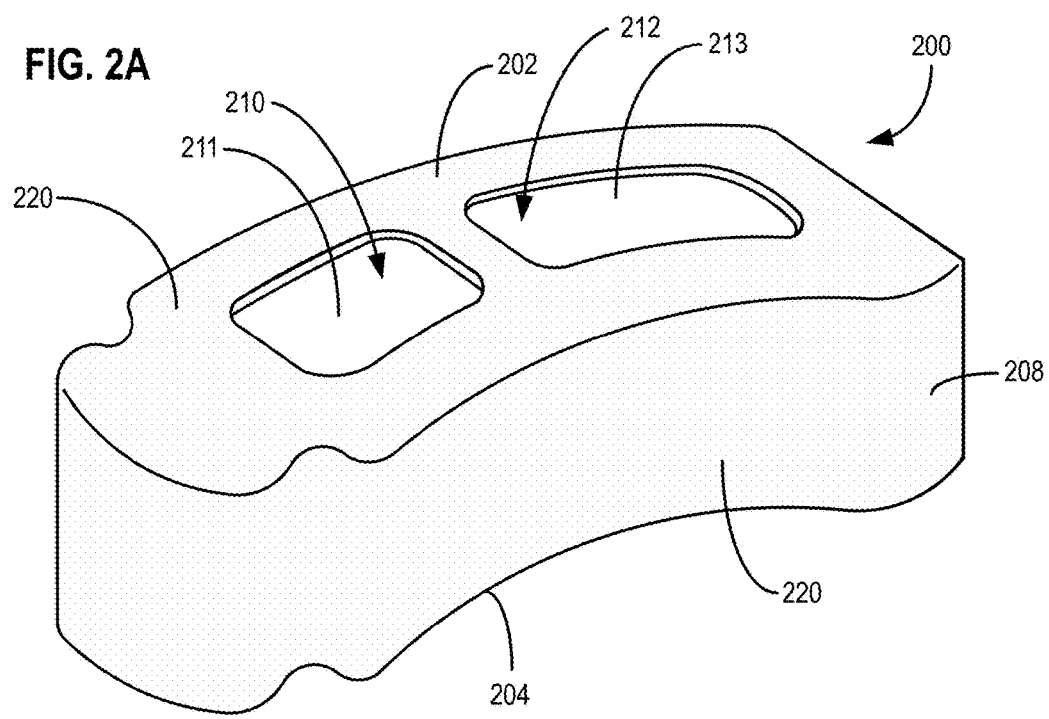
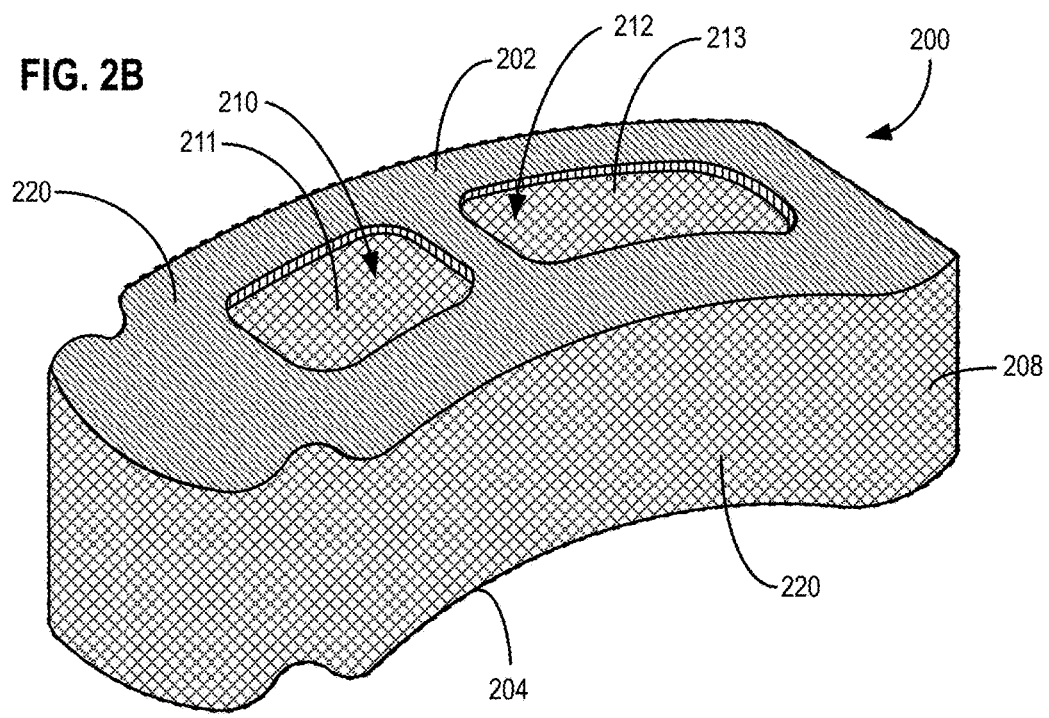

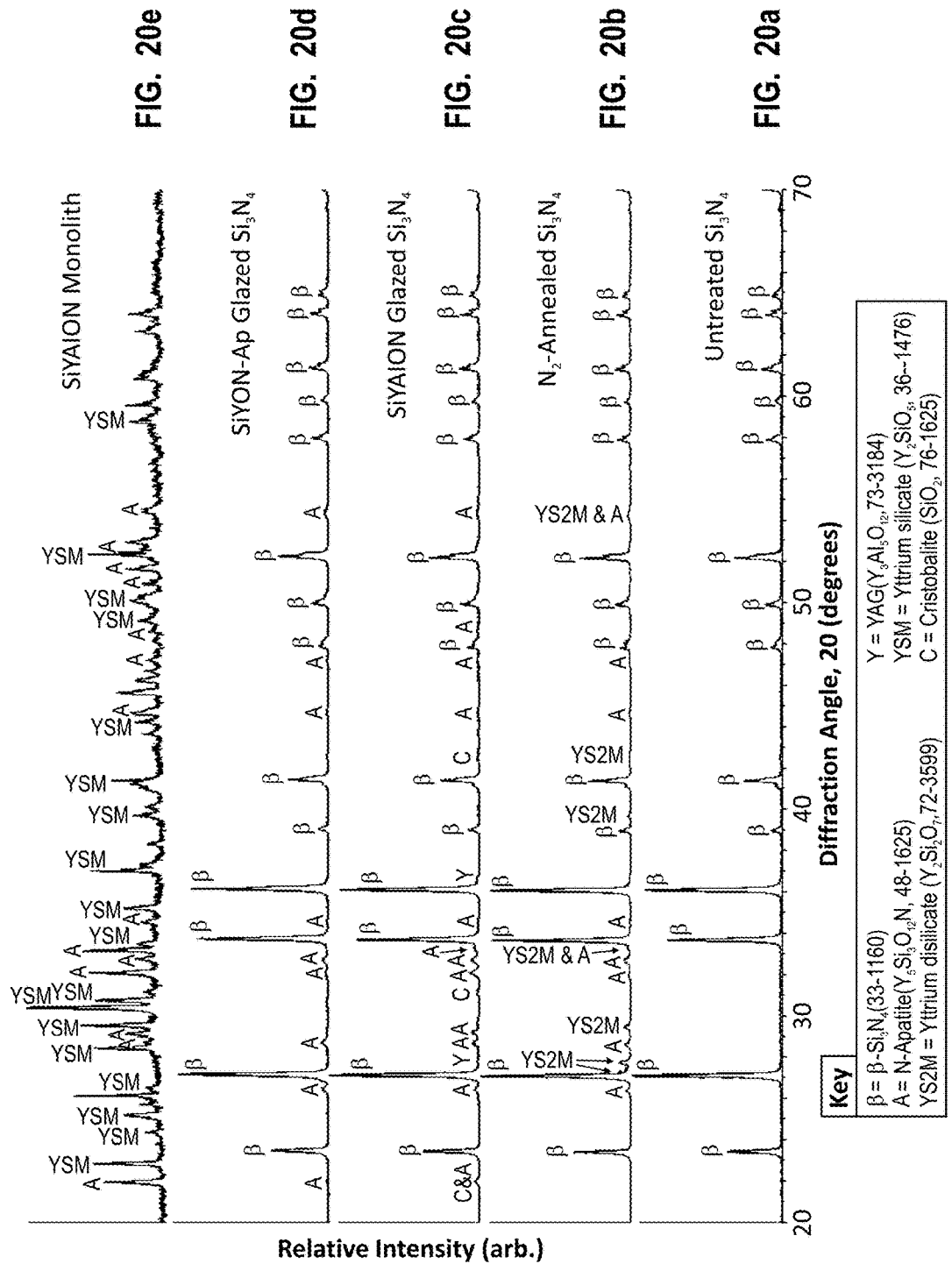

| Element | Surface Elemental Composition (Atomic %) | | |
|---|---|---|---|
| | Untreated $Si_3N_4$ | $N_2$-Annealed | SiYAlON Glazed |
| Si | 38.87% | 36.41% | 28.06% |
| Y | 0.12% | 2.30% | 10.86% |
| Al | 2.34% | 5.66% | 3.38% |
| O | 19.39% | 18.52% | 33.10% |
| N | 39.28% | 37.11% | 24.60% |

FIG. 21

CERAMIC AND/OR GLASS MATERIALS AND RELATED METHODS

RELATED APPLICATIONS

This application is a continuation-in-part of U.S. patent application Ser. No. 13/890,880 filed May 9, 2013, and titled "METHODS FOR ALTERING THE SURFACE CHEMISTRY OF BIOMEDICAL IMPLANTS AND RELATED APPARATUS," which claims the benefit under 35 U.S.C. §119(e) of U.S. Provisional Patent Application No. 61/644,906 filed May 9, 2012 and titled "ANTIBACTERIAL BIOMEDICAL IMPLANTS AND ASSOCIATED MATERIALS, APPARATUS, AND METHODS." This application also claims the benefit under 35 U.S.C. §119(e) of U.S. Provisional Patent Application No. 62/202,687 filed on Aug. 7, 2015 and titled "IMPROVED CERAMIC MATERIALS AND RELATED METHODS" and further claims the benefit under 35 U.S.C. §119(e) of U.S. Provisional Patent Application No. 62/331,177 filed on May 3, 2016 and also titled "IMPROVED CERAMIC MATERIALS AND RELATED METHODS." Each of the aforementioned applications is incorporated herein by reference in its entirety.

SUMMARY

Disclosed herein are embodiments of materials and methods that may be useful for improving certain characteristics of the material for use in biomedical implants. More particularly, certain preferred embodiments and implementations relate to silicon nitride and/or silicon oxynitride materials, and related methods for making such materials, that have improved osteoconductivity and/or antibacterial properties. In some such embodiments and implementations, the material may even possess osteoinductive properties.

In some embodiments and implementations discussed herein, such properties may be provided by, for example, treating a silicon nitride material to draw out and/or force the grain boundary phase or intergranular phase of the material (such as SiYAlON) towards the surface and at least partially coat the material with this amorphous phase, or with multiple amorphous phases, such as SiYAlON, SiYON, and/or SiAlON. Experiments have shown that increased mineralization for bone-like cells, and in some cases even osteoinduction, occurs on such surfaces. Such materials may be used to form biomedical implants with their crystalline phase/base, or the glaze/surface may be removed, crushed, ground and used as, for example, fill material, a matrix, or a coating. Alternatively the entire monolith may be crushed and ground and used in this manner. In other embodiments and implementations, a surface glaze may be applied to a material, such as a silicon nitride material, to mimic the composition of the surface glaze drawn out, as described above. This glaze may be removed from the material and used in various ways described herein or, alternatively, the entire material block including the glaze may be used together, either to form a monolithic implant or ground up and used as previously mentioned.

In a more particular example of a method for improving the osteoconductive characteristics of a silicon nitride material, the method may comprise providing a silicon nitride material block, preparing a glazing slurry, and applying a glaze from the glazing slurry to the silicon nitride material block to obtain a glazed silicon nitride material block. A firing/heat treatment may be performed on the glazed silicon nitride material block to form a finished glaze on the glazed silicon nitride material block.

In some implementations, the finished glaze may comprise at least one of SiYAlON, SiYON, SiAlON, and yttrium aluminum garnet. The finished glaze and/or the glazed silicon nitride material block may comprise both crystalline and amorphous phases.

In some implementations, the glaze may be configured to enhance the osteoconductive properties of the silicon nitride material block. In some such implementations, the glaze may further be configured to provide osteoinductive properties.

In some implementations, the finished glaze may be removed from the silicon nitride material block and used for another purpose. For example, in some implementations, the removed, finished glaze may be ground into a powder and used to manufacture a biomedical implant, such as by incorporating the powder into at least one of a coating, a filler, and a scaffold for the biomedical implant.

In a specific example of a method for incorporation of a silicon oxynitride material having improved osteoconductive characteristics into a biomedical implant, the method may comprise preparing a slurry, which slurry may comprise silicon, oxygen, and nitrogen, and may further comprise at least one of yttrium and aluminum. The slurry may be dried to obtain a dried slurry, after which a heat treatment may be performed on the dried slurry to obtain a silicon oxynitride monolith. In some implementations, the silicon oxynitride monolith may comprise at least one crystalline phase and at least one amorphous phase. The silicon oxynitride monolith material may be incorporated into at least one of a coating, a filler, and a scaffold for a biomedical implant.

In some implementations, the step of performing a heat treatment may comprise performing the heat treatment in a vessel having a chemical makeup configured to mimic the makeup of the slurry, such as a silicon nitride ceramic material.

In some implementations, the step of performing a heat treatment may comprise performing the heat treatment in a gas comprising nitrogen. In some such implementations, the gas may comprise at least essentially 100% nitrogen gas.

In some implementations, the silicon oxynitride monolith may be configured so as to have osteoinductive properties.

In some implementations, the step of incorporating the silicon oxynitride monolith material into at least one of a coating, a filler, and a scaffold for a biomedical implant may comprise using the silicon oxynitride monolith material as a filler in a polymeric material and using the polymeric material to manufacture a biomedical implant, such as a PEEK intervertebral spacer, for example.

In a specific example of a silicon oxynitride material having osteoinductive properties according to some embodiments, the material may comprise a first crystalline phase and a first amorphous phase. In some embodiments, the silicon oxynitride material may have osteoconductive and/or osteoinductive properties.

In some embodiments, the silicon oxynitride material may comprise a surface glaze. In some such embodiments, the surface glaze may comprise the first amorphous phase.

In some embodiments, the first crystalline phase may comprise at least one of SiYAlON, SiYON, SiAlON, or yttrium aluminum garnet, such as N-apatite, yttrium silicate, yttrium disilicate, and/or yttrium aluminum garnet.

Similarly, the first crystalline phase may comprise at least one of SiYAlON, SiYON, SiAlON, and yttrium aluminum garnet.

The features, structures, steps, or characteristics disclosed herein in connection with one embodiment may be combined in any suitable manner in one or more alternative embodiments.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2A is a perspective view of another embodiment of a spinal implant having a coating applied thereto;

FIG. 2B is a perspective view of the embodiment of FIG. 2A after a surface roughening process has been applied to the coating of the implant;

FIGS. 20a-20e depict x-ray diffraction patterns for various materials produced in accordance with methods disclosed herein compared to a control sample;

FIG. 21 is a chart noting the surface atomic composition, as measured by x-ray photoelectron spectroscopy (XPS), of untreated silicon nitride, silicon nitride annealed in nitrogen at about 1400° C. for 30 minutes, and SiYAlON-glazed silicon nitride, respectively;

DETAILED DESCRIPTION

Figure 1A:
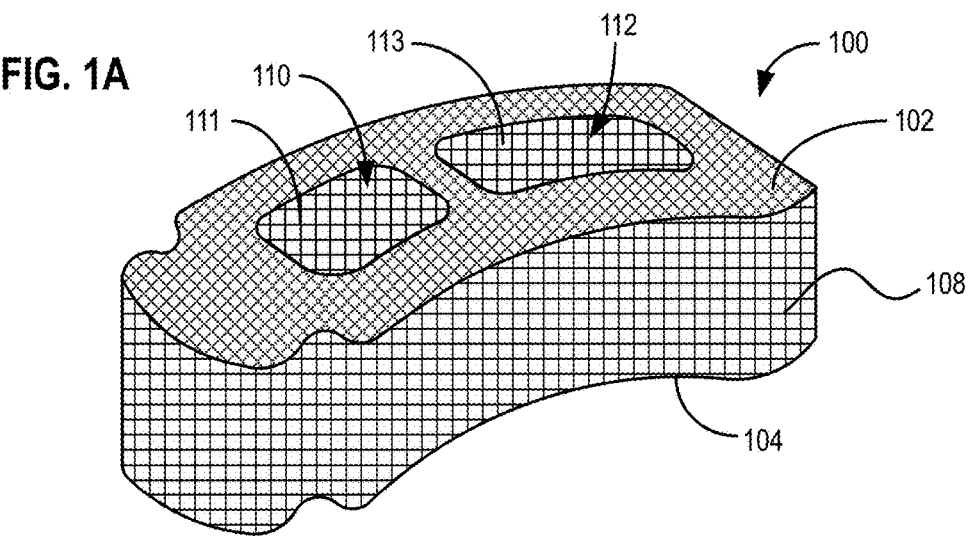
FIG. 1A is a perspective view of one embodiment of a spinal implant.

Embodiments described herein may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail.

Various embodiments of apparatus, methods, and systems are disclosed herein that relate to materials and methods involving ceramic materials, such as silicon nitride ceramic materials. Such materials may be useful in, for example, manufacturing biomedical implants, such as intervertebral spacers or other spinal implants, orthopedic screws, plates, wires, or other fixation devices, articulation implants in the spine, hip, knee, shoulder, ankle or phalanges, catheters, implants for facial or other reconstructive plastic surgery, dental implants, and the like. In some embodiments and implementations, such materials may be used as a coating, particulate within a coating or other material, filler, or otherwise incorporated as filler and/or as a matrix into another material rather than using the improved material as a monolithic material for an implant or other device. The materials and/or methods disclosed herein may provide for one or more improved characteristics that may be particularly useful in connection with such biomedical implants.

For example, in certain preferred embodiments and implementations, the osteoconductive characteristics of the material may be improved and/or the antibacterial function and/or characteristics of the material may be improved. In some embodiments and implementations, this may be accomplished by altering the surface chemistry of the material and/or a coating of the material. In some such embodiments and implementations, this may be accomplished by altering the composition of a transitional oxide surface layer, which may be presented in, most notably, monolithic silicon nitride and silicon nitride coatings.

In some embodiments and/or implementations, improved materials may be created that provide for not only osteoconductivity, but osteoinductivity, which heretofore has only been possible with hydroxyapatite, rather than the silicon nitride-based materials disclosed herein. Materials with osteoconductive properties allow for ingrowth of bone-forming cells for mature bone formation. Materials with osteoinductive properties, by contrast, allow for stem cells or undifferentiated cells to differentiate into mature bone cells.

This allows for a number of applications. For example, in some such applications, treated silicon nitride materials, such as silicon-yttrium-aluminum-oxynitride (SiYAlON) and/or silicon yttrium oxynitride (SiYON) materials, or materials comprising a glaze of SiYAlON and/or SiYON, may be used in place of hydroxyapatite, which is a much weaker material. By providing a stronger material that has the osteoinductive characteristics of hydroxyapatite, various coatings, putties, and/or dental applications may be manufactured that may provide improved performance relative to hydroxyapatite. To be more specific, one or more of the materials disclosed herein may be coated on various implants, such as hip stems or rods, to assist with bone healing. Similarly, gels, putties, or other similar relatively viscous, yet fluid, compositions may be formed using the novel materials disclosed herein provide an additional source of bone to facilitate healing, enhance bone regeneration, provide osteoconduction and osteointegration, all while providing improved strength and toughness characteristics. Thus, the coatings referred to herein may be applied to biomedical implants, such as rods, screws, pins, and the like, or may be applied directly to bone, defects/cracks in bone, or otherwise where bone growth is desired.

In preferred embodiments, silicon nitride ceramic implants, may therefore be provided that may, in some embodiments, be treated so as to improve upon their osteoconductive characteristics, antibacterial characteristics, and/or other desirable characteristics. This may be done by forming the implant from the improved material as a monolithic implant, incorporating the improved material into an implant by way of coatings, fillers, matrix, etc., and/or treating an existing implant with one or more of the novel processes disclosed herein.

For example, embodiments and implementations disclosed herein may result in improved inhibition of bacteria adsorption and biofilm formation, improved protein adsorption, and/or enhanced osteoconductive and osteointegration characteristics. Such embodiments may comprise a silicon nitride ceramic or doped silicon nitride ceramic substrate. Alternatively, such embodiments may comprise a silicon nitride or doped silicon nitride coating on a substrate of a different material. In other embodiments, the implant and the coating may be made up of a silicon nitride material. In still other embodiments, one or more portions or regions of an implant may include a silicon nitride material and/or a silicon nitride coating, and other portions or regions may include other biomedical materials.

As still another alternative, the novel ceramic materials disclosed herein may be used as a filler or otherwise incorporated into other materials, such as glasses, metals, ceramics, polymers, and the like. For example, in some embodiments, one or more of the ceramic materials disclosed herein may be used as a filler in a polymeric material, such as polyetheretherketone (PEEK). Conversely, the ceramic material disclosed herein could be used as a porous matrix to incorporate polymeric materials, glasses or metals. Since PEEK is commonly used in spinal implants and other biomedical implants, incorporating one or more of the novel materials disclosed herein into the PEEK, by using such material(s) as a filler or otherwise, may improve one or more desired characteristics of the resulting implant.

In alternative embodiments and implementations, the surface chemistry of a silicon nitride material may be altered to improve the antibacterial and/or osteoconductive characteristics of such implants. In some such implementations, the chemistry of the surface of a monolithic device or coating on a silicon nitride implant, silicon nitride coated implant, or other implantable biomedical implant, may be modified to improve antibacterial and/or osteoconductive characteristics. These methods for altering the surface chemistry may be employed as an alternative to, or in addition to, other methods described herein, such as methods for changing the surface roughness of an implant and/or applying a suitable coating to a biomedical implant. These methods for altering the surface chemistry may also be accomplished in several ways, as further described below.

As another alternative, silicon nitride or other similar ceramic materials may be incorporated into other materials used to form biomedical implants. For example, silicon nitride may be used as a filler or otherwise incorporated into polymers, such as poly-ether-ether-ketone (PEEK), poly (methyl methacrylate), poly(ethylene terephthalate), poly (dimethylsiloxane), poly(tetrafluoroethylene), polyethylene, and/or polyurethane, and the like. Silicon nitride may also be used as a filler or otherwise incorporated into other materials used to form other biomedical implants, such as metals, including titanium, silver, nitinol, platinum, copper, cobalt/chromium, and related alloys, for example. As still another alternative, silicon nitride may be used as a filler or otherwise incorporated into other materials, such as ceramics and cermets.

In embodiments including one or more coatings, the coating(s) can be applied by any number of methods such as chemical vapor deposition (CVD), physical vapor deposition (PVD), plasma spraying, electro-deposition or electrophoretic deposition, slurry coating and high-temperature diffusion, or any other application method known by those skilled in the art. In some embodiments, the coating thickness can range from between about 5 nanometers up to about 5 millimeters. In some such embodiments, the coating thickness may be between about 1 micrometer and about 125 micrometers. The coating may adhere to the surface of the implant, but need not necessarily be hermetic.

Silicon nitride ceramics have tremendous flexural strength and fracture toughness. In some embodiments, such ceramics have been found to have a flexural strength greater than about 700 Mega-Pascal (MPa). Indeed, in some embodiments, the flexural strength of such ceramics have been measured at greater than about 800 MPa, greater than about 900 MPa, or about 1,000 MPa. The fracture toughness of silicon nitride ceramics in some embodiments exceeds about 7 Mega-Pascal square-root meter (MPa·m$^{1/2}$). Indeed, the fracture toughness of such materials in some embodiments is about 7-10 MPa·m$^{1/2}$.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide (MgO), and strontium oxide (SrO), can be processed to form a doped composition of silicon nitride. In embodiments comprising a doped silicon nitride or another similar ceramic material, the dopant amount may be optimized to achieve the highest density, mechanical, osteoconductivity, and/or antibacterial properties. In further embodiments, the biocompatible ceramic may have a flexural strength greater than about 900 MPa, and a fracture toughness greater than about 9 MPa·m$^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

Silicon nitride has been discovered to have unexpected antibacterial properties and increased bone formation properties. Indeed, as discussed in greater detail below, it has been recently demonstrated that the adhesion and growth of bacteria on silicon nitride materials is substantially reduced with respect to other common spinal implant materials, such as titanium and poly-ether-ether-ketone (PEEK). As discussed in greater detail below, compared to medical grade titanium and PEEK, silicon nitride significantly inhibits in vitro and in vivo bacteria colonization, and bio-film formation. Silicon nitride also exhibits a much lower live count and live to dead ratio for bacteria during studies, and also has a greater appositional bone formation than other common spinal implant materials, such as titanium and PEEK, and facilitates greater bone formation within surgical defects.

It has also been demonstrated that silicon nitride materials provide significantly greater adsorption of vitronectin and fibronectin, which proteins are known to decrease bacteria function and aid osteoblast formation, than titanium and PEEK. It is thought that these properties will be very useful in biomedical implants of all types by significantly reducing the possibility of infection and increasing bone formation. This may be accomplished by, for example, preventing or disrupting bacterial formation on/in the implant and/or killing bacteria that have been transferred to the implant and facilitating the differentiation of mesenchymal stem cells into osteoblasts.

Without being limited by theory, it is thought that the higher adsorption of proteins that characterizes silicon nitride may facilitate the inhibition of bacteria growth and also promote stem cell differentiation to osteoblasts. This preferential adsorption may be a cause for silicon nitride's ability to decrease bacteria function and increase bone formation. Again, without being limited by theory, the mechanisms for the enhanced antibacterial characteristics of silicon nitride may be a combination of its features. For example, its hydrophilic surface may lead to preferential adsorption of proteins that are responsible for reduced bacteria function and increased bone formation. This effect may be enhanced by increasing the surface texture or roughness of a silicon nitride-like or silicon nitride-based implant or silicon nitride-like or silicon nitride-based coating on an implant made up of a different material. Because of these characteristics, silicon nitride also exhibits enhanced in vivo osteoconduction and osteointegration when compared with titanium or PEEK.

As discussed above, using a silicon nitride coating on one or more regions of an implant's surface may, in some embodiments and implementations, inhibit bacterial adhesion, while increasing/fostering adsorption of proteins necessary for healing and bone reformation. This same effect may, in other embodiments, be accomplished using monolithic silicon nitride as an implant.

In such embodiments, the surface of the ceramic implant may be engineered to provide for an increased degree of micro-roughness and surface texture to enhance these desirable properties. For example, in some embodiments, the micro-roughness—i.e., the texture of the surface in between the peaks and valleys typically measured by Ra values—may also, or alternatively, be increased by suitable texturing. In some implementations, the micro-roughness of the implant and/or coating may be increased by micromachining, grinding, polishing, laser etching or texturing, sand- or other abrasive-blasting, chemical, thermal or plasma etching, and the like. Micro-roughness may be measured by measuring the height of surface asperities using cut-off limits on a profilometer. This method may be used to selectively assess the roughness of a surface between the peaks and valleys. Alternatively, or additionally, the skewness and/or kurtosis could be measured. These measurements consider the deviation of the surface from what might be expected of a normal Gaussian distribution of surface roughness. Such surface engineering may also be performed on a silicon nitride coating, rather than on a monolithic silicon nitride or silicon nitride composite implant.

In some embodiments, the density of the silicon nitride material, or doped silicon nitride material, may vary throughout the implant, or throughout the portion of the implant made up of silicon nitride. For example, in spinal implant embodiments, the outermost layer, or a portion of the outermost layer, may be more porous, or less dense, than the core or center of the implant. This may allow for bone to grow into or otherwise fuse with a less dense portion of the implant, and the denser portion of the implant can be wear-resistant, and may have a higher strength and/or toughness, for example.

In certain embodiments, one or more inner portions of the implant may have a relatively low porosity ceramic, and thus exhibit high density and high structural integrity generally consistent with, and generally mimicking the characteristics of, natural cortical bone. And, by contrast, one or more of the surface coatings, layers, or linings formed at an outer surface of the implant can exhibit a comparatively greater or higher porosity that is generally consistent with and generally mimics the characteristics of natural cancellous bone. As a result, the higher porosity surface region(s), coating(s), or lining(s) can provide an effective bone ingrowth surface for achieving secure and stable bone ingrowth affixation of the ceramic portion of the implant (which, in some embodiments, comprises the entire implant) between a patient's vertebrae or another suitable location within the human body.

In some embodiments, the antibacterial and/or osteoconductive behavior of other implant materials, such as polymeric, metallic, or ceramics, may be improved through the application of silicon nitride as an adherent coating. This coating may, in some implementations, be roughened or textured to provide for increased surface area of the silicon nitride material/coating. In other embodiments, monolithic silicon nitride implantable devices may be provided which may be subjected to similar surface engineering.

The surface roughness values disclosed herein may be calculated using the arithmetic average of the roughness profile (Ra). Polished silicon nitride surfaces may have a roughness of 20 nm Ra or less. However, as discussed in greater detail below, counterintuitively, the antibacterial and/or osteoconductive properties of certain embodiments may be improved by roughening, rather than polishing, all or one or more portions of the surface of a silicon nitride ceramic or another similar ceramic implant. In some embodiments, a relatively rough surface may be created as part of the process of creating the material, such as during a firing stage, without further roughening or other surface engineering. However, in other embodiments, as discussed in greater detail below, the surface may be roughened to further increase the roughness beyond what would occur as a result of standard firing/curing alone. Thus, in some embodiments, the surface roughness may be greater than about 1,250 nm Ra. In some such embodiments, the surface roughness may be greater than about 1,500 nm Ra. In some such embodiments, the surface roughness may be greater than about 2,000 nm Ra. In some such embodiments, the surface roughness may be greater than about 3,000 nm Ra. In other embodiments, the surface roughness may be between about 500 nm Ra and about 5,000 nm Ra. In some such embodiments, the surface roughness may be between about 1,500 nm Ra and about 5,000 nm Ra. In some such embodiments, the surface roughness may be between about 2,000 nm Ra and about 5,000 nm Ra. In some such embodiments, the surface roughness may be between about 3,000 nm Ra and about 5,000 nm Ra.

In some embodiments, metallic, polymeric, or ceramic substrates may be pre-engineered with a surface texture onto which a silicon nitride coating may be applied. This texture can range from as low as about 5 nanometers up to about 5,000 nanometers or more in average surface roughness (Ra). Alternatively, as another embodiment, the surface texture of the silicon nitride coating itself can be increased, exclusive of the surface roughness of the substrate, to obtain a similar Ra range and resulting antibacterial effect. Some of the methods disclosed herein may therefore provide for engineering of the surface roughness of monolithic silicon nitride ceramic implants in order to improve their antibacterial performance, and other methods disclosed herein may provide for engineering the surface roughness of layers or coatings applied to substrates made up of any other suitable material available for use in biomedical implants. Of course, in some implementations, surface engineering may be applied to both the substrate and the coating.

Increasing the surface roughness of the ceramic can be accomplished using any number of known methods by those skilled in the art, including micromachining, grinding, polishing, laser etching or texturing, sand or other abrasive blasting, chemical etching, thermal etching, plasma etching, and the like.

The inventive techniques disclosed herein, including but not limited to the silicon nitride coatings and roughened surface finishes, may be applied to any number and type of biomedical components including, without limitation, spinal cages, orthopedic screws, plates, wires, and other fixation devices, articulation devices in the spine, hip, knee, shoulder, ankle and phalanges, catheters, artificial blood vessels and shunts, implants for facial or other reconstructive plastic surgery, middle ear implants, dental implants and devices, and the like.

As illustrated in the Examples presented below, in comparison with titanium and poly-ether-ether-ketone (PEEK), silicon nitride significantly inhibits in vitro and in vivo bio-film formation and bacterial colonization, and shows much lower bacteria live/dead ratios for bacteria, including but not limited to *Staphylococcus epidermidis* (*Staph. Epi.*), *Staphylococcus aureus* (*Staph. aureus*), *Enterococcus, Pseudomonas aeruginosa* (*Pseudo. aeruginosa*), and *Escherichia Coli* (*E. Coli*). Silicon nitride also demonstrates significantly higher in vitro adsorption of three proteins (Fibronectin, Vitronectin, and Laminin) which can displace or inhibit bacteria growth and promote stem cell differentiation to osteoblasts. Silicon nitride also facilitates greater appositional bone formation and bone growth within surgical defects.

In a clinical setting, bacteria are an ever present menace, particularly when associated with surgical intervention and the introduction of foreign material into the human body, such as orthopedic, cardiac or dental endoprostheses. Microorganisms introduced during surgery tend to initially populate the sterile surfaces of implants. Bacterial adhesion to the biomaterial surface is the essential step in the development of an infection. The human body's defensive mechanisms are triggered if the implant is excessively colonized by bacteria. Chronic infections arise when the bacterial colony reaches a critical size and overcomes the local host defenses. When this occurs, the body tends to encapsulate the infection and reject the implant. Consequently, patients typically must undergo re-operation, removal of the implant, treatment of the infection, and replacement of the implant. Deep wound infections associated with common orthopedic surgeries can be as high as 4% and cost up to $100,000 or more for corrective treatment. The reduction in quality of life and the associated cost of treating infections represents a significant burden for present day medical care.

Various embodiments and implementations disclosed herein will therefore provide materials and methods that resist bacterial adhesion, colonization, and growth, which, as discussed above, often lead to chronic infections. The embodiments and implementations disclosed herein may also provide for enhanced in vivo osteointegration and increased bone growth in comparison to other common implants, such as those made up of titanium and PEEK.

Factors influencing bacteria adhesion to biomaterial surfaces may include chemical composition, surface charge, hydrophilicity or hydrophobicity, and surface roughness or physical characteristics of the surface and/or coating of an implant. There are marked differences in the surface chemistry of metallic, polymeric, and ceramic implants. Metals have a thin protective oxide layer on their surfaces (typically less than about 25 nm in thickness). Polymers may also have oxide surfaces, but the oxides are typically part of longer chain carboxyl or hydroxyl groups. Both metallic and polymeric surfaces are often low in hardness, and therefore are easily abraded and highly sensitive to chemical attack and dissolution. Ceramics, such as silicon nitride, may also have oxide surfaces. However, unlike their metal counterparts, they are highly resistant to chemical and abrasive action.

Metallic and polymeric devices are also typically hydrophobic or weakly hydrophilic. Consequently, bacteria do not have to displace aqueous bodily fluids in order to adhere to the implant's surface. By contrast, ceramics, and silicon nitride in particular, are known to be more strongly hydrophilic than most metals and polymers. For instance, sessile water drop studies demonstrate that silicon nitride has higher wettability than either medical grade titanium or PEEK. Furthermore, the hydrophilicity of silicon nitride can be improved through the various inventive treatments discussed herein. The higher wettability of silicon nitride may be effective in inhibiting bacterial adhesion while concurrently promoting apatite deposition and osteoconductivity.

In order for bacteria to adhere to a hydrophilic surface, it must first displace the water that is present on the surface. Therefore, hydrophilic surfaces typically inhibit bacterial adhesion more effectively than do hydrophobic surfaces. It has also been shown that implant surface finish and texture play important roles in bacteria colonization and growth. Irregularities on the surface of typical polymeric or metallic implants tend to promote bacterial adhesion, whereas smooth surfaces tend to inhibit attachment and bio-film formation. This is true because rough surfaces have greater surface area and include depressions that provide favorable sites for colonization.

Counterintuitively, however, certain ceramic materials, including in particular silicon nitride-based ceramic materials, have been demonstrated to not only provide desirable antibacterial properties, but have also been demonstrated to provide further enhanced antibacterial properties with increased, rather than decreased, surface roughness. In other words, silicon nitride surfaces of higher roughness appear to be more resistant to bacterial adhesion than smooth surfaces. This is precisely the opposite of what is observed for many other implant materials, such as titanium and PEEK. As referenced above and as discussed in greater detail below, compared to medical grade titanium and PEEK, silicon nitride has been shown to significantly inhibit in vitro bacteria colonization and bio-film formation, and show a much lower live count and live to dead ratio for bacteria during studies. However, in studies between different types of silicon nitride, rough silicon nitride surfaces have been shown to be more effective in inhibiting bacterial colonization (rather than less effective as with most common implant materials) than polished silicon nitride (although both were much more effective in doing so than either titanium or PEEK).

Various embodiments and implementations will be further understood by the following Examples:

Example 1

In a first working example, the abilities of biomedical implant materials to inhibit bacterial colonization were tested. The study included silicon nitride materials, biomedical grade 4 titanium, and PEEK. Four types of bacteria were included in the study: *Staphylococcus epidermidis*, *Staphylococcus aureus*, *Pseudomonas aeruginosa*, *Escherichia coli*, and *Enterococcus*.

Implant samples in the study were sterilized by UV light exposure for 24 hours and surface roughness was characterized using scanning electron microscopy. Bacteria were then inoculated on the surfaces of the samples and incubated for 4, 24, 48, and 72 hours.

Two methods were used to determine bacteria function at the end of each time period: (1) Crystal violet staining; and (2) Live/dead assay. Bacteria were also visually counted using a fluorescence microscope with image analysis software. The experiments were completed in triplicate and repeated three times. Appropriate statistical analyses were then completed using Student t-tests.

For all bacteria, and all incubation times, the silicon nitride samples demonstrated lower bio-film formation, fewer live bacteria, and smaller live to dead bacteria ratios when compared with medical grade titanium and PEEK. Rough silicon nitride surfaces were even more effective in inhibiting bacterial colonization than polished surfaces. In addition, silicon nitride implants with polished or rough surfaces were both significantly better in inhibition of bacterial colonization than either titanium or PEEK.

Bio-film formation was also much higher for titanium and PEEK than for silicon nitride. For example, bio-film formation for *Staphylococcus aureus* on titanium was three times higher than polished silicon nitride after 72 hours of incubation and more than eight times higher than PEEK after 72 hours of incubation. And the results were even better using relatively rough silicon nitride having a surface roughness of about 1,250 nm Ra. Bio-film formation for *Staphylococcus aureus* on this rougher silicon nitride was less than half of that for the polished silicon nitride after 72 hours.

Live bacteria counts followed similar patterns. Live bacteria counts after 72 hours of incubation were between 1.5× and 30× higher for titanium and PEEK when compared with silicon nitride. And, again, rough silicon nitride outperformed polished silicon nitride. For example, for *Pseudomonas aeruginosa*, live bacteria count after 72 hours for rough silicon nitride (again, about 1,250 nm Ra) was about one-fifth of that for polished silicon nitride.

Live/dead bacteria ratios were similarly lowest for silicon nitride, and generally lower for rough silicon nitride than for polished silicon nitride. For example, live/dead ratios after 72 hours of incubation for *E. coli* on polished silicon nitride were over three times as high for titanium and about twice as high for PEEK. For rough silicon nitride, live/dead ratios were about six times as high for titanium and nearly three times as high for PEEK.

Example 2

In this study, the ability of biomedical implant materials to adsorb common bone-forming proteins was tested. As with Example 1, rough silicon nitride, polished silicon nitride, medical grade titanium, and PEEK were tested. The proteins tested were fibronectin, vitronectin, and laminin. Enzyme-linked immunosorbent assays (ELISA) were performed for 20 minutes, 1 hour, and 4 hours. Fibronectin, vitronectin, or laminin were directly linked with primary rabbit anti-bovine fibronectin, anti-vitronectin, and anti-laminin, respectively. The amount of each protein adsorbed to the surfaces was measured with an ABTS substrate kit. Light absorbance at 405 nm on a spectro-photometer was analyzed with computer software. ELISA was performed in duplicate and repeated three different times per substrate.

For all incubation times, silicon nitride exhibited significantly greater adsorption of fibronectin and vitronectin when compared with titanium and PEEK. Silicon nitride also showed greater adsorption of laminin at 1 and 4 hours incubation in comparison to titanium and PEEK. Rough silicon nitride surfaces (approximately 1,250 nm Ra) were more effective in adsorption of proteins than polished silicon nitride surfaces. However, both silicon nitride surfaces were generally better than either titanium or PEEK, particularly for fibronectin and vitronectin. Without being limited by theory, it is thought that preferred adsorption of these proteins onto silicon nitride is a probable explanation for its improved bacterial resistance.

Example 3

In this study, in vivo bone formation, inflammation, and infection of various implant materials were studied using a Wistar rat calvaria model. The study considered the strength of bone attachment to these materials. Rough silicon nitride, medical grade titanium, and PEEK were used in the study.

The study was conducted by implanting sterilized samples into the calvaria of two-year old Wistar rats using standard techniques. Another group of samples was inoculated apriori with *Staphylococcus epidermidis* and implanted into a second group of similar Wistar rats.

The animals were sacrificed at 3, 7, 14, and 90 days. Histology was quantified for the number of macrophages, bacteria, and bio-film proteins surrounding each of the implant materials. In addition, push-out tests were performed to determine bone attachment results and performance.

After 3 days using the non-inoculated samples, the titanium and PEEK implants were unstable, and thus no histology was able to be performed. The silicon nitride implants (surface roughness of approximately 1,250 nm Ra) exhibited about 3-5% bone-implant interface, as measured using microscopic linear analysis, and about 16-19% new bone growth in the surgical area, as measured using microscopic areal analysis, after 3 days.

After 7 days using the non-inoculated samples, the titanium and PEEK implants were unstable, and thus no histology was able to be performed. The silicon nitride implants, by contrast, exhibited about 19-21% bone-implant interface and about 28-32% new bone growth in the surgical area after 7 days.

After 14 days using the non-inoculated samples, the titanium implant exhibited about 7% bone-implant interface and about 11% new bone growth in the surgical area. The PEEK implant exhibited about 2% bone-implant interface and about 14% new bone growth in the surgical area. The silicon nitride implants, by contrast, exhibited about 23-38% bone-implant interface and about 49-51% new bone growth in the surgical area after 14 days.

After 90 days without inoculation, the titanium and PEEK implants exhibited about 19% and 8% bone-implant interface, respectively, and about 36% and 24% new bone growth, respectively. The silicon nitride implants again performed much better. These implants exhibited a bone-implant interface of about 52-65% and new bone growth of about 66-71%.

With the inoculated samples, all implants were too unstable to perform histology at 3 and 7 days. After 14 days, the titanium implant exhibited only about 1% bone-implant interface, 75% bacteria-implant interface (measured using microscopic linear analysis), about 9% new bone growth in the surgical area, and about 45% bacterial growth in the surgical area. PEEK exhibited essentially no bone-implant interface, about 2% new bone growth, and about 25% bacterial growth. The bacteria-implant interface with PEEK was unclear. The inoculated silicon nitride implants exhibited a bone-implant interface of about 3-13% after 14 days. New bone growth with the silicon nitride implants was about 25-28%, and bacterial growth was about 11-15%.

After 90 days, the inoculated titanium implant exhibited about 9% bone-implant interface, about 67% bacteria-implant interface, about 26% new bone growth, and about 21% bacterial growth. The PEEK implant exhibited about 5% bone-implant interface, about 95% bacteria-implant interface, about 21% new bone growth, and about 88% bacterial growth. The inoculated silicon nitride implants exhibited a bone-implant interface of about 21-25% after 90 days. New bone growth with the silicon nitride implants was about 39-42%, and there was no measurable bacterial-implant interface or bacterial growth after 90 days. In fact, there were no bacteria detected on the silicon nitride implants after 90 days.

Push-out strengths were also substantially better with the silicon nitride implants than with either the titanium or PEEK implants after all implantation times were measured, both with and without inoculation. After 90 days implantation without inoculation, push-out strengths for the silicon nitride implants were more than twice as high as titanium and more than two-and-a-half times as high as PEEK. With inoculation, silicon nitride push-out strengths were even better compared to titanium and PEEK for all implantation times. Silicon nitride push-out strengths were more than five times those of either titanium or PEEK. These results demonstrate substantial bone attachment for silicon nitride when compared to titanium and PEEK.

Push out strengths were measured by taking a sectioned portion of the calvaria including the implant and cementing the calvaria to wood blocks over a support plate. A load was then applied to the implant and the force required to dislodge the implant from the calvaria was measured.

The histology results further confirm the tested push-out strengths. As discussed above, significantly greater new bone growth was observed in the calvaria defect area for silicon nitride when compared with titanium and PEEK at all implantation times and under all inoculation conditions.

The results in each of the Examples discussed above suggest that, compared to medical grade titanium and PEEK, silicon nitride results in a substantially better inhibition of in vitro bacterial colonization and bio-film formation, and results in a much lower live to dead ratio for all studied bacteria at all incubation periods. Silicon nitride also demonstrates significantly higher in vitro adsorption of three proteins which may inhibit bacteria growth and promote stem cell differentiation to osteoblasts. This preferential adsorption correlates with, and may be a causative factor in, silicon nitride's ability to decrease bacterial function. Silicon nitride also exhibits enhanced in vivo osteogenesis and osteointegration and demonstrates significant resistance to bacteria compared to titanium and PEEK.

The studies discussed in the Examples also tend to suggest that roughened silicon nitride implants generally outperform polished silicon nitride in terms of antibacterial function and/or bone growth and integration. These results suggest not only that monolithic silicon nitride implants and/or or other similar ceramic implants may be surface roughened in order to improve antibacterial function, but also that silicon nitride coatings may be applied to other implants (both silicon nitride and non-silicon nitride, such as metals, polymers, and/or other ceramics). Such coatings may be surface roughened to further improve antibacterial function and provide other desirable characteristics, as discussed above. Preliminary research also tends to indicate that increasing the surface roughness beyond the levels used in the Examples—i.e. about 1,250 nm Ra—may further increase the antibacterial function of the material. For example, in some such embodiments, the surface roughness may be greater than about 1,500 nm Ra. In some such embodiments, the surface roughness may be greater than about 2,000 nm Ra. In some such embodiments, the surface roughness may be greater than about 3,000 nm Ra. In other embodiments, the surface roughness may be between about 500 nm Ra and about 5,000 nm Ra. In some such embodiments, the surface roughness may be between about 1,500 nm Ra and about 5,000 nm Ra. In some such embodiments, the surface roughness may be between about 2,000 nm Ra and about 5,000 nm Ra. In some such embodiments, the surface roughness may be between about 3,000 nm Ra and about 5,000 nm Ra.

Some alternative ceramic materials, such as alumina and zirconia ($ZrO_2$), for example, have certain properties that are similar to those of silicon nitride. As such, it is thought that these ceramic materials, or other similar materials, may exhibit similar antibacterial and osteogenic effects. It is thought that those of ordinary skill in the art, after having had the benefit of this disclosure, may be able to identify such alternative materials. It is also thought that these ceramic materials, or other similar materials, may exhibit improvement in antibacterial function with increased surface roughness, as is the case with silicon nitride ceramics.

Additional embodiments and implementations will be further understood by the following drawings.

FIG. 1A depicts a spinal implant 100. Spinal implant 100 has relatively smooth top, bottom, and side surfaces (102, 104, and 108, respectively). Spinal implant 100 may comprise a silicon nitride ceramic material or another similar ceramic material. Spinal implant 100 also comprises two openings 110 and 112 extending through the top and bottom surfaces of the implant. In some embodiments, spinal implant 100 may comprise a doped silicon nitride material, as described in greater detail above. One or more of the surfaces of spinal implant 100 may be roughened or textured to provide for increased surface area of the silicon nitride material making up the surface(s). For example, one or more surfaces of spinal implant 100 may be roughened or textured by micromachining, grinding, laser etching or texturing, sand or other abrasive blasting, chemical etching, thermal etching, plasma etching, and the like.

Figure 1B:
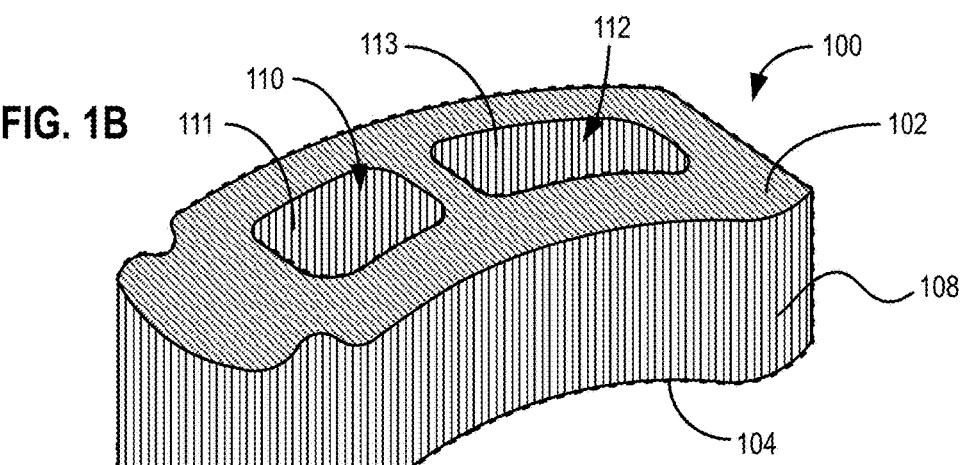
FIG. 1B is a perspective view of the spinal implant of FIG. 1A after a surface roughening process has been applied to the implant.

FIG. 1B depicts spinal implant 100 after each of the exterior surfaces 102, 104 (surface not visible in the figure), and 108 has been roughened. As explained above, this surface roughening improves the antibacterial function and characteristics of the implant. One or more interior surfaces may also be roughened. For example, interior surfaces 111 and 113 that define openings 110 and 112, respectively, may also be roughened. The extent of roughening of the interior surfaces may be identical to, greater than, or less than, the roughening of exterior surfaces 102, 104, and 108, as desired.

Figure 1C:
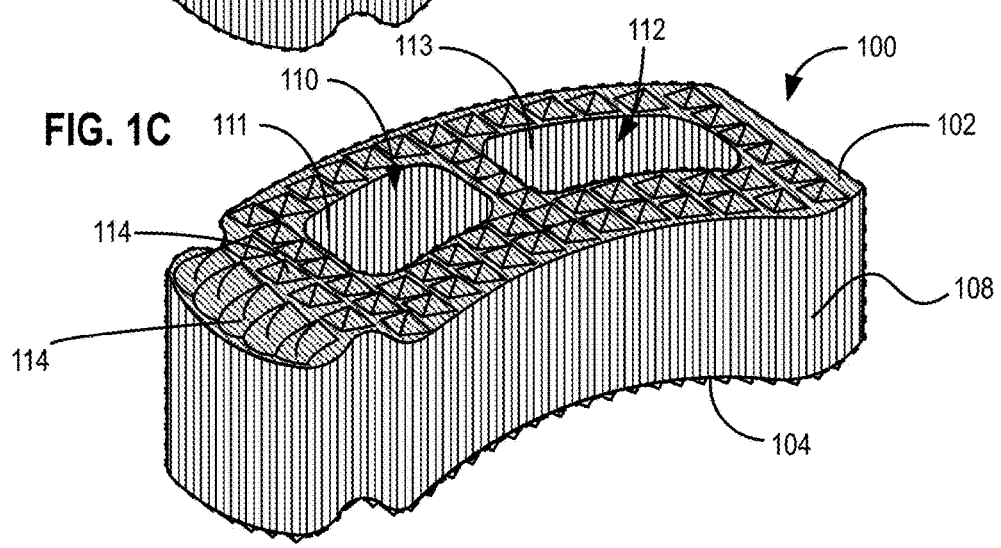
FIG. 1C is a perspective view of the spinal implant of FIG. 1B with surface features for minimizing implant migration.

FIG. 1C depicts spinal implant 100 having a plurality of surface features or teeth 114 on the top and bottom surfaces. Surface features 114 may help prevent or at least minimize migration of the implant once positioned within a patient's intervertebral space. Surface features 114 may be formed from the implant 100 before or after the surface roughening has taken place. Similarly, surface features 114 may, alternatively, comprise another material that is attached to the implant 100, again before or after surface roughening.

FIG. 2A depicts an alternative embodiment of a spinal implant 200. Spinal implant 200 may comprise any suitable material or materials, such as metals, polymers, and/or ceramics. Spinal implant 200 also comprises a coating 220. Coating 220 preferably comprises a silicon nitride or doped silicon nitride ceramic material, although it is contemplated that other ceramic materials having certain properties similar to silicon nitride may alternatively be used as a coating. Coating 220 may be applied to any surface exposed or potentially exposed to biological material or activity. For example, in the depicted embodiment, coating 220 is applied to top surface 202, bottom surface 204, side surface 208, and to interior surfaces 211 and 213 that define openings 210 and 212, respectively. Coating 220 may be applied to take advantage of the unique antibacterial and/or osteoconductive properties and characteristics of silicon nitride discussed elsewhere herein. In some embodiments, the coating thickness can range from between about 5 nanometers up to about 5 millimeters. In some preferred embodiments, the coating thickness may be between about 1 micrometer and about 125 micrometers.

For example, because PEEK, which is very common in spinal implants, performs very poorly in a bacterial environment and is also poor in terms of its osteointegration, silicon nitride ceramic coatings or layers (or another similar material) may be applied to a PEEK spinal implant to improve its osteointegration and/or antibacterial function of the implant and/or to provide other advantages as discussed in greater detail above. The coating(s) may be applied by any suitable methodology known to those of ordinary skill in the art, such as chemical vapor deposition (CVD), physical vapor deposition (PVD), plasma spraying, electro-deposition or electrophoretic deposition, slurry coating and/or high-temperature diffusion.

To further enhance the antibacterial and/or osteoconductive characteristics of the implant, the coating 220, or one or more portions of the coating 220, may be surface roughened, as illustrated in FIG. 2B. The coating surface roughening may be applied to any and all portions of the implant that are or could be exposed to biological activity or material. For example, in the embodiment depicted in FIG. 2B, each of surfaces 202, 204, 208, 211, and 213 have been roughened or textured as described above. In some embodiments, the surface of the implant may be roughened or textured before the coating is applied, either in lieu of, or in addition to surface roughening or texturing on the coating.

The principles, materials, and methods described herein may also be applied to other biomedical implants. For example, FIGS. 3A-3B and 4A-4B illustrate a hip implant 300 comprising a femoral stem 330 that is configured to be received within a patient's femur, a neck 340, and a modular acetabular head 350 configured to receive a ball joint (not shown) that will ultimately be positioned in an acetabular cup, or within a patient's natural acetabulum.

Figure 3A:
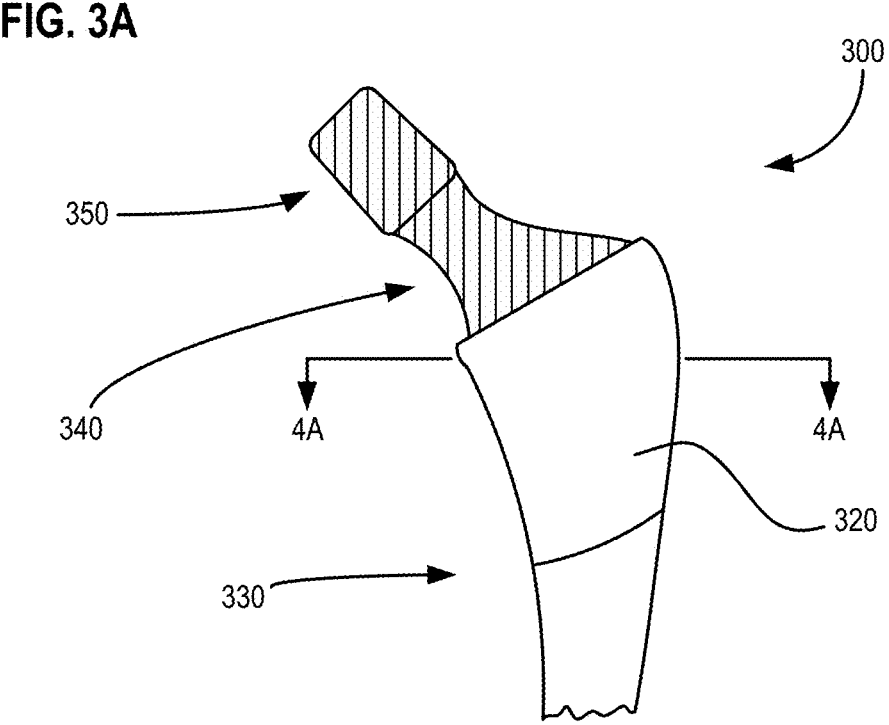
FIG. 3A is a perspective view of an embodiment of a hip stem implant having a coating applied to a portion of the implant.

One or more coatings 320 may be applied to the femoral stem 330 of hip implant 300, as shown in FIG. 3A. In preferred embodiments, coating 320 comprises a silicon nitride ceramic material. In alternative embodiments, other portions of the implant may also be coated with a silicon nitride ceramic or another similar material. For example, coating 320 may also be applied to femoral stem 330, neck 340, and/or modular acetabular head 350, as desired.

Figure 3B:
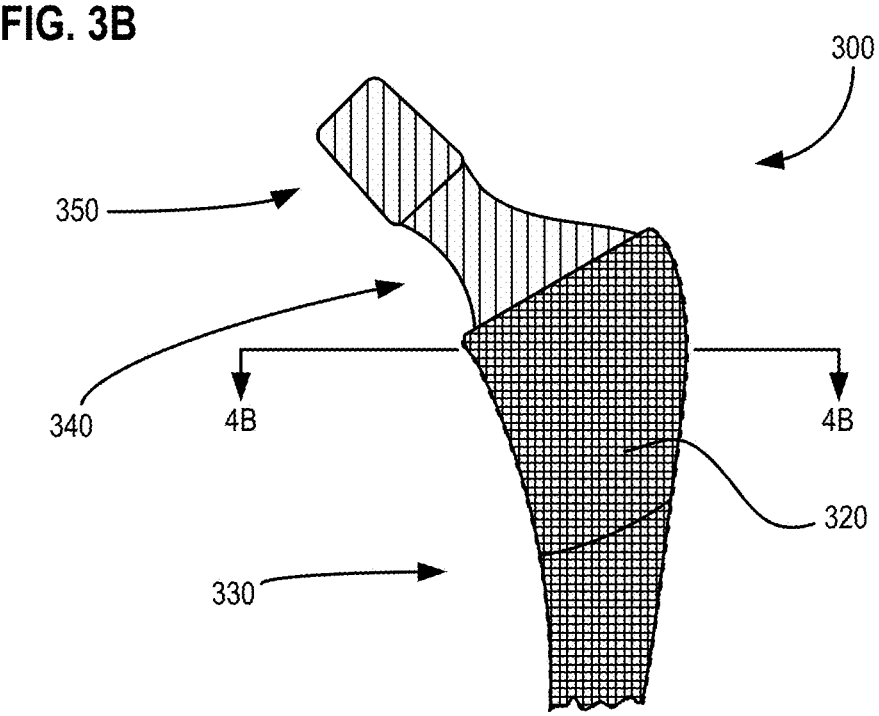
FIG. 3B is a perspective view of the embodiment of FIG. 3A after a surface roughening process has been applied to the coating of the implant.

In order to further enhance the antibacterial and/or osteointegrative properties of the implant 300, one or more surfaces/portions of the implant 300 may be roughened and/or textured. For example, as shown in FIG. 3B, femoral stem 330, which comprises coating 320, may be roughened and/or textured after coating 320 has been applied. Alternatively, femoral stem 330 and/or any other desired region of implant 300 (or any of the other implants discussed herein) may be roughened and/or textured before coating 320 has been applied. As yet another alternative, one or more surfaces of the implant may be textured and/or roughened both before and after the antibacterial and/or osteointegrative coating 320 has been applied.

Figure 4A:
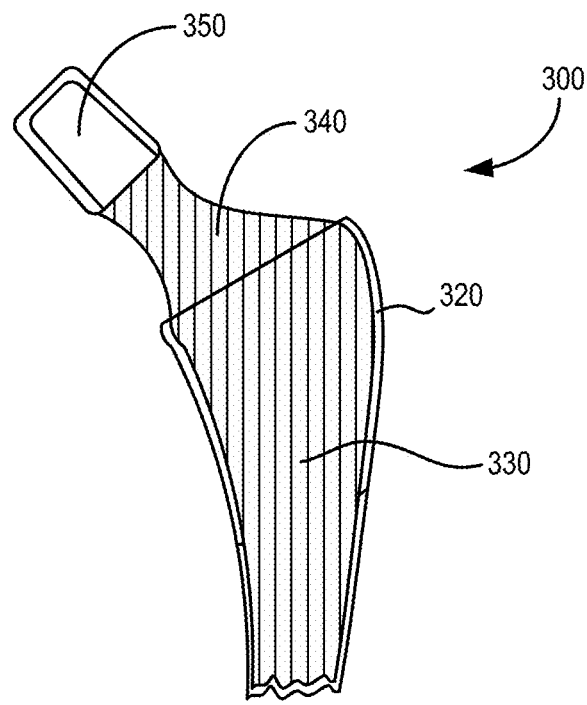
FIG. 4A is a cross-sectional view taken along line 4A-4A in FIG. 3A.

FIG. 4A is a cross-sectional view taken along line 4A-4A in FIG. 3A. As shown in this figure, coating 320 extends only along the femoral stem 330 portion of implant 300. However, as discussed above, in alternative embodiments, coating 320 may be applied to other portions of the implant as well (in some embodiments, the coating may be applied to the entire implant).

Figure 4B:
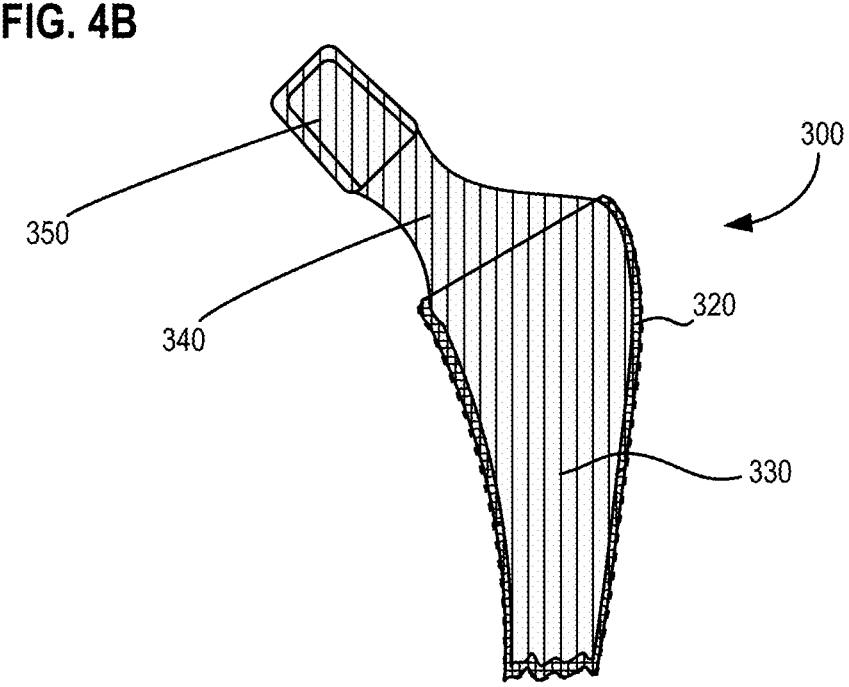
FIG. 4B is a cross-sectional view taken along line 4B-4B in FIG. 3B.

FIG. 4B is a cross-sectional view taken along line 4B-4B in FIG. 3B. This figure illustrates the surface of the femoral stem 330 of implant 300 after the roughening/texturing process has been completed.

Figure 5A:
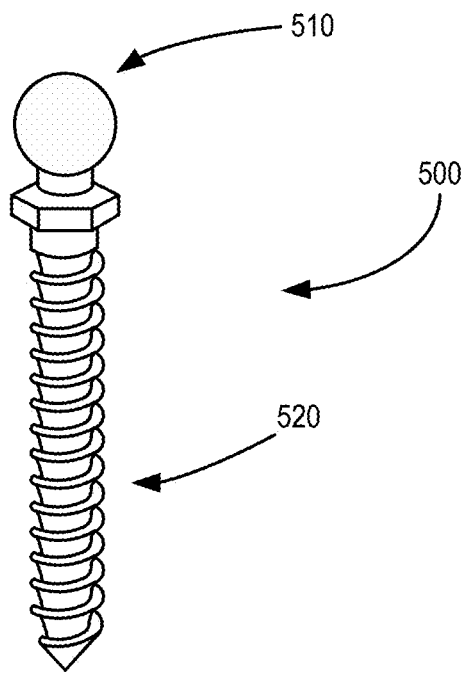
FIG. 5A is a perspective view of an embodiment of a bone screw implant.
Figure 5B:
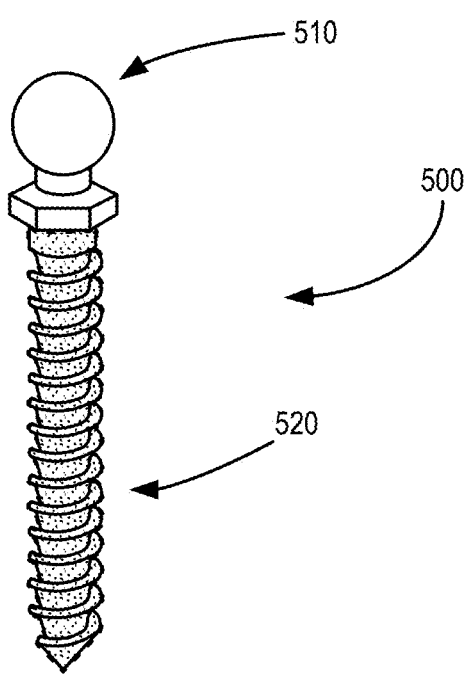
FIG. 5B is a perspective view of the embodiment of FIG. 5A after a surface roughening process has been applied to the implant.

Still other alternative embodiments are depicted in FIGS. 5A and 5B. These figures illustrate a bone screw 500. Bone screw 500 may comprise a pedicle screw, for example. Bone screw 500 comprises a spherical head 510 and a threaded shaft 520. Bone screw 500, or one or more portions of bone screw 500, may comprise a silicon nitride ceramic material. One or more portions or surfaces of bone screw 500 may also be roughened or textured to improve antibacterial or other characteristics of the implant. For example, as shown in FIG. 5B, threaded shaft 520 has been roughened. Head 510 of screw 500 may remain smooth, or may be polished smooth, to provide for desired articulation within a spinal fixation system connector. However, for other embodiments, it may be desirable to roughen the surface of head 510 as well. This may provide for not only the improved antibacterial and/or osteointegrative characteristics discussed herein, but may also provide a desirable friction interface with another component of a spinal fixation system.

In other embodiments, bone screw 500, or any of the other embodiments disclosed herein, may comprise another suitable material, such as titanium. In such embodiments, a silicon nitride coating may be applied to the implant rather than forming the entire implant from a silicon nitride material. As disclosed above, the coating and/or the undersurface of the coating (i.e., the surface of the original implant itself) may be roughened or textured to further improve antibacterial, osteointegrative, and/or other characteristics.

In still other embodiments, bone screw 500, or any of the other embodiments disclosed herein, may comprise a biomedical material, such as a metal, ceramic, or polymer that includes a silicon nitride filler, or that otherwise incorporates a silicon nitride material into the material used to form the implant. For example, silicon nitride may be used as a filler or otherwise incorporated into polymers, such as poly-ether-ether-ketone (PEEK), poly(methylmethacrylate), poly(ethyleneterephthalate), poly(dimethylsiloxane), poly(tetrafluoroethylene), polyethylene, polyurethane, and the like. Silicon nitride may also be used as a filler or otherwise incorporated into other materials used to form other biomedical implants, such as metals, including titanium, silver, nitinol, platinum, copper, and related alloys, for example. As still another alternative, silicon nitride may be used as a filler or otherwise incorporated into other materials, such as glasses, other ceramics, and/or cermets. By incorporating silicon nitride into other materials, it is expected that some of the antibacterial and/or osteointegrative advantages and/or other advantageous properties described herein may be realized. Silicon nitride may also be incorporated into another material used as part of one or more of the coatings described herein to increase antibacterial function.

As another specific example, in some embodiments and implementations, one or more of the improved ceramic materials disclosed herein may be included as a filler or mixed or otherwise incorporated into materials used to manufacture catheters. Because of the enormous problem associated with bloodstream infections, often caused by microorganisms residing on intravascular catheters, incorporation of such materials into other materials used to manufacture catheters, such as typically plastic or polymeric materials, may improve the antibacterial characteristics and/or other aspects of such catheters.

In alternative embodiments and implementations, the surface chemistry of silicon nitride implants, silicon nitride coated implants, or other implantable biomedical implants may be altered to improve the antibacterial and/or osteoconductive characteristics of such implants. Such methods may be employed in addition to, or in lieu of, the surface roughening and/or coating steps described above. Such methods for altering the surface chemistry of biomedical implants to improve antibacterial and/or osteoconductive characteristics may be accomplished using several different implementations, as described herein.

For example, silicon nitride implants, including both monolithic silicon nitride implants and implants comprising silicon nitride coatings, often have a thin transitional oxide layer on their surface. This transitional oxide layer typically comprises a gradient wherein higher concentrations of nitrogen are positioned near the silicon nitride grains, and higher concentrations of oxygen are positioned at relatively greater distances from the silicon nitride grains.

The overall surface charge for silicon nitride can be markedly affected by the amount of either nitrogen or oxygen which is present in this transitional oxide layer. It has also been discovered that the concentration of point defects in the surface lattice structure of silicon nitride may further affect surface charge. If more nitrogen is present in the form of amine groups ($SiNH_3^+$), then the surface tends to have a more positive charge. Similarly, higher concentrations of nitrogen vacancies in the transitional oxide layer (which are positively charged defects) may lead to an increase in overall surface charge. Furthermore, the presence of amine groups (particularly quaternary amines) and a more positive surface charge may aid in improved hydrophilicity, osteoconductivity and in prevention of biofilm formation for certain types of bacteria.

Conversely, higher concentrations of hydroxyl groups (SiOH), non-bridging oxygen hole centers (NBOHC), and $N2^0$ ($Si2N^-$) defects may induce a more negative surface charge. The behavior of these negatively charged defects may also beneficially aid in improved hydrophilicity, osteoconductivity, and/or resistance to certain other bacteria. Consequently, depending upon pH and the concentration of either positively or negatively charged ions in the biologic fluids, the surface charge of silicon nitride can be either positive, zwitterionic (zero net charge) or negative. Accordingly, the osteoconductivity, antibacterial characteristics, and/or other desirable characteristics of silicon nitride material may be improved by changing the surface chemistry and, in some implementations, the surface charge, of such implants.

To use silicon nitride implants as an example, changes in surface chemistry may result from reactions with the environment in accordance with, for example, the following chemical equations:

$$Si_3N_4 + H_2O \rightarrow Si_2NH + SiOH$$

$$Si_2NH + H_2O \rightarrow SiNH_2 + SiOH$$

Hydrogen can also be absorbed or desorbed from the surface depending upon the pH of the surrounding environment via, for example, the following reactions:

$$SiNH_2 + H^+ \rightarrow SiNH_3^+$$

$$SiOH + H^+ \rightarrow SiOH_2^+$$

$$SiOH \leftrightarrow SiO^- + H^+$$

In this context, H atoms may be shared by the two dangling Si bonds of an N vacancy defect site (also referred to as "negative correlation energy" (NCE) centers). In addition to the above-referenced chemical reactions, the charging of NCE centers may lead to local geometric changes of the lattice, which may account for the experimental finding that the local pH of acidic fluids increases at the silicon nitride surface. This may be because large amounts of hydrogen ions (driven towards excess-silicon sites) may migrate from the surrounding fluid toward the silicon nitride surface. This "pH buffering" property appears to be peculiar to silicon nitride ceramics and is thought to be one of the reasons for its antibacterial behavior, besides being helpful in a number of clinical circumstances (e.g., periodontitis).

Desirable results of one or more of these reactions on silicon nitride materials and/or related biomedical implants may be obtained, for example, by employing methods designed to increase the amount of nitrogen in the transitional oxide layer of, for example, a silicon nitride implant or an implant having a silicon nitride coating. Additionally, or alternatively, some implementations may comprise one or more chemical treatment steps.

For example, in some implementations, the implant, or at least a portion of the implant, may be cleaned in, for example, a highly caustic or acidic solution, such as hydrofluoric acid (HF). These solutions can strip the surface of its native oxide, leaving behind a nitrogen rich surface, which may be beneficial for preventing biofilm formation for at least some types of bacteria and may also have desirable osteoconductive effects.

For example, a solution having a pH of greater than about 10 should be considered highly caustic and a solution having a pH of less than about 4 should be considered highly acidic. Examples of caustic solutions that may be used in some implementations include solutions comprising sodium hydroxide (NaOH), ammonium hydroxide (NH$_4$OH), and/or potassium hydroxide (KOH). In some such implementations, the solution may comprise a molarity or molar concentration of sodium hydroxide, ammonium hydroxide, and/or potassium hydroxide of at least about 1.0.

Examples of acidic solutions that may be used in some implementations include solutions comprising hydrofluoric acid, as mentioned above, as well as sulfuric acid (H$_2$SO$_4$), nitric acid (HNO$_3$), phosphoric acid (H$_3$PO$_4$), hydrochloric acid (HCl), and the like. In some such implementations, the solution may comprise a molarity or molar concentration of hydrofluoric acid, sulfuric acid, nitric acid, phosphoric acid, and/or hydrochloric acid of at least about 1.0. In some implementations, the solution, whether caustic or acidic, may be heated to further enhance the ability of the solution to remove the transitional oxide layer. In some such implementations, the solution may be heated to a boil before applying the solution to the implant/implant material.

In still other implementations, the composition of the transitional oxide surface layer may be altered by firing the implant in a high nitrogen environment. In some implementations, the implant may be fired in an environment that combines nitrogen and hydrogen, nitrogen and argon, nitrogen and ammonia, or nitrogen and carbon monoxide.

It has also been discovered that firing of monolithic silicon nitride ceramics in an oxidizing environment and/or a nitrogen-rich environment may lead to an increase in either positively- or negatively-charged defects. On the one hand, thermal oxidation of the surface leads to an increase in the thickness of the transitional oxide layer and a corresponding increase in the oxide content at the surface. This oxide-rich surface reacts with water to form silanol functional groups, which tend to deprotonate and exhibit negative charge at most pH values. Formation of positively-charged defects (e.g., nitrogen vacancies) in the near-surface transitional oxynitride layer has also been observed following thermal oxidation treatments. Further, constituents of the doped oxynitirde glass, such as yttrium and aluminum, have been shown to migrate to the surface during thermal oxidation treatments.

Thermal annealing of monolithic silicon nitride in a nitrogen-rich environment, or, possibly in other oxidizing environments, may migrate the doped oxynitride glass to the surface leading also to an increase in silanol groups and Al—OH & Y—OH groups, with a concomitant increase in positively charged defects in the near-surface transitional oxynitride layer. Consequently, it was concurrently beneficially discovered that both the nitrogen annealed and thermally oxidized samples showed improvements in hydrophilicity, osteoblast adhesion and proliferation, and apatite formation.

In some implementations comprising a firing step in a nitrogen rich environment, a ceramic material may be fired in an environment comprising at least essentially 100% nitrogen gas. In such implementations, the environment may be at approximately atmospheric pressure and may be at temperatures above about 1400° C. for extended time periods, typically greater than about 1 hour, and preferably greater than about 2 hours. In some such implementations, the environment may be at temperatures above about 1500° C.

With respect to silicon nitride ceramic materials, such firing environments may result in preferential evaporation of silicon monoxide (SiO) gas from the ceramic. Since evaporation occurs at the surface of the ceramic material, this process may result in removal of this species from the transitional oxide layer, leaving behind a nitrogen enhanced surface layer.

In various implementations, nitrogen gas pressure can be applied in the form of hot-isostatic pressing at temperatures of at least about 1500° C. and pressures of at least about 35 MPa to further enhance removal of the transitional oxide layer. This may be performed, for example, inside a furnace comprising graphite elements and/or supports. In such implementations, there may be small amounts (ppm levels) of carbon-monoxide gas present in the equipment, which may further aid in removing the oxide layer and thereby further enhance the antibacterial and/or osteoconductive properties of the resulting implant material.

In some implementations, one or more steps may be taken subsequent to firing in order to eliminate, or at least minimize, exposure of the implant to the natural environment.

This may be accomplished, for example, using suitable packaging to reduce or eliminate exposure to air and/or the natural environment. In addition, or alternatively, handling steps may involve nitrogen and/or nitrogen desiccation, such as, for example, use of nitrogen glove boxes. Alternatively, a vacuum or an inert atmosphere, such as one comprising argon gas, may be used. In some implementations, gas impermeable packaging may be used, into which the fired implants may be placed and sealed prior to removing them from a suitable glove box.

In still other implementations, the nitrogen content of the transitional oxide surface layer may be increased to improve osteoconductive and/or antibacterial characteristics by subjecting the implant to high energy nitrogen implantation using, for example, an ion gun. In some such implementations, nitrogen ions may be sub-planted into the surface of the transitional oxide layer, thereby resulting in a significant increase in nitrogen content, particularly with respect to silicon nitride coated implants. In some implementations involving such implants, the same or similar equipment used to deposit an adherent silicon nitride coating may also be used to increase the nitrogen content of the surface of this coating through ion implantation.

After having received the benefit of this disclosure, it will be apparent to those knowledgeable in the art that there may be numerous other ways of increasing the nitrogen content within the transitional oxide layer of a biomedical implant. Any number of such techniques may therefore be used that prove effective in improving the osteoconductive and/or antibacterial characteristics of biomedical implants, including but not limited to monolithic silicon nitride implants and/or implants comprising silicon nitride coatings.

In some embodiments and implementations, the antibacterial characteristics of an implant may be further improved by adding any number of antibacterial metals, including but not limited to silver (Ag), copper (Au), selenium (Se), zinc (Zn), and the like. For example, in some implementations involving high energy ion implantation, a relatively small amount of silver or another such antibacterial metal ion may be included in the ion source used during the implantation process. In some implementations, such metal ions may comprise about 5 to about 15% atomic percent of silver and/or other such metal ions relative to all of the ions added to the transitional oxide layer of the material. The addition of such ions to the transitional oxide layer of, for example, a monolithic silicon nitride ceramic implant material block, is likely to result in further improvements to the antibacterial characteristics of the resulting implant. In some embodiments and implementations, silver and/or other such antibacterial metal ions may be added to silicon nitride or other biomedical implant materials by ion implantation, as described elsewhere herein.

However, it should be understood that other embodiments and implementations are contemplated that are not restricted solely to silicon nitride ceramics, but may be more broadly applicable to a wide variety of other biomaterials, including metals and plastics. Such materials may also, or alternatively, be implanted with nitrogen ions into their native surface oxides to increase their nitrogen content and accompanying resistance to bacteria, as discussed above.

With respect to certain implementations and embodiments involving biomedical implants comprising silicon nitride coatings, antibacterial metals and silicon nitride may be co-deposited, either simultaneously or sequentially. In some such implementations, the deposition process may utilize a dual magnetron sputtering process and/or a combination reactive PVD deposition of silicon nitride concurrent with PVD application of silver. Again, it is expected that only a few atomic percent of an antibacterial metal may be useful for imparting significant antibacterial improvements.

Figure 6:
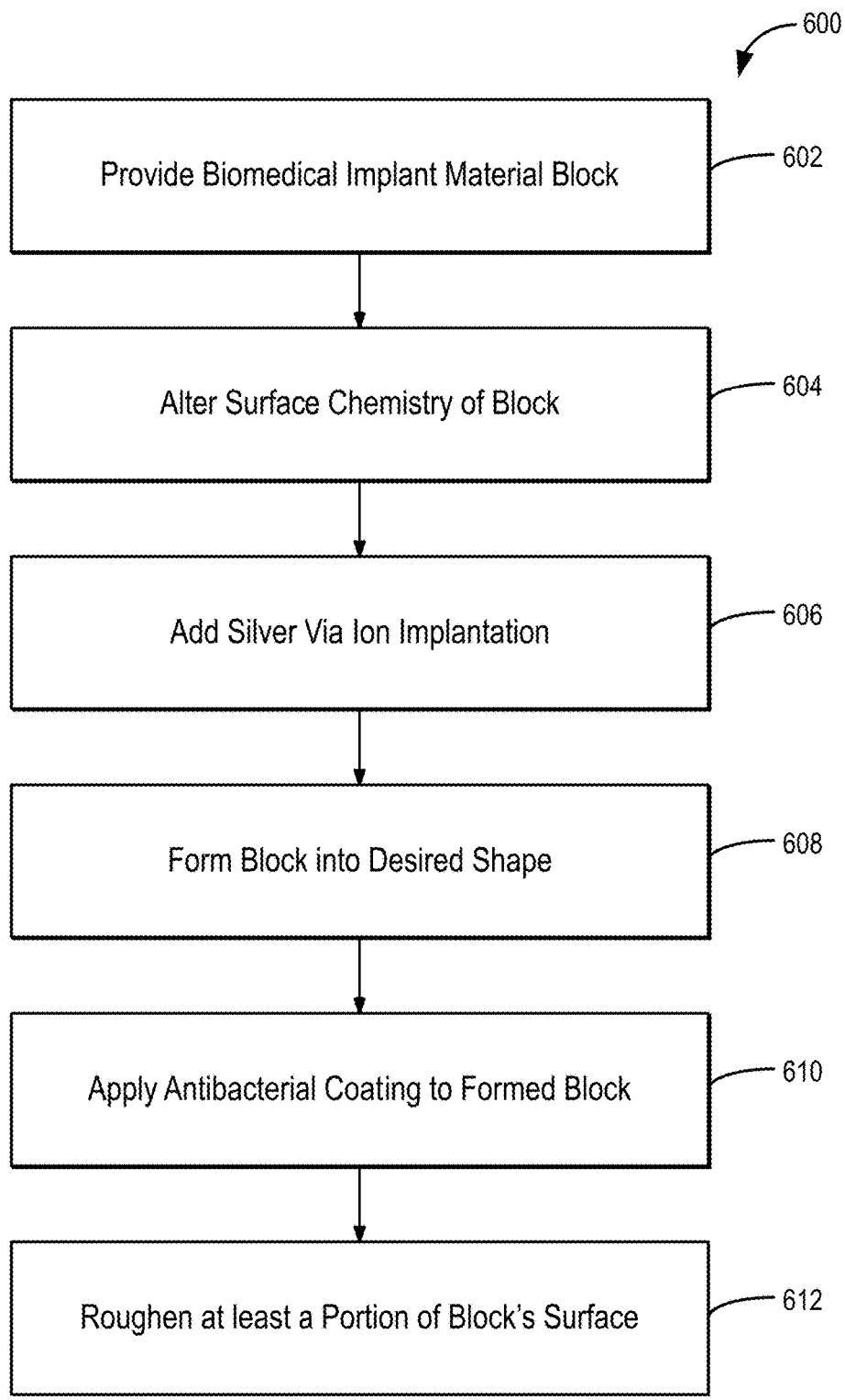
FIG. 6 is a flow chart depicting an example of an implementation of a method for improving the antibacterial characteristics of a biomedical implant.

FIG. 6 is a flow chart depicting an example of an implementation of a method 600 for improving the antibacterial characteristics of a biomedical implant. At step 602, a biomedical implant material block is provided. In some implementations, the biomedical implant material block may comprise a finished biomedical implant, such as an intervertebral spacer or other spinal implant, orthopedic screw, orthopedic plate, spinal articulation device, hip implant, knee implant, shoulder implant, ankle implant, shunt, stent, facial or other reconstructive plastic surgery implant, dental device, etc.

In other implementations, the biomedical implant material block may comprise an unfinished piece of material that will ultimately be shaped, machined, or otherwise formed into a suitable shape and/or configuration to serve as one of the above-referenced finished biomedical implants. In some such implementations, the unfinished piece of may require one or more additional processing steps—other than shaping and other than the steps involved in process 600—before it can be considered completed and ready for implantation. For example, in some implementations, the biomedical implant block may comprise only a part or portion of what will eventually become a finished biomedical implant.

Following step 602, one or more steps may be performed to improve the antibacterial characteristics of the biomedical implant material block. For example, in process 600, at step 604 the surface chemistry of the biomedical implant material block may be altered in order to improve the antibacterial characteristics of the biomedical implant material block. In some implementations, step 604 may comprise a step that alters the surface chemistry of the biomedical implant material block.

Step 604 may comprise, for example, increasing the amount of nitrogen in the transitional oxide layer of the biomedical implant material block. This may be particularly useful in connection with implementations comprising a silicon nitride biomedical implant material block or a biomedical implant material block comprising a silicon nitride coating. In some implementations, the nitrogen content of the transitional oxide surface layer may be increased at step 604 by firing the implant in a high nitrogen environment. In some implementations, the implant may be fired in an environment that combines nitrogen and hydrogen, nitrogen and carbon monoxide, or nitrogen and ammonia, in order to increase the amount of nitrogen in the transitional oxide layer of the biomedical implant material block.

In alternative implementations, step 604 may comprise altering the surface chemistry of the biomedical implant material block using one or more chemical treatment steps. For example, in some implementations, the biomedical implant material block, or at least a portion of the biomedical implant material block, may be cleaned in, for example, a highly caustic or highly acidic solution, such as sodium hydroxide (NaOH) or hydrofluoric acid (HF). Such solutions may be used to strip the surface of its native oxide, leaving behind a nitrogen rich surface in order to enhance the block's osteoconductive and/or antibacterial characteristics.

In some implementations, one or more steps may be taken subsequent to step 604 in order to eliminate, or at least minimize, exposure of the implant to the natural environment. This may be accomplished, for example, using suitable packaging and/or handling steps involving nitrogen and/or nitrogen desiccation.

In still other implementations, step 604 may comprise increasing the nitrogen content of the transitional oxide surface layer by subjecting the biomedical implant material block to high energy nitrogen implantation using, for example, an ion gun. In some such implementations, the high energy nitrogen implantation may be sufficient to implant nitrogen ions into the surface of the transitional oxide layer of the biomedical implant material block.

At step 606, an antibacterial metal, such as silver (Ag), may be added to the biomedical implant material block by high energy ion implantation. In some implementations, about 5 to about 15% atomic percent of silver may be added to the transitional oxide layer of the biomedical implant material block to further enhance the antibacterial characteristics of the implant. In some implementations, particularly implementations in which silicon nitride coatings are employed, the antibacterial metal and silicon nitride may be co-deposited, either simultaneously or sequentially, as part of step 606. In some such implementations, the deposition process may utilize a dual magnetron sputtering process and/or a combination reactive PVD deposition of silicon nitride concurrent with PVD application of silver ions.

Step 608 may comprise machining or otherwise forming the biomedical implant material block into a suitable shape/form for a desired biomedical implant. As mentioned above, in some implementations, the biomedical implant material block may comprise a pre-formed block already in a desired shape. In such implementations, step 608 would, of course, be omitted.

At step 610, an antibacterial coating, such as a silicon nitride coating, may be applied to at least a portion of the formed biomedical implant material block. In some implementations, such a coating may be applied to the entire exposed surface of the formed biomedical implant material block. Such coating or coatings may also comprise antibacterial metal ions, such as silver ions, which may be deposited simultaneously with deposition of the coating(s) or, alternatively, may be deposited onto the coating after the coating has been applied Various methods may be used in order to apply the antibacterial coating(s). For example, coatings may be applied by way of a variety of processes, such as physical vapor deposition (PVD) or chemical vapor deposition (CVD) processes. More specifically, antibacterial coatings can be applied via low or high-temperature reactive CVD (i.e., LT-CVD, HT-CVD), DC or RF plasma-assisted CVD, DC or RF assisted PVD, balanced or unbalanced magnetron sputtering, ion-beam assisted deposition (IBAD), filtered cathodic arc deposition (FCAD), pulsed laser ablation and deposition (PLAD), electron cyclotron resonance CVD (ECR-CVD), or any other appropriate physical vapor deposition (PVD) or chemical vapor deposition (CVD) processes.

Finally, at step 612, at least a portion of the surface of the biomedical implant material block may be roughened to further enhance osteoconductive and/or antibacterial characteristics. In some implementations, this roughening step may comprise applying a texture to the biomedical implant material block. Step 612 may be performed using, for example, micromachining, grinding, polishing, laser etching or texturing, sand or other abrasive blasting, chemical etching, thermal etching, plasma etching, and the like. The surface roughness in some embodiments and implementations may be greater than about 1,200 nm Ra. In some such embodiments, the surface roughness may be greater than about 1,500 nm Ra. In some such embodiments, the surface roughness may be greater than about 2,000 nm Ra. In some such embodiments, the surface roughness may be greater than about 3,000 nm Ra. In other embodiments, the surface roughness may be between about 500 nm Ra and about 5,000 nm Ra. In some such embodiments, the surface roughness may be between about 1,500 nm Ra and about 5,000 nm Ra. In some such embodiments, the surface roughness may be between about 2,000 nm Ra and about 5,000 nm Ra. In some such embodiments, the surface roughness may be between about 3,000 nm Ra and about 5,000 nm Ra.

It should be understood that some implementations can be practiced without some or all of the steps disclosed above. In addition, the steps of a method do not necessarily need to be executed in any specific order, or even sequentially, nor need the steps be executed only once, unless otherwise specified. For example, with respect to the method 600 of FIG. 6, it is contemplated that some implementations may omit one or more steps, such as step 610 of adding an antibacterial coating. Similarly, in some implementations, step 612 of roughening at least a portion of a surface of the implant may be performed prior to 610 or, alternatively, both before and after step 610. As another example, the forming/machining step 608 may be performed before any of the steps listed in process 600 prior to step 608 if desired. For example, the implant may be fully formed/machined before altering the surface chemistry of the implant according to step 604 in some implementations. In addition, as another example, and as mentioned above, some implementations may comprise a pre-formed biomedical implant material block, in which case the forming/machining step 608 may be omitted from the process. A wide variety of alternative implementations will be apparent to those of ordinary skill in the art, after having received the benefit of this disclosure.

Example 4

Figure 7:
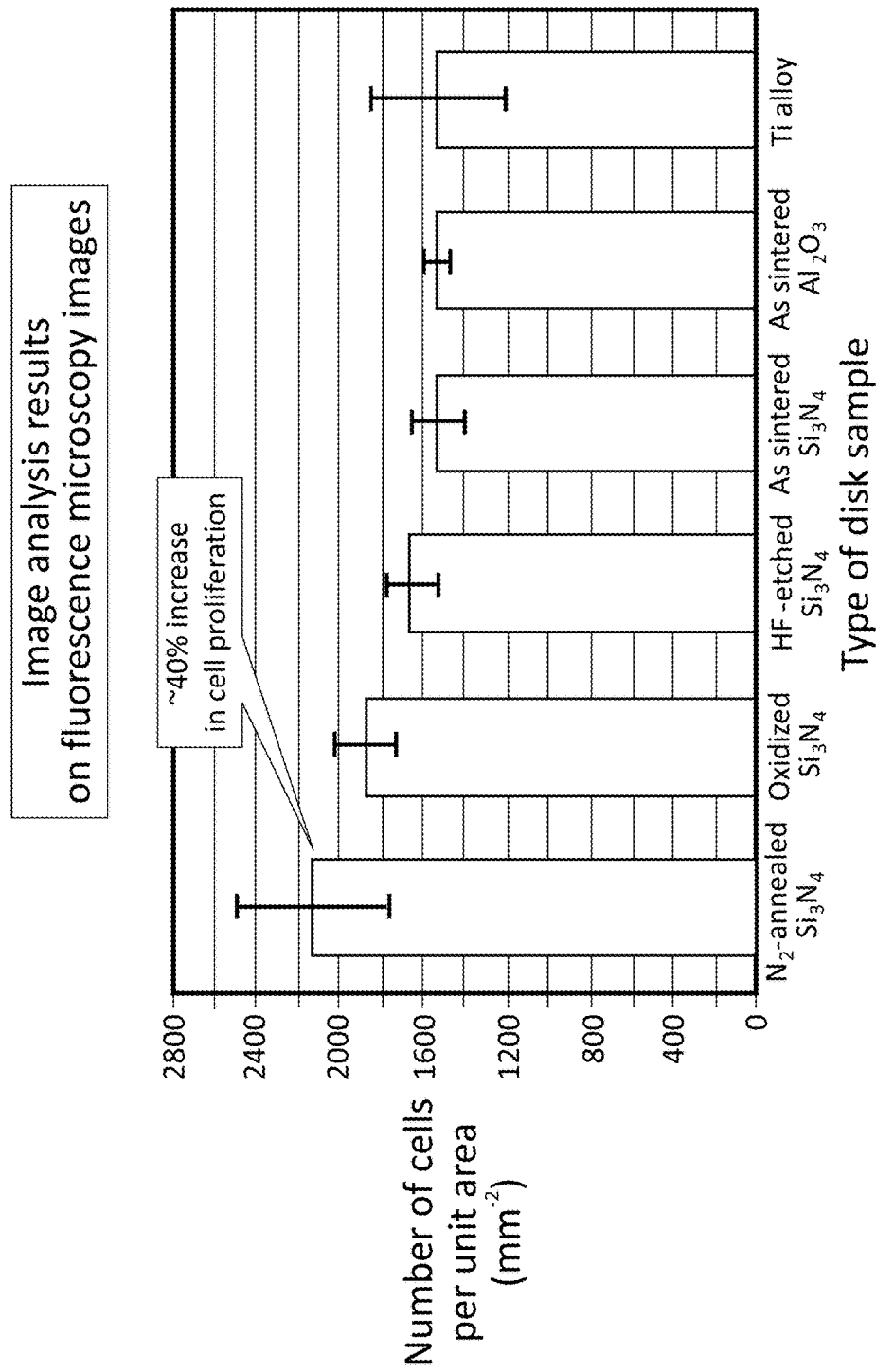
FIG. 7 is a graph illustrating the results of an image analysis on fluorescence microscopy images for various materials, some of which were treated in accordance with methods and principles disclosed herein.

In this study, an experiment was performed using Saos 2 osteosarcoma cells at $5 \times 10^4$ to $10^5$ concentrations. These cells were seeded onto a number of biomaterial samples. The samples were then incubated in 4.5 g/L glucose with L-Gin and sodium pyruvate supplemented with 10% fetal bovine serum and allowed to proliferate in a well plate (petri dish) for about 24 hours without addition of ascorbic acid (to suppress apatite formation). Subsequently, the cells were stained for fluorescence microscopy with Phalloidin and DAPI for the F-actin and nuclei, respectively. Cell counts were then performed for each of the samples, the results of which are shown in FIG. 7.

Various materials were prepared for this experiment as follows. Silicon nitride powder was mixed with yttrium oxide and aluminum oxide sintering aids and formed at room temperature into a green body. The green body was then sintered in a nitrogen atmosphere at a temperature of about 1700° C. to closed porosity and further densified by hot isostatic pressing at a temperature of at least about 1650° C. and at nitrogen gas pressures of about 138 MPa. The resulting silicon nitride exhibited a two-phase microstructure consisting of anisotropic β-silicon nitride grains separated by thin (less than about 2 nm) grain boundaries of amorphous or crystalline yttrium aluminum oxynitride or Si(Y)AlON, respectively.

The as-fired silicon nitride was divided into two groups. One group was sectioned into wafers (10 mm×10 mm×2 mm) with one major face left as-fired and the remaining faces ground flat using a 1000 grit diamond-impregnated wheel on a surface grinder. This sample group was designated "as-fabricated." The second group was sectioned into wafers of the same geometry with all six faces ground to the same finish. One of the major faces on each wafer was lapped using 6 μm diamond on a lapping machine, and subsequently polished using colloidal silica (Leco, St. Joseph, Mich.). This group was designated "as polished." Both wafer groups (as-fabricated and as-polished) were subjected to ultrasonic cleaning in deionized water of 17.5 MΩ·cm resistivity for about 30 minutes to remove contaminants. The wafers were then divided into sub-groups and subjected to the thermal and chemical treatments described below.

Samples were prepared with modified geometries for Raman spectroscopy, streaming potential, and wetting angle measurements. Rectangular plates with dimensions of 40 mm×20 mm×1 mm were used for streaming potential measurement, and circular discs having a diameter of about 12.7 mm and a thickness of about 3 mm were used for Raman spectroscopy and wetting angle determinations. Aside from deviations in dimensions, the preparation of all samples was identical.

One of the material samples was treated by wet chemical etching using hydrofluoric acid (HF). Since the removal rate of silicon dioxide tends to be significantly faster than that of silicon nitride, this allows for removal of the silicon dioxide passivation layer without significantly etching the underlying nitride. This treatment may therefore be helpful in increasing the concentration of amine groups at the surface by etching away the passivation layer, thus pushing the surface composition towards the nitride end of the nitride-oxide spectrum. These samples were immersed in a 5 wt. % HF solution for about 45 seconds, transferred into a continuously refreshed DI water bath for about 30 minutes, dried under a stream of filtered nitrogen, and then stored in a desiccator containing a hygroscopic media under a partial vacuum (about 100 Torr) to slow spontaneous re-oxidation.

Another material sample was treated with a thermal annealing treatment using nitrogen. It was hypothesized that re-exposing silicon nitride to a nitrogen atmosphere at high temperatures might increase the density of nitrogen in the transitional oxynitride layer. As a result, this heat treatment was seen as a potential alternative to the HF etching treatment or as a treatment to be applied in addition to the HF etching treatment.

The samples were placed in a batch furnace evacuated to about 250 mTorr, then back-filled with filtered nitrogen (about 1-2 psi) and subsequently heated to about 1400° C. for about 30 minutes.

Still another sample was treated with an oxidation treatment step. This treatment step was employed because it was hypothesized that it should completely oxidize the surface, yielding a maximum, or at least an increased, concentration of hydroxyl groups and pushing the surface composition towards the oxide end of the nitride-oxide spectrum. These samples were oxidized using an open-air kiln for about seven hours at about 1070° C.

The results of this example are shown in the graph of FIG. 7. As shown in this figure, each of the treatment steps/conditions described above was effective in improving osteoblast adhesion and proliferation, with the nitrogen annealing providing the most benefit. This was assessed by comparing the number of adherent cells on a substrate per unit area, which is a preferred method of assessing in vitro cell proliferation (and osteoconductivity). More specifically, the nitrogen-annealed silicon nitride exhibited an improvement of about 40% over the as-sintered silicon nitride, the as-sintered aluminum oxide, and a titanium alloy.

Although the treatment conditions were fixed for this experiment, it appears that a broad range of conditions and/or treatment steps may be useful for arriving at an ideal silicon nitride material in terms of osteoconductivity and/or antibacterial function. For example, in some embodiments and implementations, materials may be both nitrogen annealed and thermally oxidized. In some embodiments and implementations, the nitrogen annealing may be performed at a temperature of between about 1200° C. and about 1400° C., and/or may be performed for time periods from about 30 minutes to about 2 hours. The nitrogen pressure may range from ambient to about 207 MPa. For the thermally oxidized conditions, effective temperatures may vary from about 700° C. to about 1200° C. for time periods of between about 30 minutes and about 24 hours in ambient air.

As previously mentioned, silicon nitride materials prepared in this manner may be useful for a variety of purposes, including as monolithic biomedical implants, as coatings for biomedical implants or other medical products, as a matrix to dispersions of biocompatible materials, or as an additive or filler for biomedical implants made of polymers or other materials or other medical products, such as catheters.

Example 5

Figure 8:
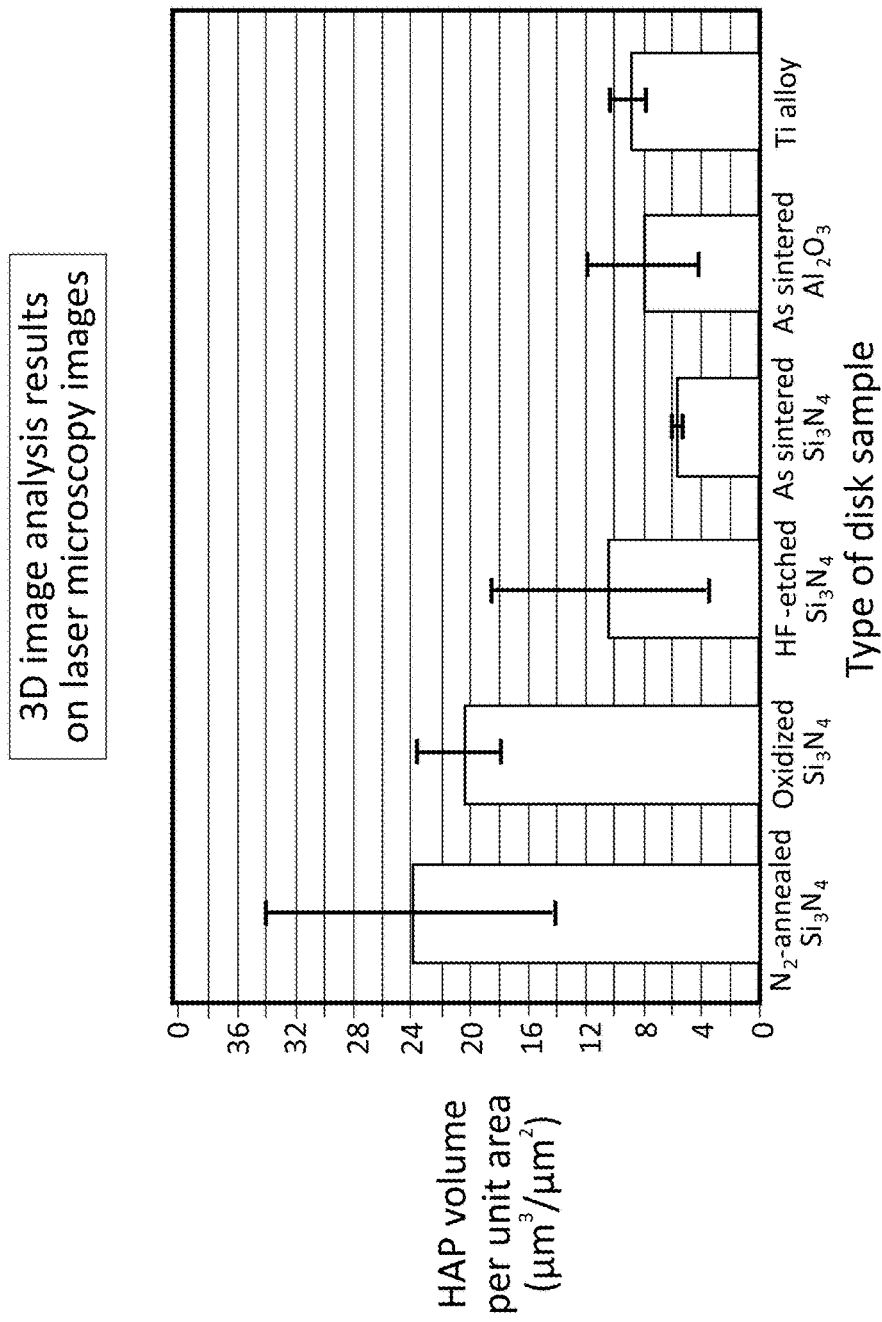
FIG. 8 is a graph illustrating the results of a 3D image analysis on laser microscopy images for various materials, some of which were treated in accordance with methods and principles disclosed herein.

In this study, an experiment was performed using Saos 2 osteosarcoma cells seeded onto various biomaterial disks at the same concentration as the experiment of Example 4. In this example, however, the seeding took place in an osteogenic medium which consisted of DMEM supplemented with about 50 μg/mL ascorbic acid, about 10 mM β-glycerol phosphate, about 100 nM dexamethasone, and about 10% fetal bovine calf serum. These samples were incubated for up to 7 days. Alizarin was used as a red fluorescence marker to identify $Ca^{2+}$ ions, which is an indicator of hydroxyapatite formation. Results were assessed by laser microscopy and 3D image analyses, and are shown in FIG. 8 in units of hydroxyapatite (HAP) volume per unit area ($\mu m^3/\mu m^2$). The same sets of materials used to obtain the results of FIG. 7 were used in Example 5 to obtain the results of FIG. 8.

As illustrated in FIG. 8, the experiments of Example 5 again demonstrated significant beneficial improvements with the materials treated in accordance with the inventive principles disclosed herein. More particularly, the osteoconductivity of silicon nitride increased by over 300% by applying the nitrogen annealing process compared to the as-sintered silicon nitride sample and the osteoconductivity of the oxidized silicon nitride sample was more than three times that of the as-sintered sample. The comparative results with respect to aluminum oxide were also quite dramatic. The oxidized silicon nitride sample demonstrated an increase in osteoconductivity of about 160% over the as-sintered aluminum oxide sample and the nitrogen annealed silicon nitride demonstrated an increase in osteoconductivity of about 190% over the as-sintered aluminum oxide sample.

Although the treatment methods in Examples 4 and 5 remained constant and were independently performed, various treatment combinations may provide synergistic additional benefits beyond those obtained by employing a single treatment method. For instance, sequentially performing thermal oxidation and high pressure and temperature nitrogen annealing may result in a significant increase in nitrogen concentration at the surface of the implant, which may result in an even more dramatic increase in certain desirable properties for biomedical implants, such as osteoconductivity and/or antibacterial characteristics.

In addition, as previously mentioned, although the treatment conditions were fixed, it appears that a range of such conditions may be effective in achieving one or more of the desirable outcomes referenced herein. For example, for a thermal oxidation process, the temperature may range from about 700° C. to about 1200° C. and may be performed for a duration ranging from about 30 minutes to about 24 hours. Similarly, for the nitrogen annealing process, the temperature may range from about 1200° C. to about 1400° C. for a duration of between about 30 minutes and about 2 hours. The pressure may be from about ambient to about 207 MPa. As mentioned, these two steps may be combined together in a sequential manner to obtain the desired material.

Another desirable combination of treatment steps may comprise a chemical etching treatment step, such as a HF treatment step (as described above). The same material may also undergo a nitrogen annealing step, as also described above.

Yet another desirable combination of treatment steps may comprise a chemical etching treatment step, such as a HF treatment step (as described above). The same material may also undergo a thermal oxidation process at a temperature of between about 700° C. and about 1200° C. for about 30 minutes to about 24 hours and a nitrogen annealing process at a temperature of between about 1200° C. and about 1400° C. for about 30 minutes to about 2 hours and at a pressure of between about ambient and about 210 MPa. However, it is expected that higher pressures may be more effective in achieving desirable results. Thus, in some embodiments and implementations, the annealing process may be performed at a pressure from about 100 MPa to about 210 MPa.

Another method for increasing oxidation, which may be combined with one or more of the other treatment steps described herein, may comprise using a relatively low volume fraction slurry (e.g., in some implementations, less than 10% by volume) of fine particles (preferably smaller than 500 nm in diameter; in some cases smaller than 100 nm in diameter). In some embodiments and implementations, these particles may comprise silicon nitride and theta, gamma, and/or alpha aluminum oxide ($Al_2O_3$), aluminum nitride (AlN), and/or yttrium oxide ($Y_2O_3$) particles, or possibly particles of compounds made from such materials, such as an yttrium aluminum garnet (YAG), yttrium silicates, aluminum silicates, and the like. In some such embodiments and implementations, these particles may be added in at least approximately the same composition as in the original monolithic ceramic. Thus, for example, in some embodiments and implementations, silicon nitride, aluminum oxide, aluminum nitride, and yttrium oxide particles may be added to replicate the monolithic silicon nitride batch composition of approximately 90% silicon nitride, 6% yttrium oxide and 4% aluminum oxide. Alternatively, it may be desirable to increase the amount of nitrogen in this oxynitride coating by utilizing a higher concentration of aluminum nitride particles. In this case, some embodiments and implementations may wholly substitute aluminum nitride for the aluminum oxide particles. Thus a surface coating can be prepared with a range of nitrogen contents. For instance, an oxynitride glass coating containing between about 5 to 10 atm. % nitrogen can be prepared, and/or a polycrystalline ceramic coating with nitrogen contents between approximately 10 atm. % to 60 atm. % nitrogen can also be formed.

Then, one or more of the various firing conditions described above may be employed to effectively adhere and/or glaze the surface of the material in a thin layer of silicon-yttrium-aluminum-oxynitride (SiYAlON) polycrystalline ceramic and/or glass. This SiYAlON layer may have numerous benefits, including antibacterial function and promoting osteoconductivity.

This may yield near-complete SiYAlON coverage to an even greater degree than the nitrogen heat treatment alone. Another benefit of this approach is that it may lend itself well to doping/composition adjustment, such as adding silica ($SiO_2$) to modify the surface composition if needed and/or other additives, such as phosphoria, calcium orthophosphates, hydroxyapatite, and/or various bioglasses (e.g., 45S5 bioglass) to further increase bioactivity. In some embodiments and implementations, other traditional bioglass constituents may be added to give the surface a hybrid bioglass-oxynitride composition.

In some embodiments and implementations, alumina may be excluded to instead give the surface a silicon yttrium oxynitride (SiYON) composition. In some embodiments and implementations, elements from the lanthanide series, such as lanthanum, cerium, praseodymium, neodymium, samarium, gadolinium, ytterbium, and/or lutetium, may be included, usually in the form of their respective oxides and/or nitrides, in lieu of or in conjunction with the yttrium constituent. In fact, it is thought that, for some applications, it may be preferred to substitute lanthanides for yttrium to yield similar crystalline phases. Such replacements may provide certain benefits for certain applications, such as more desirable charging behavior, superior stability of a desired phase, and/or more ideal lattice parameter of a desired phase. In some embodiments and implementations, it is expected that calcium may be a suitable replacement, in lieu of or in conjunction with the yttrium constituent.

Similarly, in some embodiments and implementations, scandium may also be included, usually in the form of its respective oxide and/or nitride, in lieu of or in conjunction with the yttrium constituent. In some embodiments and implementations, boron may also be included, usually in the form of its respective oxide and/or nitride, in lieu of or in conjunction with the silicon constituent.

It appears that the SiYAlON glass, and/or a SiYON glass, may be an important reason for providing substantial benefits over other silicon nitride materials (referred to herein as "as-fired" silicon nitride). Moreover, although this SiYAlON glass is on numerous occasions referred to herein as appearing on the surface of the material as a "glaze" or "layer," it should be understood that the resultant SiYAlON glass may instead be formed separate from silicon nitride. This may be accomplished by mixing and firing the individual compounds or precursors that comprise the SiYAlON glass. For instance, silica ($SiO_2$), yttria ($Y_2O_3$) and aluminum nitride (AlN) can be mixed as powders and then fired, preferably at temperature above about 1400° C., to form the SiYAlON glass material. In some embodiments and implementations, yttrium nitride, and/or aluminum oxide, or one or more phases containing such materials, may be used to arrive at a suitable SiYAlON composition. In certain embodiments, SiYAlON may not be a specific formulation, but can vary across a composition range defined by the formula $Si_{3-3(m+n)/4}Al_m Y_n O_x N_{4-2x/3}$. In some embodiments, SiYAlON may have a composition with average m, n, and x values equal to or approximately 0.051, 0.021, and 0.166, respectively. The resulting glass can then be crushed back to an aggregate powder and used as a glaze or filler on a separate material and incorporated into other materials, such as by application of coatings, particulates, or use as a filler. In some embodiments and implementations, the SiYAlON glass monolith itself may be used as a scaffold for creating other structures, such as porous structures having a SiYAlON glass scaffold, for example.

Similarly, with respect to SiYON glasses, the individual compounds or precursors that comprise the SiYON glass can be mixed and/or fired. For instance, silica ($SiO_2$), yttria ($Y_2O_3$), silicon nitride ($Si_3N_4$) (or, as mentioned above, lanthanides and/or scandium in lieu of, or in addition to, the yttria) can be mixed as powders and then fired, preferably at temperature above about 1400° C., to form the SiYON glass material. In some embodiments and implementations, other compounds containing such materials may be used to arrive at a suitable SiYON composition. In some embodiments, the SiYON designation may not be a stoichiometric formula, but may represent a range of compositions in accordance with the following general formula: $Si_{3-3n/4}Y_nO_xN_{4-2x/3}$. The nitrogen in the SiYON material may be derived from, for example, yttrium nitride (YN) and/or silicon oxynitride ($Si_2N_2O$). The resulting glass or glass/ceramic body/monolith can then be crushed back to an aggregate powder and used as a glaze or filler on a separate material and incorporated into other materials, such as by application of coatings, particulates, or use as a filler. In some embodiments and implementations, the SiYON monolith itself may be used as a scaffold for creating other structures, such as porous structures having a SiYON scaffold, for example.

As another method for increasing the nitrogen content of the transitional oxide surface layer of the material, the silicon nitride or other ceramic material may be subjected to high-energy nitrogen implantation using an ion gun. In this manner, nitrogen ions may be sub-planted into the surface of the transitional oxide layer, resulting in a significant increase in nitrogen content and resultant benefits. Although possibly useful for other ceramic materials, this technique may be particularly applicable to silicon nitride coated implants. This is because, in some embodiments and implementations, the same or similar equipment used to place down an adherent silicon nitride coating can also be used to increase the nitrogen content of the surface of this coating through ion implantation.

After having received the benefit of this disclosure, there may be other possible methods for increasing the silanol content at the surface and/or the nitrogen content within the transitional oxide layer beyond those examples specifically described herein that may be apparent to those of ordinary skill in the art. Thus, any number of applicable techniques may be used to improve the osteoconductivity and/or antibacterial characteristics of ceramic materials, such as particularly monolithic silicon nitride ceramic materials, silicon nitride coatings, silicon nitride particulates, silicon nitride matrices, silicon nitride fillers, and/or SiYAlON coatings, additives, fillers, etc.

Based upon these principles and techniques, the fundamental characteristics of an ideal silicon nitride or other ceramic material having improved osteoconductivity, improved antibacterial function, and/or other desired characteristics, may include, for example, one or more of the following:

In some materials, the water wetting angle (as measured by sessile drop techniques) of the material may be less than about 30 degrees. In some such materials, the water wetting angle may be less than 30 degrees. In some such materials, the water wetting angle may be less than about 20 degrees. In some such materials, the water wetting angle may be less than 20 degrees. In some such materials, the water wetting angle may be less than about 10 degrees. In some such materials, the water wetting angle may be less than 10 degrees.

In some silicon nitride materials, the ratio in concentration of silicon nitride surface and/or transitional oxide layer defects possessing a net positive charge, as measured by cathodoluminescence spectroscopy, may be between about 100% and about 400% or greater than "as-fired" silicon nitride without having undergone the treatment steps and processes disclosed herein. In some such embodiments and implementations, the ratio in concentration of silicon nitride surface and/or transitional oxide layer defects possessing a net positive charge, as measured by cathodoluminescence spectroscopy, may be between about 150% and about 400% greater than "as-fired" silicon nitride without having undergone the treatment steps and processes disclosed herein.

More generally, the processes and materials described herein may be used to, for example, change the surface chemistry of silicon nitride and/or other ceramics to increase the silanol content at the surface and/or nitrogen content in the transitional oxide layer through annealing of dense material in a high nitrogen environment at modest to high temperatures and pressures. This change may result in the immediate surface becoming more negatively charged, with the subsurface transitional oxynitride layer becoming more positively charged, having a higher concentration of negatively charged silanol groups at the immediate surface, and/or positively charged amine groups within the transitional oxynitride layer.

The processes and materials described herein may also be used to, for example, change the surface chemistry of silicon nitride and/or other ceramics to increase the available nitrogen in the transitional oxide layer by thermal oxidation of the transitional oxide layer.

The processes and materials described herein may also be used to, for example, change the surface chemistry of silicon nitride or other ceramics to increase silanol groups immediately at the surface and/or increase the available nitrogen in the transitional oxide layer by subjecting the implant to etching using various acids or caustic bases.

The processes and materials described herein may also be used to, for example, change the surface chemistry of silicon nitride or other ceramics by forming a polycrystalline and/or glass coating consisting of high-nitrogen content SiYAlON or SiYON, as mentioned above. In some embodiments, the nitrogen content in the SiYAlON or SiYON coating/surface/glaze may be between about 5 atm. % and 60 atm. %. In embodiments comprising an N-apatite ($Y_5Si_3O_{12}N$), as discussed below, the nitrogen content may be slightly less that 5 atm. %, such as between about 4 atm. % and about 5 atm. %. As previously described, such materials may be used to form monolithic implants having the glass along at least a portion, or the entire, surface of the material. Alternatively, the SiYAlON/SiYON glass itself may be formulated and prepared separate from the silicon nitride and used as a filler, coating, or otherwise incorporated into other implants or materials.

In addition, ion-implantation of an intermediate layer has been unexpectedly discovered as a method of improving the adhesion of silicon nitride coatings. In turn, this improvement should lead to better wear performance.

The processes and materials described herein may also be used to, for example, produce a surface composition with a higher N/Si and/or lower O/Si ratios than as-fabricated and/or as-fired materials. For example, in some embodiments and implementations, the N/Si ratio may range from about zero to about 1.22 and the O/Si ratios may range from about 0.15 to about 1.76.

Thermal treatment in nitrogen may produce a surface coated in crystalline β-Si(Y)AlON precipitates. In some such materials, the concentration of these precipitates may decrease as a function of depth, in some cases up to about 90 μm. This treatment condition exhibited extreme hydrophilicity. Thermal treatment in an oxidizing atmosphere may produce a surface composition effectively the same as amorphous silicon dioxide. This step may also lead to material with an extremely low wetting angle mimicking pure silica.

One or more of the materials produced in accordance with the methods disclosed herein may also have an isoelectric point with decreasing O/Si atomic ratio and with increasing N/Si atomic ratio, as the surfaces transition from resembling pure silicon dioxide to pure silicon nitride.

Both of the thermal treatments disclosed herein (i.e., oxidation and nitrogen annealing) may offer interesting advantages for orthopedic implants due to their observed extreme hydrophilicity. The significant increase in the hydrophilicity for the oxidized material may lead to an enhancement of the bacteriostatic and osteointegrative behavior properties over what has already been observed for untreated silicon nitride materials. Further, the surface chemistry of silica is well-understood, lends itself to manipulation, and has already been shown to be an ideal scaffold for bone on-growth.

X-ray photoelectron spectroscopy data indicates that thermal, mechanical, and/or and chemical treatments, as disclosed herein, may produce significant changes in surface chemistry, producing a wide range of nitride/oxide atomic ratios, and increased concentration of oxides at the material's surface. Within a depth of up to at least about 2-3 nm, the surface composition of untreated silicon nitride used in Examples 4 and 5 above had N/Si and O/Si atomic ratios of 1.01 and 0.49, respectively, which appears to be silicon oxynitride ($Si_2N_2O$), indicating the surface is partially-oxidized. There is likely a gradient in chemical composition, with decreasing oxygen away from the surface, as found for oxidized silicon nitride films. In addition, minor amounts of Al and Y were also detected by XPS. Some of the oxygen on the surface is obviously bound to these elements instead of Si.

Etching of this silicon nitride material in HF resulted in dissolution of this thin oxynitride layer. However, the etched surface may re-oxidize in air at room temperature, resulting in an oxide or oxynitride layer which increases in thickness over time. When compared to as-fired (untreated) silicon nitride, the HF-etched surface showed higher N/Si and lower O/Si ratios.

Thermal oxidation of as-fired/untreated monolithic silicon nitride resulted in a surface composition corresponding to silicon dioxide. The amount of Al and Y, resulting from the intergranular phase, was also much higher than the as-fired/untreated silicon nitride. In addition, x-ray diffraction data suggests the formation of $Yi_2SiAlO_5N$ (hexagonal) at the surface of these samples. It is thought that this is formed due to the oxidation of the silicon nitride grans and by aluminum and yttrium diffusing from the SiYAlON intergranular phase into the surface oxide layer at high temperature during the oxidation treatment. By contrast, the surface composition of the silicon nitride thermally treated in nitrogen showed little difference in N/Si and O/Si ratios from the as-fired material, likely due to the thermal stability of the oxynitride layer in dry nitrogen. The phase chemistry may, at least in part, promote the osteoconduction and bacteriostasis of the material. The presence of $Yi_2SiAlO_5N$ in the body of the ceramic may contribute to its improved performance.

The surface treatments disclosed herein also had a profound influence on surface charging. Chemical/mechanical polishing of as-fired samples increased their isoelectric point from about 4.2 to about 5.5. The principle differences between as-fired and polished surfaces are: (1) An increase in exposed intergranular phase relative to grains; and, (2) A reduction in oxide layer thickness on the exposed grains. The intergranular phase is expected to exhibit a relatively high isoelectric point. Further, the reduction in the passivation layer thickness may produce a more nitride-like surface, leading to an increase in the concentration of amine sites. Both of these changes are expected to shift the IEP higher, as was observed in the Examples.

When the surfaces of the samples were oxidized, the result was a large shift in isoelectric point towards pure silicon dioxide (pH 2). It is thought that this behavior can be correlated with the N/Si and O/Si atomic ratios determined from the XPS data and a broad peak corresponding to amorphous silica in the Raman spectrum. Decreased O/Si and increased N/Si ratios increases the isoelectric point. It is expected that the number of silanol groups correlates with the O/Si ratio, and the number of amine sites correlates with the N/Si ratio.

It is also noteworthy that silicon nitride exhibits a negative surface charge at homeostatic pH, but changes in surface charge by oxidation or by annealing in nitrogen may accelerate apatite deposition and osteoblast adhesion for use in certain biomedical implants.

Furthermore, modulation of the surface charge on silicon nitride at physiologic pH could contribute to the observed bacteriostatic behavior of silicon nitride. Thus, the treatments disclosed herein may further allow for customization of silicon nitride materials that have a desired combination of osteoconductivity and bacteriostatic characteristics.

It is also worth noting that the three intense Raman Spectroscopy bands (located at 180.1, 201.4 and 234.5 $cm^{-1}$ in the as-fired sample) was observed in the Raman spectra of all samples used in various experiments and represent the E2g, Ag, and E1g vibrational modes of the skeletal Si—N bonds in the $β-Si_3N_4$ structure, respectively.

These results are shown in FIGS. 9a-9d. As illustrated in these figures, the as-fabricated and HF-treated samples presented quite similar Raman spectra. However, the HF treatment reduced the relative intensity of the Ag band with respect to the E2g and E1g bands, whose relative intensity instead remained unchanged. It is thought that this variance can be attributed to differences in crystallographic orientation of the surface crystallites irradiated by the incoming polarized laser. The morphological changes observed in the Raman spectrum collected from the sample thermally treated in nitrogen (FIG. 9c) were by far more drastic.

Indeed, one can still observe the original triplet belonging to the untreated sample, but also an additional triplet, significantly broadened and markedly shifted toward lower emission frequencies, could be observed. The sample treated in air (FIG. 9d) did not show this additional (shifted) triplet. However, it also showed distinct differences as compared to the untreated sample, as follows: (a) Besides a clear decrease in the absolute intensity of all bands constituting the triplet, the trend of relative intensities was inverted as compared to the untreated sample, with the intensity order becoming E2g<Ag<E1g; (b) Some broadening could be observed, but the spectrum could yet be deconvoluted into the main triplet of the untreated sample overlapped to a quite broad emission centered at approximately 230 cm$^{-1}$. This broad band can be interpreted as a low-frequency component of the overall broad Raman emission of silica glass; and, (c) A small shift toward lower frequencies of the triplet could be found as compared to the standard positions recorded in the untreated sample.

Figure 9A:
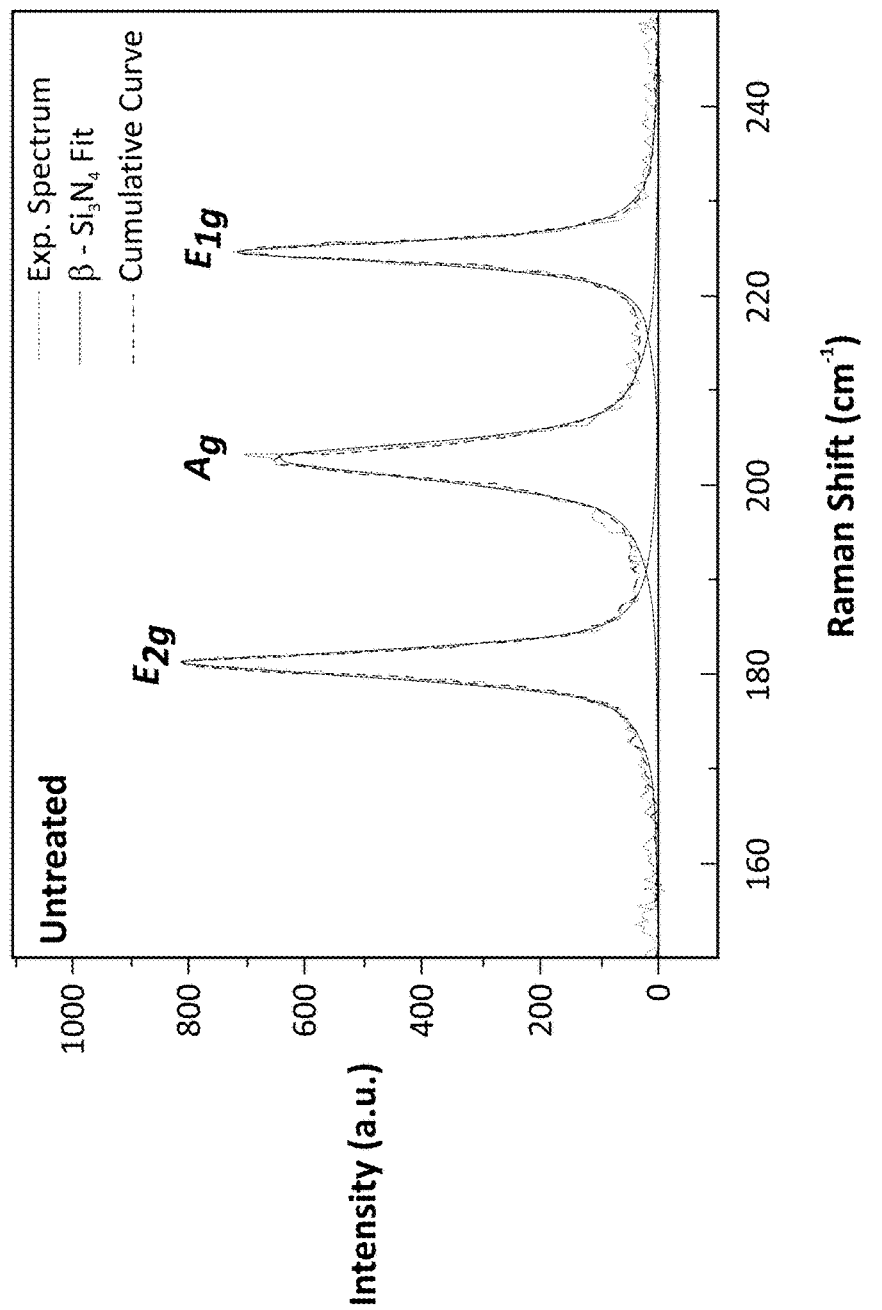
FIG. 9a is a graph illustrating Raman spectra of an untreated silicon nitride surface in the 150-250 cm region.
Figure 9B:
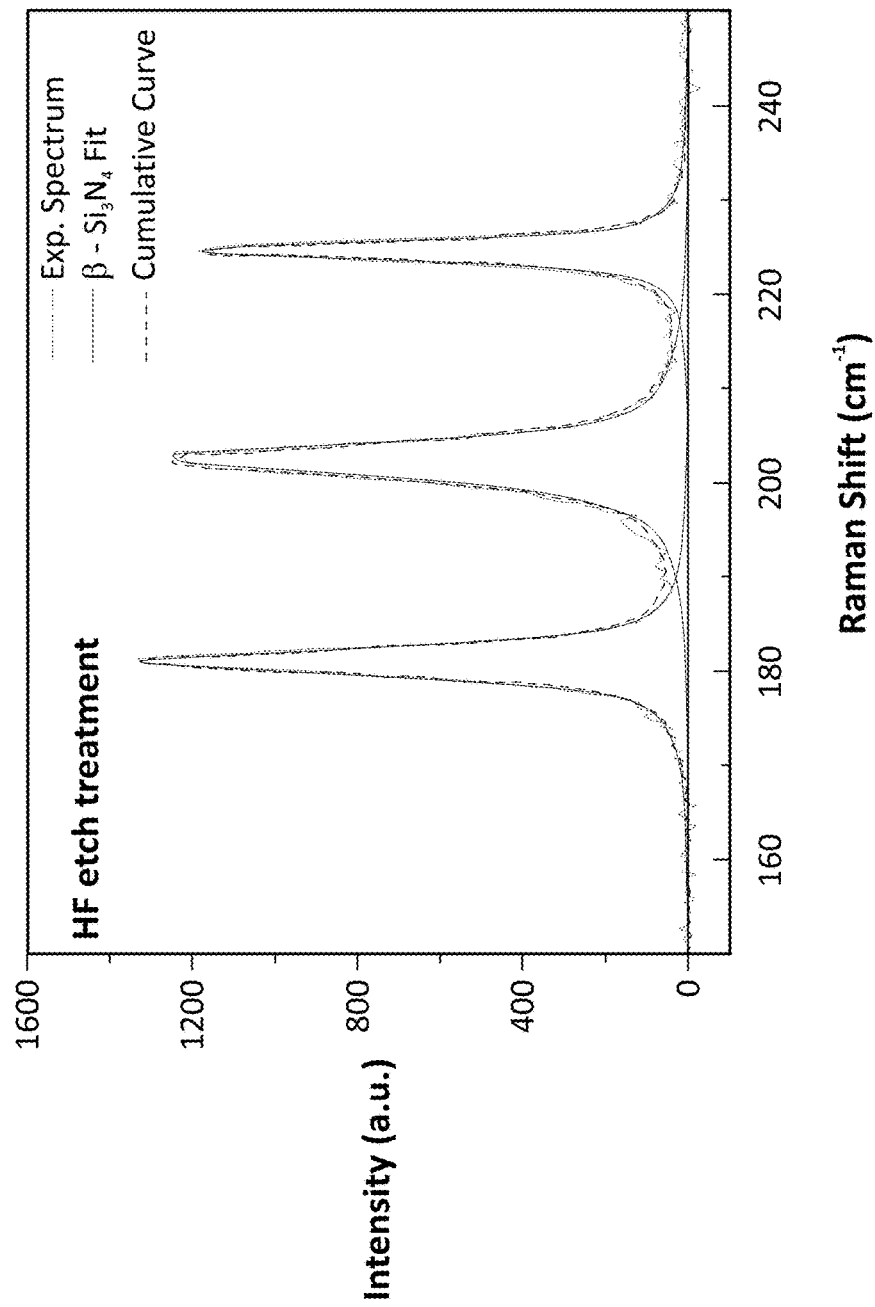
FIG. 9b is a graph illustrating Raman spectra of a silicon nitride surface etched in hydrofluoric acid.
Figure 9C:
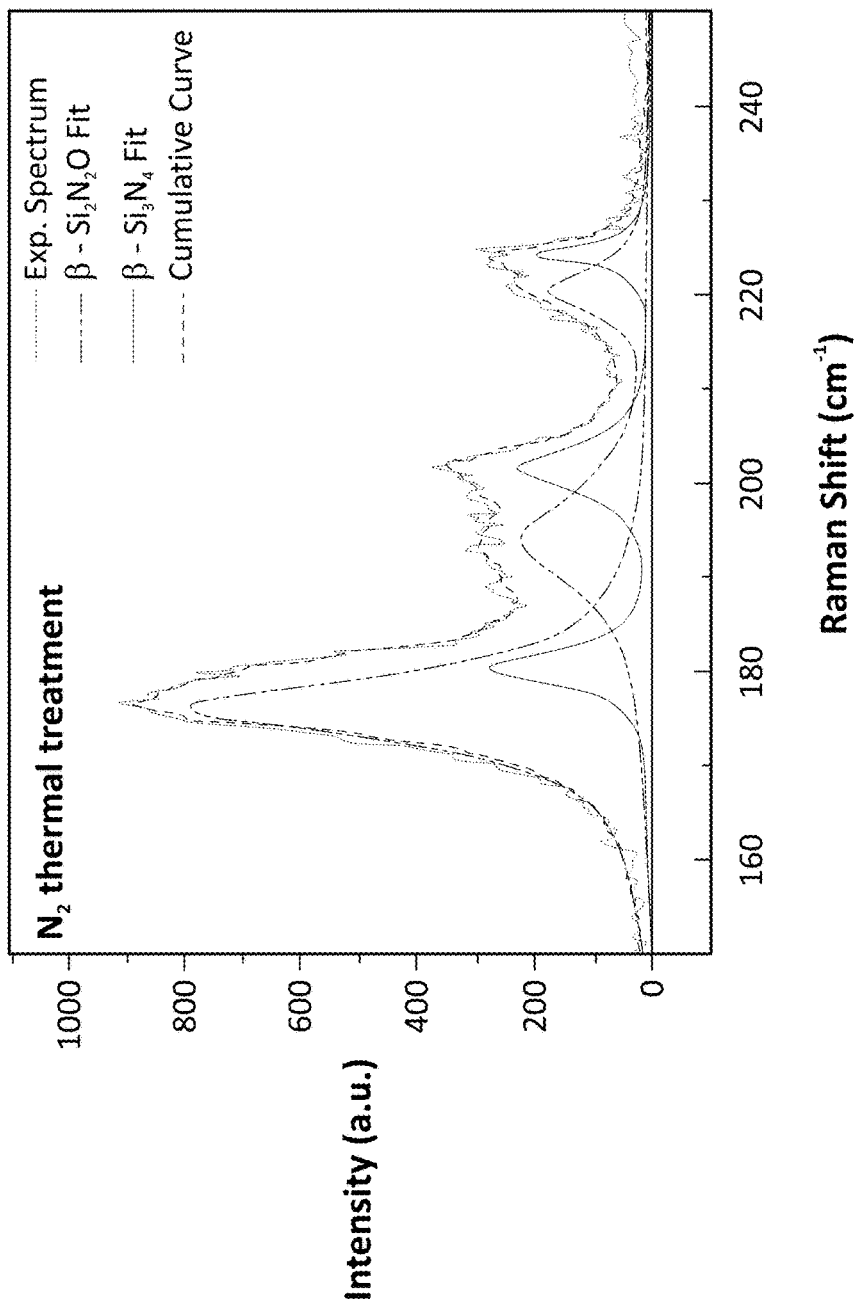
FIG. 9c is a graph illustrating Raman spectra of a silicon nitride surface treated in nitrogen.
Figure 9D:
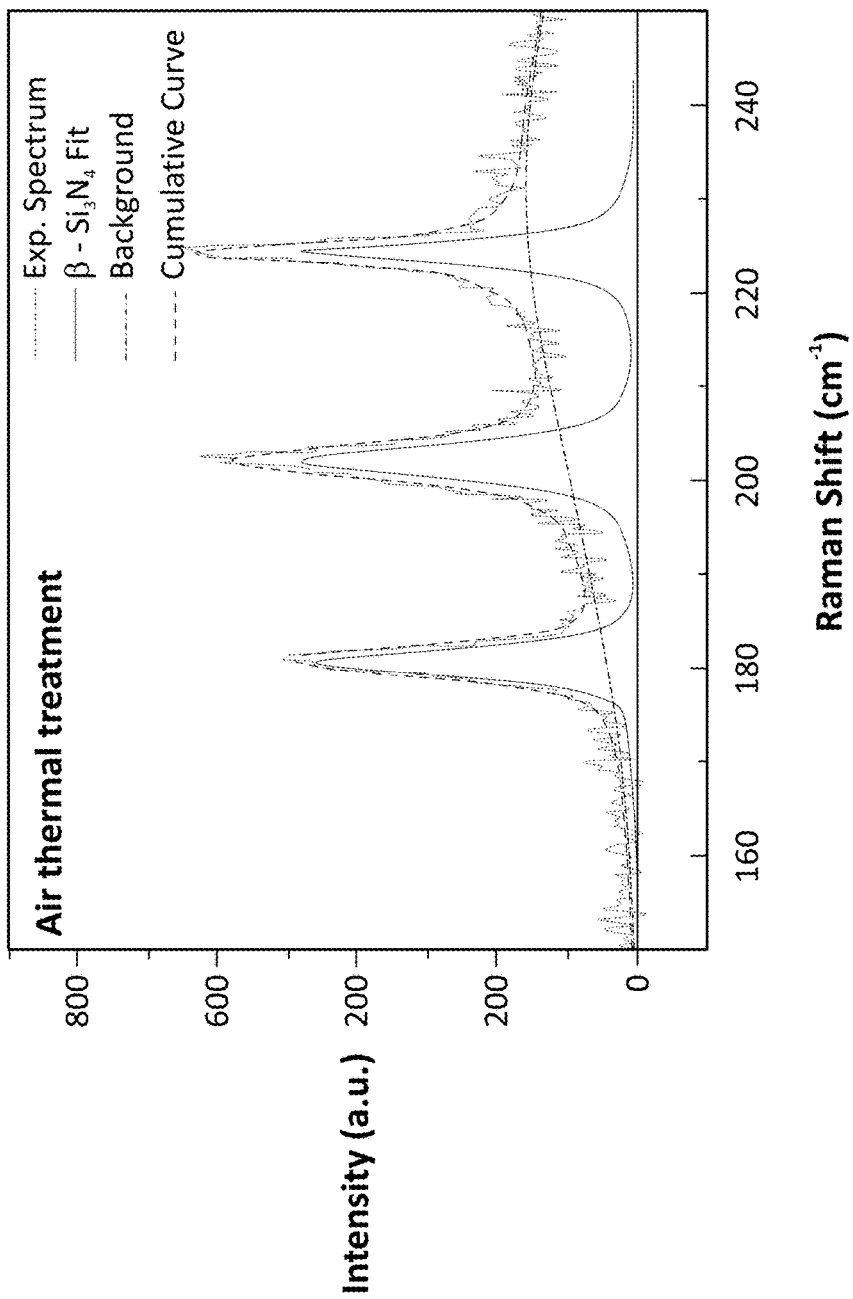
FIG. 9d is a graph illustrating Raman spectra of a silicon nitride surface treated in air.

The doubled triplet in FIG. 9*b* should be assigned to a form of β-Si(Y)AlON, as also suggested by XPS analyses. For this material, XPS analyses revealed N/Si and O/Si atomic ratios which correspond to silicon oxynitride ($Si_2N_2O$) and also the highest amount of Al and Y among the set of examined samples. According to Raman and microscopy findings, annealing in a nitrogen-rich environment promoted the re-growth of a surface layer of off-stoichiometric β-Si(Y)AlON, a newly formed compound responsible for the observed (shifted and broadened) Raman triplet. It appears that this process may not equally take place for the sample annealed in air, in which only an external glassy layer formed with a composition including, according to XPS, smaller amounts of Al and Y, and with a Raman spectrum close to that of silica glass.

Without being limited by theory, it appears from the examples that the preferred treatment conditions to obtain a monolithic silicon nitride ceramic or coating exhibiting improved osteoconductive and bacteriostatic properties may include, in some implementations, annealing in nitrogen, preferably at between about 1200° C. and about 1400° C. preferably for periods of between about 30 minutes and about 2 hours and under preferably under nitrogen pressures ranging between ambient to about 210 MPa, and more preferably at between about 1200° C. and about 1300° C. for time periods of between about 30 minutes to about 1 hour, and at nitrogen pressures of between about 100 to about 210 MPa, and most preferably between about 1200° C. and about 1250° C. for about 30 minutes to about 1 hour and at pressures of between about 100 and about 150 MPa.

A possibly less effective, but still preferred treatment from the foregoing examples is to thermally oxidize the monolithic silicon nitride in air at temperatures between about 700° C. and about 1500° C. for time periods ranging between about 30 minutes and about 24 hours, and more preferably between about 900° C. and about 1100° C. for time periods ranging between about 5 and about 12 hours, and most preferably at temperatures between about 1000° C. and about 1100° C. for time periods ranging between about 5 and about 10 hours. The effectiveness of these treatments can be characterized using XPS and cathodoluminescence spectroscopy as set forth in the foregoing examples. In addition, as previously mentioned, in some embodiments and implementations, both the annealing and oxidation steps may be consecutively utilized, as referenced above.

Figure 10:
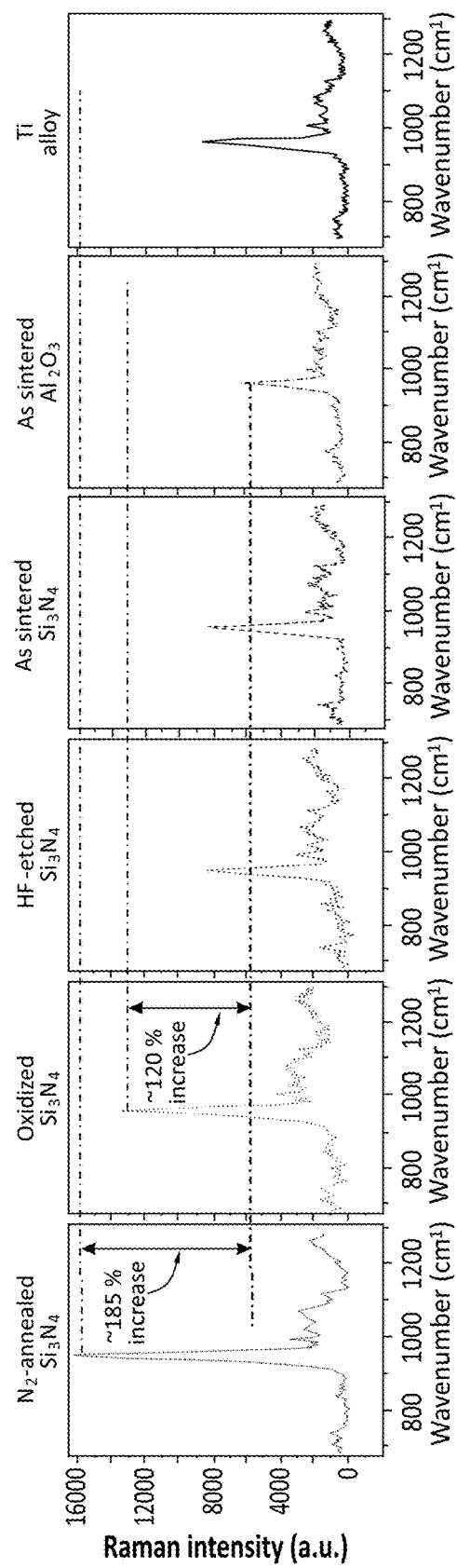
FIG. 10 is a series of graphs illustrating the results of a statistical analysis by Raman spectroscopy using various materials, some of which were treated in accordance with methods and principles disclosed herein.

FIG. 10 is a series of graphs illustrating the results of a statistical analysis by Raman spectroscopy using various materials. These graphs demonstrate a substantial increase in Raman intensity of the hydroxyapatite band for materials treated in accordance with methods and principles disclosed herein. The increase appears to be most pronounced in the silicon nitride sample manufactured using the nitrogen annealing process described above.

Figure 11:
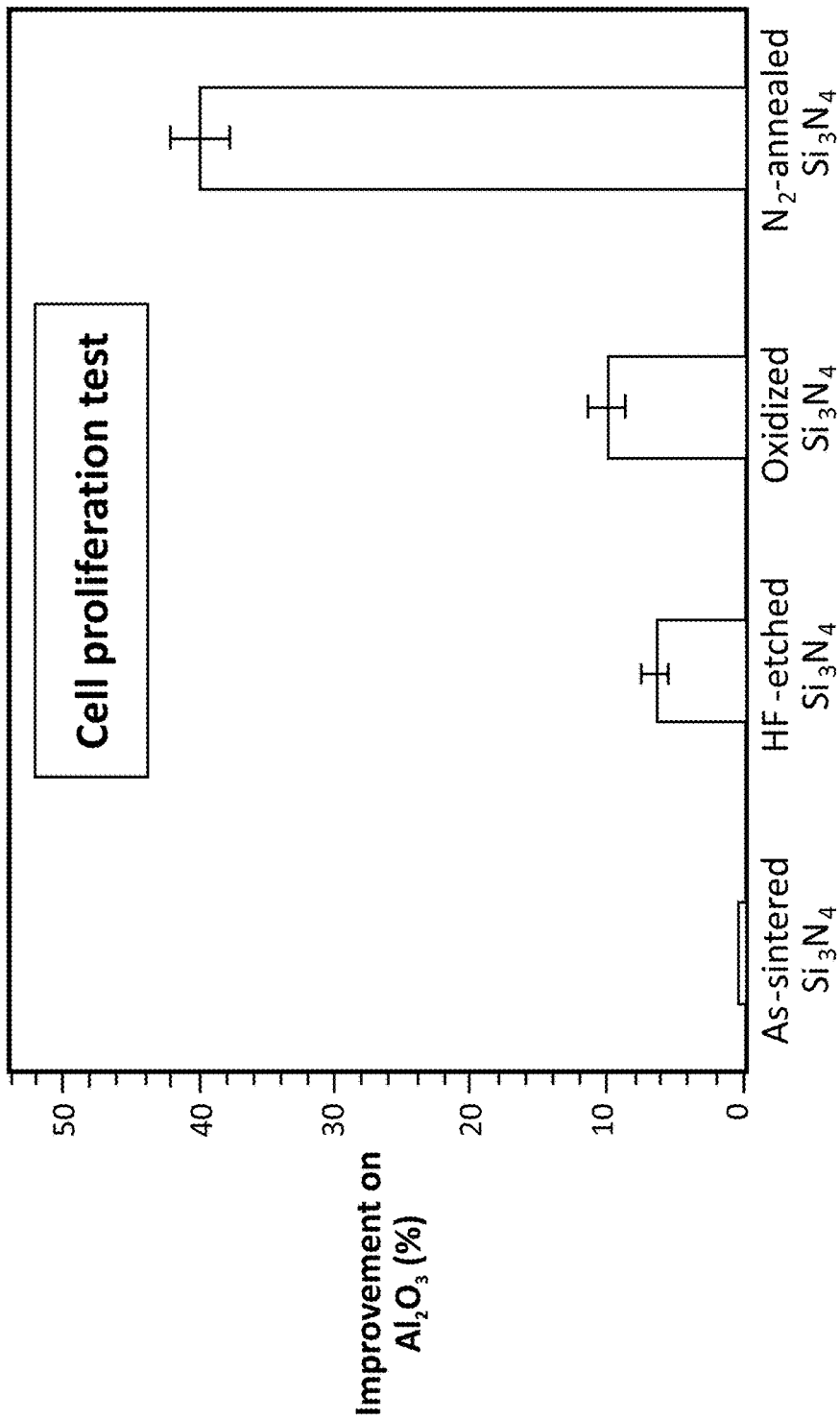
FIG. 11 is a graph illustrating the results of a cell proliferation test on various materials, some of which were treated in accordance with methods and principles disclosed herein.

FIG. 11 is a graph illustrating the results of a cell proliferation test on various materials as compared to an alumina sample. These results demonstrate a substantial improvement in osteosarcoma cell proliferation for the silicon nitride materials made using the inventive principles disclosed herein over the alumina sample. The silicon nitride sample manufactured using the nitrogen annealing process described above achieved the greatest such improvement.

Figure 12:
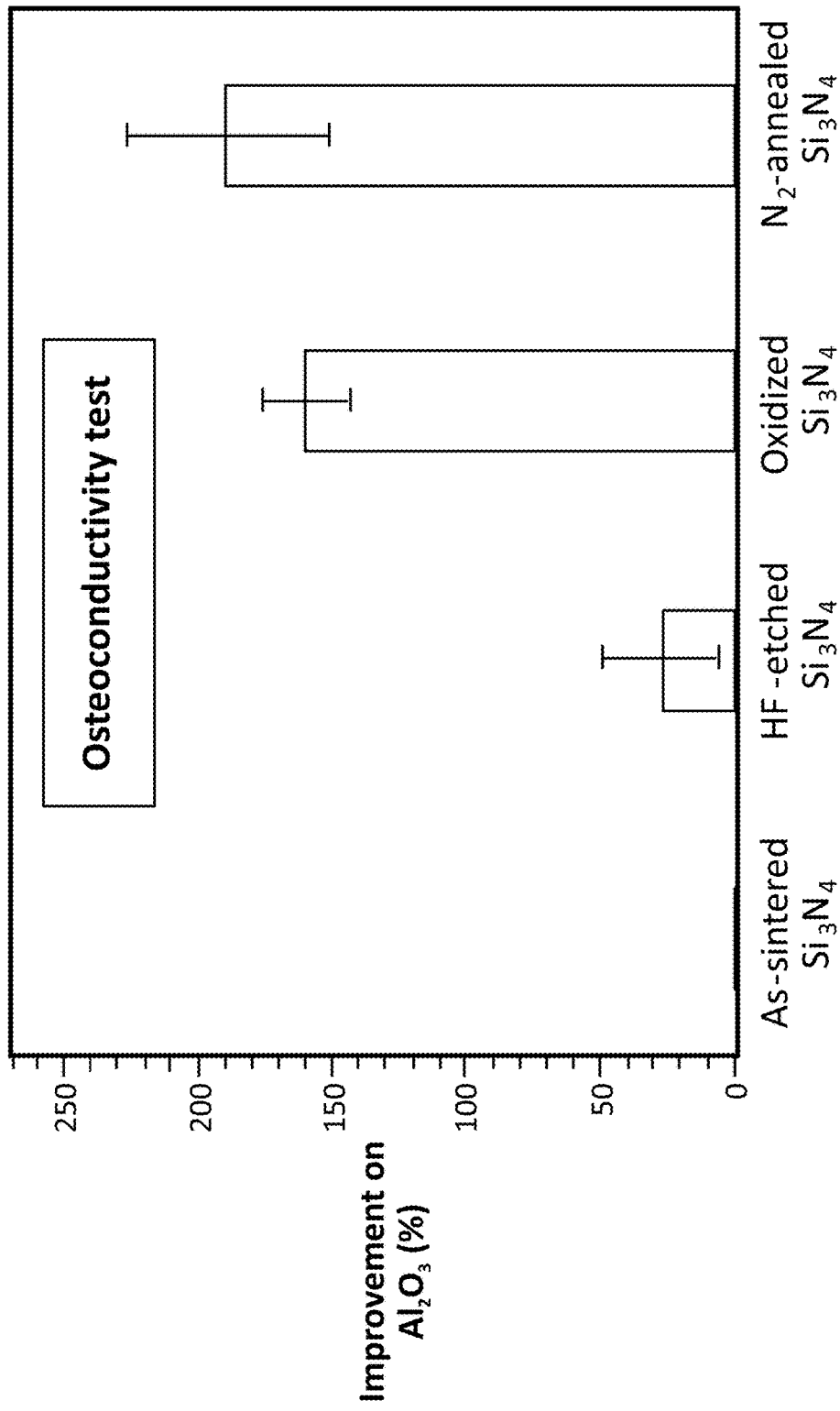
FIG. 12 is a graph illustrating the results of an osteoconductivity test using various materials, some of which were treated in accordance with methods and principles disclosed herein.

FIG. 12 is a graph illustrating the results of an osteoconductivity test using various materials as compared to an alumina sample. These results similarly demonstrate a substantial improvement in osteoconductivity for the silicon nitride materials made using the inventive principles disclosed herein over the alumina sample. Although both the oxidized and nitrogen-annealed silicon nitride samples both realized a very substantial improvement in osteoconductivity, the nitrogen-annealed silicon nitride samples realized the greatest improvement of nearly 200% over alumina.

Figure 13:
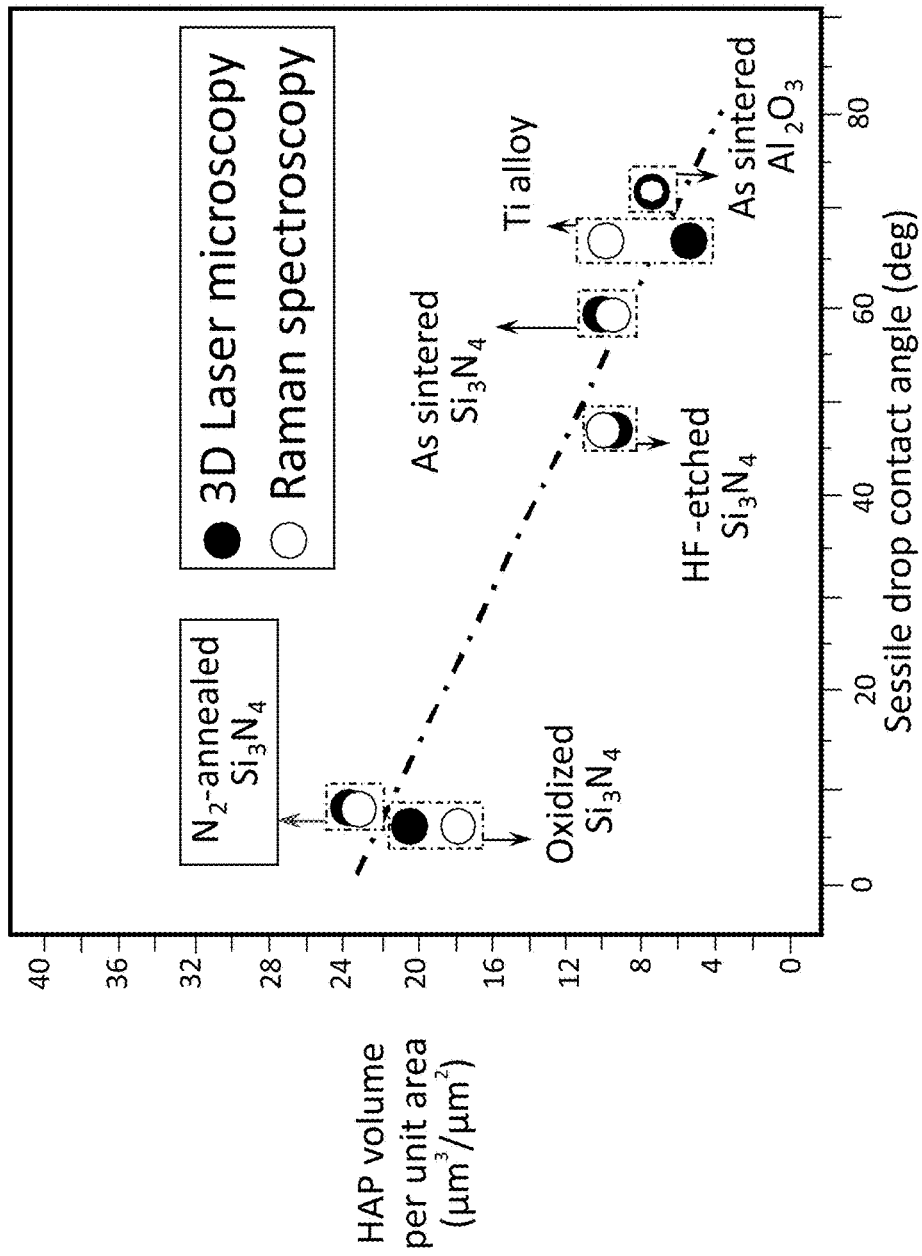
FIG. 13 is a graph illustrating the relationship between surface wettability and osteoconductivity for various materials, some of which were treated in accordance with methods and principles disclosed herein.

FIG. 13 is a graph illustrating the relationship between surface wettability (as measured by the sessile drop contact angle) and osteoconductivity (as measured by HAP volume per unit area) for various materials. The HAP volume measurements were separately taken using 3D Laser microscopy and Raman spectroscopy, as also illustrated in the graph. The graph of FIG. 13 demonstrates that the wettability of silicon nitride, which, as mentioned above, typically already has a relatively high wettability, may be increased substantially by applying one or more of the inventive methods/principles disclosed herein. In particular, the nitrogen-annealed and oxidized silicon nitride samples demonstrated the largest drop in sessile drop contact angle, and therefore the highest increase in wettability.

Figure 14:
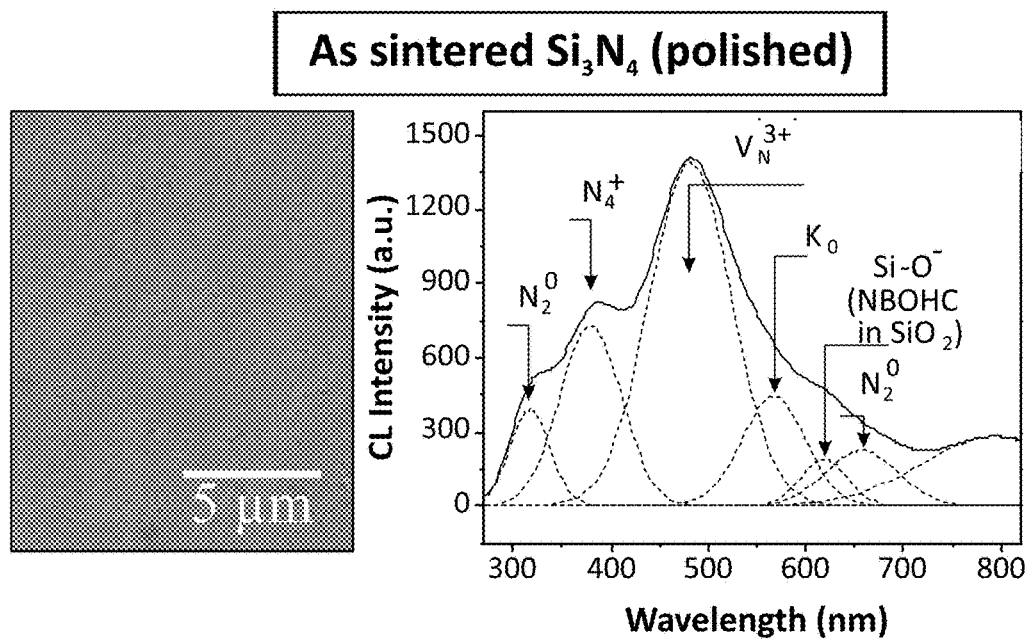
FIG. 14 is a graph illustrating the results of a cathodoluminescence spectroscopy analysis for an as-sintered and polished silicon nitride material.

FIG. 14 is a graph illustrating the results of a cathodoluminescence spectroscopy analysis for an as-sintered, polished silicon nitride material before treatment. This analysis, along with those of FIGS. 15-17 discussed below, was performed under exactly the same experimental conditions for all samples and made by the same operator. This data, which were confirmed by three separate sessions of experiments, illustrate the surface stoichiometry, and surface charge, of the material. In these figures, the statistical population of positively and negatively charged defects is visualized by the cathodoluminescence intensity, the intensities of the shown (Gaussian deconvoluted) sub-bands being directly proportional to the concentration of each particular. It is thought that the surface stoichiometry and surface charge have a strong bearing on desirable material characteristics, such as antibacterial function and/or osteoconductivity.

Figure 15:
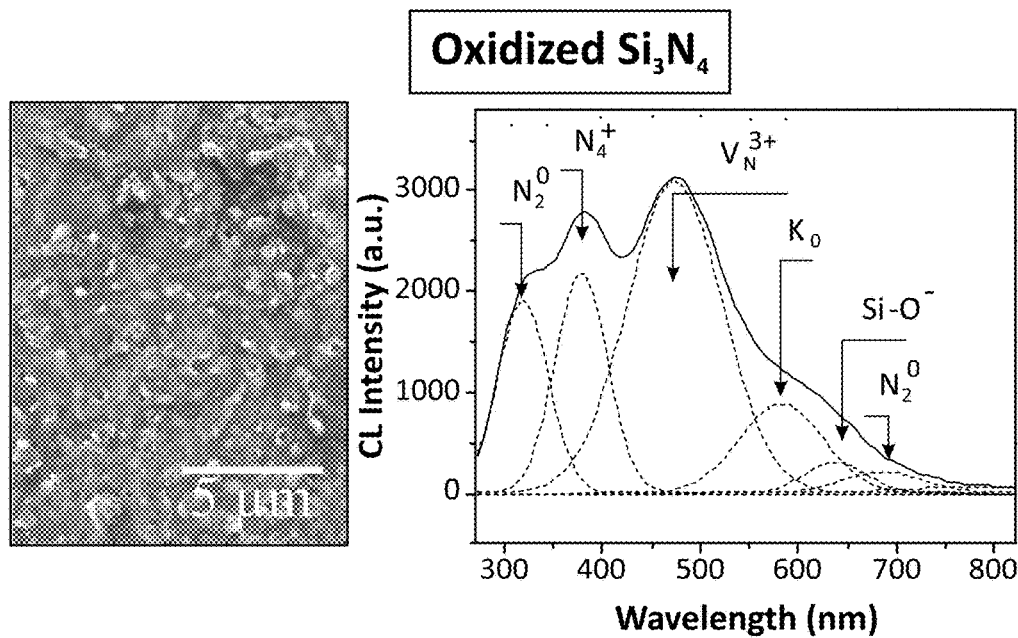
FIG. 15 is a graph illustrating the results of a cathodoluminescence spectroscopy analysis for a silicon nitride material oxidized using the methods and principles disclosed herein.

FIG. 15 is a graph illustrating the results of a cathodoluminescence spectroscopy analysis for a silicon nitride material oxidized using the methods and principles disclosed herein. As seen in the figure, the population of positively charged nitrogen vacancies decreases upon annealing in the presence of oxygen. However, this decrease in positively charged defects is partly compensated by an increase in positively charged $N^{4+}$ defects.

Figure 16:
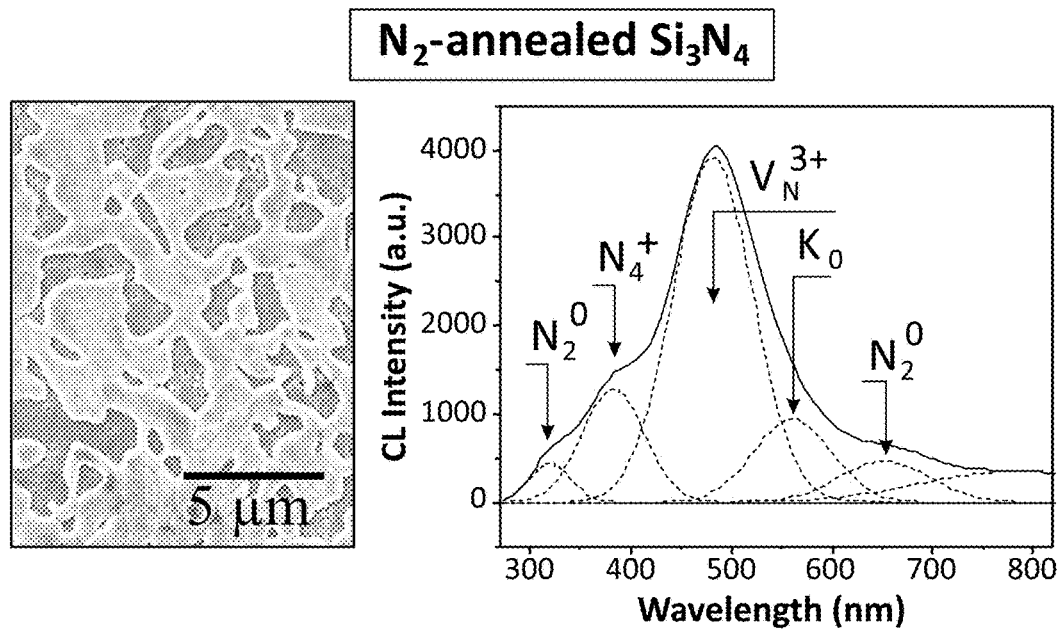
FIG. 16 is a graph illustrating the results of a cathodoluminescence spectroscopy analysis for a silicon nitride material nitrogen annealed using the methods and principles disclosed herein.

FIG. 16 is a graph illustrating the results of a cathodoluminescence spectroscopy analysis for a silicon nitride material nitrogen annealed using the methods and principles disclosed herein. In this figure, we discovered a significant increase in positively charged nitrogen vacancy population upon nitrogen annealing. This appears to be counterintuitive if one considers the availability of nitrogen at high temperature and the number of (pre-existing) vacancies expected to annihilate during the annealing process. In other words, one should expect a decrease rather than an increase in nitrogen vacancy concentration upon nitrogen annealing with respect to the as-fired sample. The conundrum may be clarified by conceiving the formation of a new oxynitride phase (also including Y and Al elements) at the surface of the material, as can also be seen in the scanning electron micrograph on the left side of FIG. 16.

Figure 17:
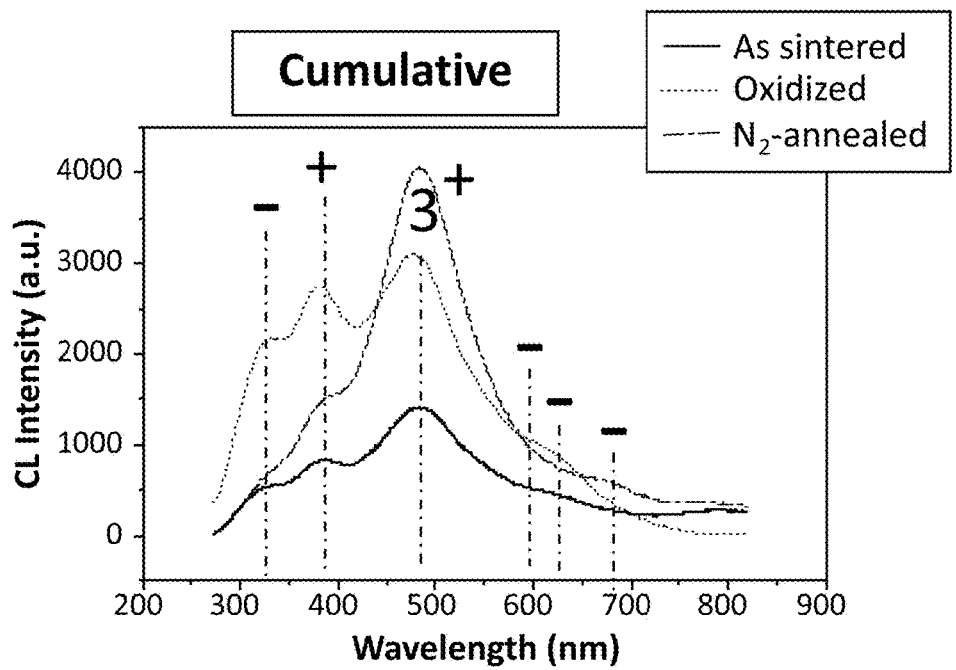
FIG. 17 is a graph illustrating the cumulative results of the cathodoluminescence spectroscopy analyses the results of which are depicted in FIGS. 14-16.

FIG. 17 is a graph illustrating the cumulative results of the cathodoluminescence spectroscopy analyses the results of which are depicted in FIGS. 14-16. In FIG. 17, defects are simply labeled by means of the + or − charges.

Figure 18:
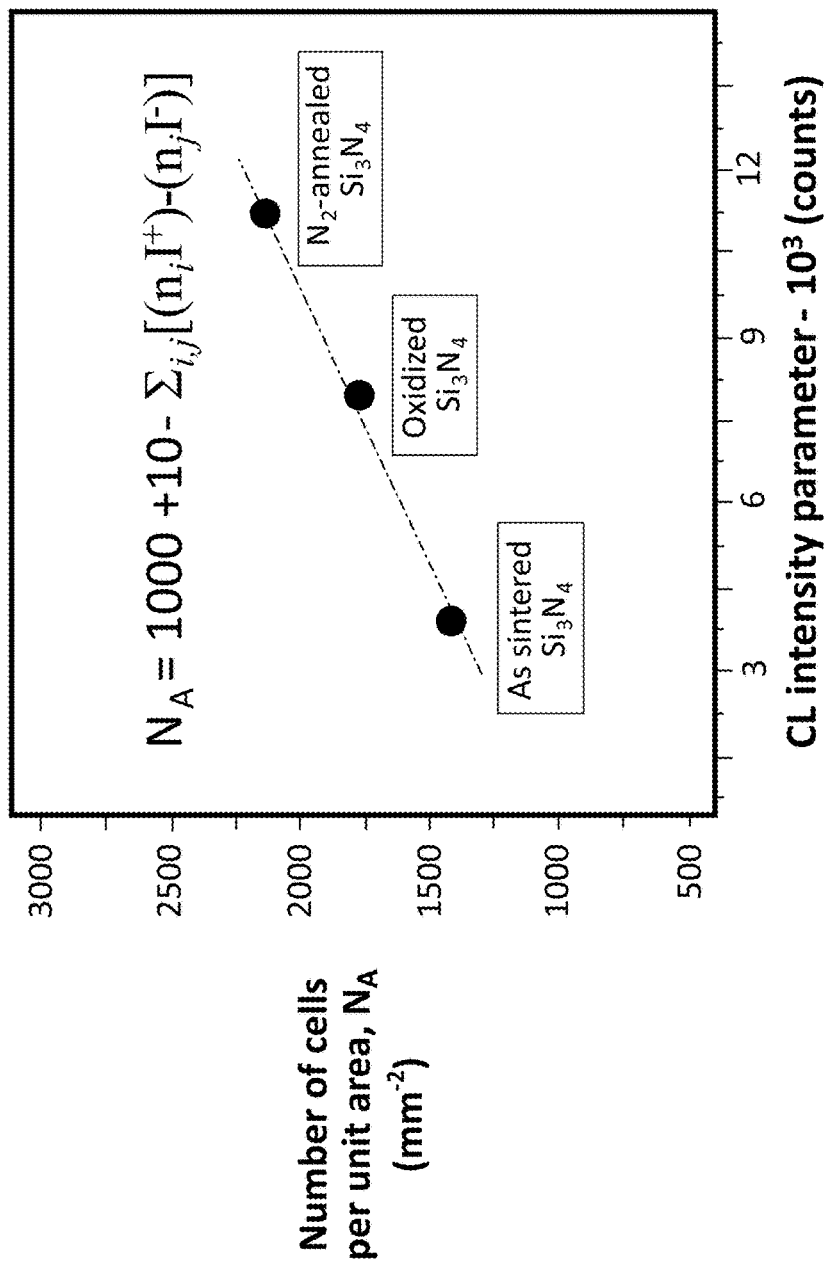
FIG. 18 is a graph illustrating the relationship between a cathodoluminescence spectroscopy intensity parameter and cell proliferation for various materials, some of which were treated in accordance with methods and principles disclosed herein.

FIG. 18 is a graph illustrating the relationship between the so-called cathodoluminescence intensity parameter, $\Sigma_{ij}[(n_i I^+)-(n_j I^-)]$, and cell proliferation measured in number of cells per unit area ($N_A/mm^2$) for various materials, some of which were treated in accordance with methods and principles disclosed herein. The above-mentioned cathodoluminescence intensity parameter simply represents the algebraic summation of the cathodoluminescence intensity of subbands produced by positively ($I^+$) and negatively ($I^-$) charged defects multiplied by their respective charge valence ($n_i$ and $n_j$ for positively and negatively charged defects, respectively). The cathodoluminescence intensity parameter is considered here to represent the surface charge of the sample. Thus, this graph suggests the presence of a direct, empirical relationship between cell proliferation and a cathodoluminescence spectroscopy intensity parameter, which may be characterized by the following equation:

$$N_A = 1000 + 10 \times \Sigma_{ij}[(n_i I^+)-(n_j I^-)]$$

Although there could be additional types of charged defects at the surface of the silicon nitride samples that actually do not luminesce (i.e., are invisible to the cathodoluminescence analysis), the simple equation obtained above shows that there is a relationship between surface or near-surface charge and hydroxyapatite formation. In this context, the higher the positive charge of the surface, the better its osteoconductivity. The equation points to the efficacy of increasing nitrogen vacancies (and other positively charged defects) at the sample surface for maximizing the speed of hydroxyapatite formation on the material surface.

Example 6

In this example, as-fired silicon nitride samples were prepared as specified in Example 4 above as discs of about 1 mm in thickness and about 12.7 mm in diameter. Additionally, an aqueous glazing slurry was prepared. The ceramic powder constituents of the slurry were yttrium oxide, silicon dioxide, aluminum nitride, aluminum oxide, and silicon nitride, by weight with respect to total solids of about 58.89%, 27.31%, 6.11%, 4.56%, and 3.14%, respectively. This mixture was suspended in water at a concentration of 1.41% by weight. The slurry was ball milled overnight using silicon nitride media (about 6 mm in diameter) in order to break up soft agglomerates and facilitate constituent mixing. Following milling, silicon nitride samples were dipped into the resulting slurry, removed, and allowed to dry. Once the samples were dry, they were subjected to a heat treatment of about 1400° C. for 30 minutes in a nitrogen atmosphere at a pressure of about 1-2 pounds per squareinch.

Figure 19A:
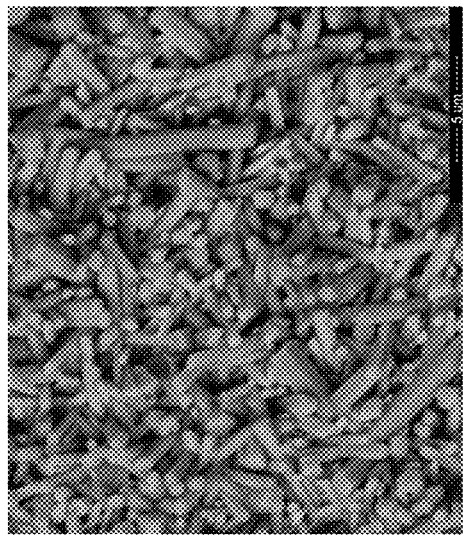
FIGS. 19a-19f are photographs illustrating various details of certain materials produced in accordance with methods disclosed herein.
Figure 19B:
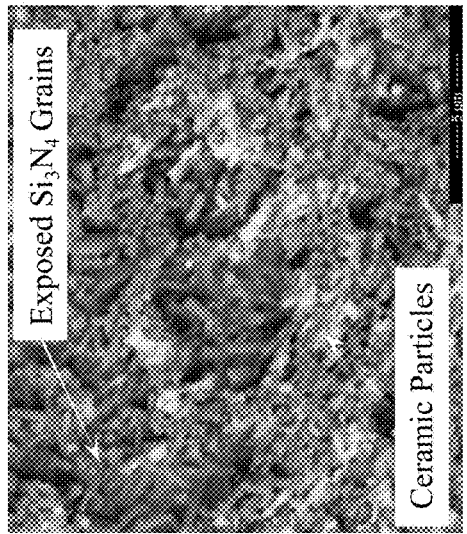
Figure 19C:
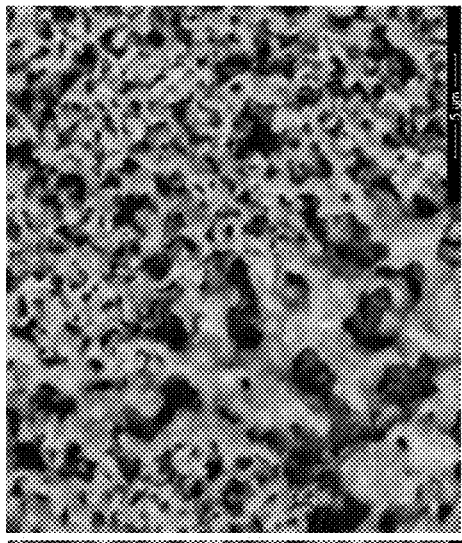

Back-scattered electron micrographs of the resulting surface microstructures are shown in FIG. 19A in the untreated state, in FIG. 19B following slurry dipping and drying but prior to the heat treatment, and in FIG. 19C following the heat treatment. It is clear from these images that the ceramic particles deposited by the slurry have reacted to form a new, relatively high atomic weight phase on the silicon nitride surface.

Water contact angle measurements via the sessile drop technique, made using an optical comparator with goniometer functionality and 20 μL deionized water droplets, on the SiYAlON-glazed surface yielded a value of 28.29±14.32° (6 specimens, 2 measurements each), showing a dramatic increase in hydrophilicity relative to the untreated silicon nitride's exhibited average water contact angle of 66°.

FIG. 20c shows the x-ray diffraction pattern obtained for the SiYAlON-glazed surface relative to the untreated control shown in FIG. 20a. In addition to the β-$Si_3N_4$ peaks common with the control (labeled as 13), the SiYAlON-glazed sample also exhibited multiple peaks consistent with the standard pattern for N-apatite ($Y_5Si_3O_{12}N$, JCPDS 48-1625, labeled as A) and a few peaks common with standards for cristobalite ($SiO_2$, JCPDS, labeled as C) and yttrium aluminum garnet (YAG, $Y_3Al_5O_{12}$, JCPDS, labeled as Y), indicating that the majority of the glaze constituents reacted to form N-apatite while a minority remainder either reacted to form YAG or cristobalite. The presence of these various phases may contribute to improved osteoconductivity and bacteriostasis.

FIG. 20b shows the x-ray diffraction pattern obtained for the nitrogen-annealed silicon nitride relative to the untreated control shown in FIG. 20a. Similarly, FIG. 20d shows the x-ray diffraction pattern obtained for SiYON-Ap-glazed surface relative to the untreated control and FIG. 20e shows the x-ray diffraction pattern obtained for the SiYAlON monolith. These materials and their preparation will be discussed in greater detail in connection with other examples below.

FIG. 21 shows the surface atomic composition, as measured by x-ray photoelectron spectroscopy (XPS), of untreated silicon nitride, silicon nitride annealed in nitrogen at about 1400° C. for 30 minutes, and SiYAlON-glazed silicon nitride, respectively. The data shows SiYAlON glass phase associated with nitrogen annealing. As illustrated by this data, a significant increase in surface Y and Al relative to both the untreated and nitrogen annealed silicon nitride samples, is observed in the SiYAlON glazed sample. This is indicative of a relatively high degree of surface coverage for the SIYAlON glaze material.

Osteosarcoma cells from the Saos-2 cell line were cultured in an osteogenic medium consisting of DMEM (D-glucose, L-Glutamine, Phenol red, and Sodium Pyruvate) with 10% fetal bovine serum and allowed to incubate for about 24 hours at 37° C. resulting in a final Saos-2 concentration of 5×105 cells/mL. Cultured cells were seeded onto sample surfaces, which were previously subjected to UV sterilization, in an osteogenic medium consisting of DMEM supplemented with 50 μg/mL ascorbic acid, 10 mM β-glycerol phosphate, 100 mM hydrocortisone, and about 10% fetal bovine calf serum. The seeded samples were incubated for 7 days at about 37° C., and the medium was refreshed twice during that period.

Figures 22A, 22B:
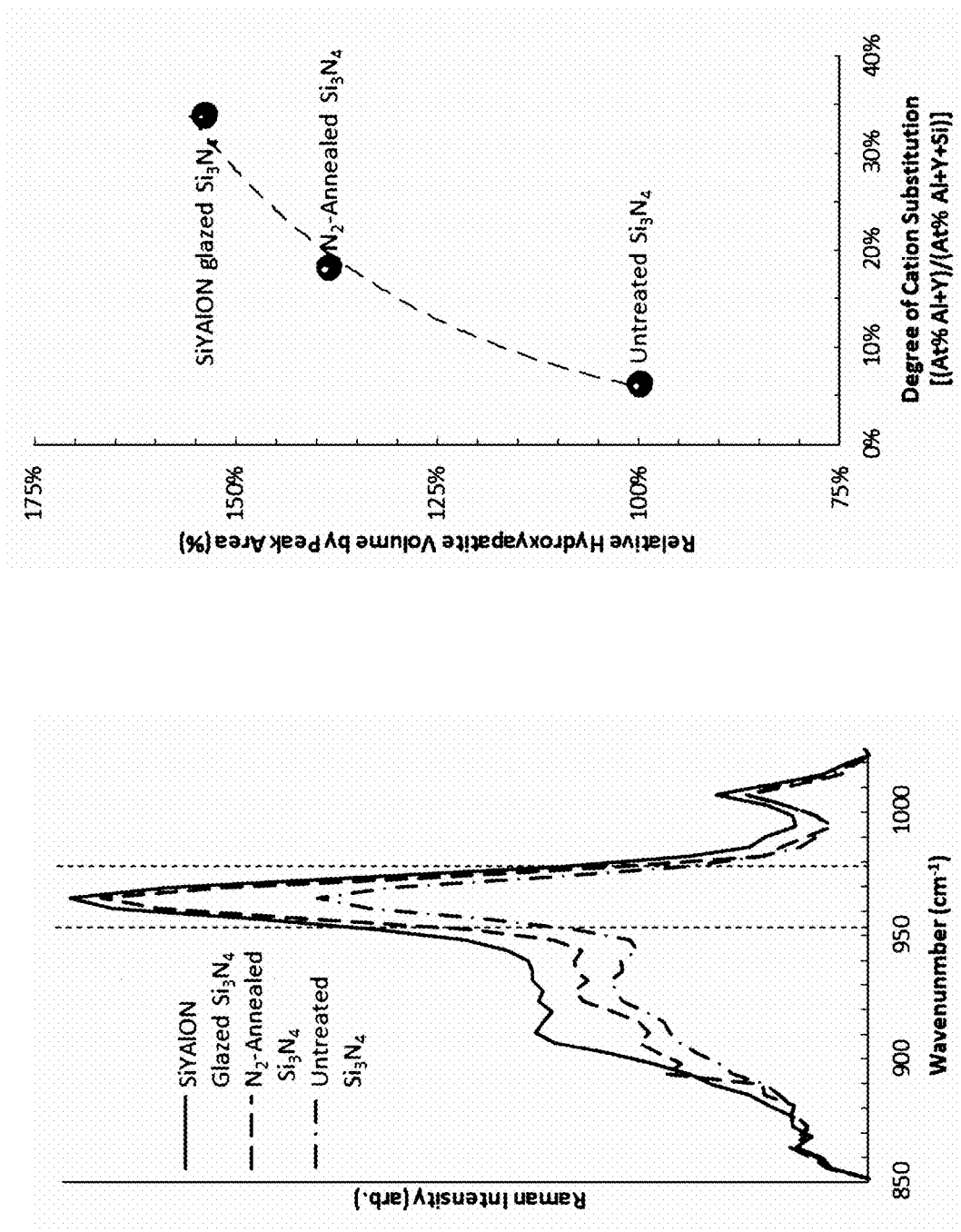
FIG. 22a is a graph illustrating the Raman intensities by wavenumber for various materials produced in accordance with methods disclosed herein compared to an untreated sample.
FIG. 22b is a graph depicting the peak area obtained for each sample, normalized by the peak area for the untreated sample, charted as a function of atomic percent Al+Y, normalized by atomic percent Al+Y+Si at the surface, as measured by XPS.

Immediately following the incubation period, Raman image maps were generated with a Laser Raman Microscope (RAMANtouch™ by Nanophoton™, Osaka, Japan) using a 20× immersion-type objective and a 532 nm-wavelength laser source. Each pixel measures 1.02×1.02 μm, and each image is composed of 171 horizontal rows of 400 pixels. The spectra for each pixel in the respective Raman maps (68,400 spectra each) were averaged, and comparisons of the averaged Raman peaks at 965±12.5 cm$^{-1}$, associated with P—O stretching within $PO_4^{-3}$ tetrahedra, and the area of which is proportional to deposited hydroxyapatite volume, are charted in FIG. 22a. In FIG. 22b, the peak area obtained for each sample, normalized by the peak area for the untreated sample, is charted as a function of atomic percent Al+Y, normalized by atomic percent Al+Y+Si at the surface, as measured by XPS. This normalized atomic percent of Al+Y represents the degree to which SIYAlON has displaced $Si_3N_4$ at the surface, yielding a rough estimate of SiYAlON coverage for the x-axis of the chart. This plot illustrates the observed trend of increasing hydroxyapatite mineralization as a function of surface SiYAlON concentration among the samples.

Example 7

In this example, an aqueous slurry was prepared as outlined above in connection with Example 5. The ceramic powder constituents of the slurry were yttrium oxide, silicon dioxide, aluminum nitride, aluminum oxide, and silicon nitride, by weight with respect to total solids of about 58.89%, 27.31%, 6.11%, 4.56%, and 3.14%, respectively. This mixture was suspended in water at a concentration of 28% by weight. The slurry was ball milled overnight using silicon nitride media (6 mm diameter) in order to break up soft agglomerates and facilitate constituent mixing. The milled slurry was dried in an oven at about 80° C. Following drying, the resulting cake was ground using a mortar and pestle in order to remix constituents that may have been subjected to differential settling and to break up some of the agglomerates that formed during drying. This mixture was then placed into a silicon nitride vessel and subjected to a heat treatment of about 1600° C. for about 30 minutes.

Although it is conceivable that some embodiments and implementations may utilize other vessels, it has been found that use of other materials in a vessel for the mixture may result in uptake of certain undesired impurities. In addition, it appears that the surface phases of the vessel may play a role in dictating the formation of phases in the glaze and/or glaze monolith via heterogenous nucleation mechanisms. Thus, it may be preferred to contain the mixture in a composition mimicking the makeup of the SiYAlON to some degree, such as silicon nitride.

Figure 19D:
Figure 19E:
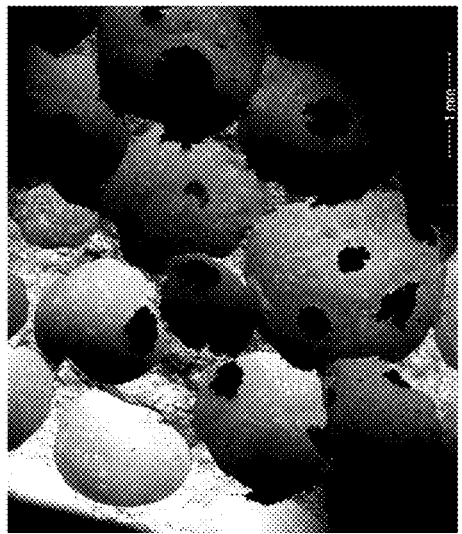
Figure 19F:
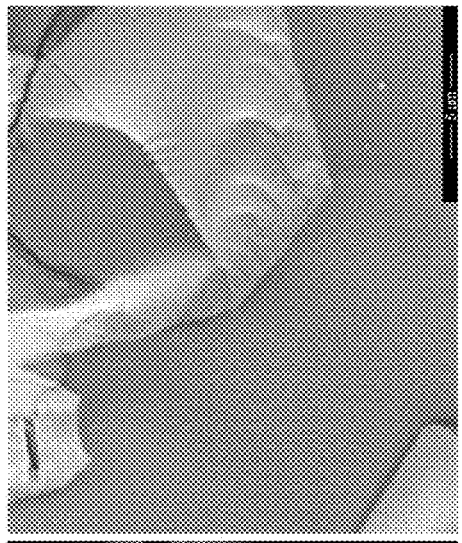

Back-scattered electron micrographs of the resulting material are shown in FIGS. 19e and 19f at low and high magnification, respectively. The low magnification image in FIG. 19e shows the connective pore network that formed within the sample during the heat treatment, and the high magnification image in FIG. 19f shows at least two constituent phases are detected within the sample due to significant atomic number contrast differences.

FIG. 20e shows the complex XRD pattern obtained from a finely-crushed sample of the SiYAlON monolith material. The majority phases identified due to fitting of multiple peaks from their respective standards are monoclinic yttrium silicate ($Y_2SiO_5$, JCPDS 36-1476, labeled as YSM) and hexagonal N-apatite ($Y_5Si_3O_{12}N$, JCPDS 48-1625, labeled as A). Further, the shallow and broad peak between approximately 26° and 37° 2θ is indicative of the presence of amorphous material in addition to the crystalline phases. This is consistent with the material exhibiting optical translucency. This example demonstrates that monoliths made using the same composition as the SiYAlON glaze from Example 5 can be cast with connective porosity for potential use as tissue scaffolds. These monoliths can also be crushed and ground in order to be used as fill material.

Similarly, FIG. 20b indicates the presence of yttrium disilicate ($Y_2Si_2O_7$, JCPDS 72-3599, labeled as YS2M) along with the hexagonal N-apatite ($Y_5Si_3O_{12}N$, JCPDS 48-1625, labeled as A) and $\beta$-$Si_3N_4$.

Example 8

In this example, as-fired silicon nitride samples were prepared as specified in Example 4 as discs of about 1 mm in thickness and about 12.7 mm in diameter. Additionally, an aqueous glazing slurry was prepared as outlined above in Example 5. The ceramic powder constituents of the slurry were yttrium oxide, silicon dioxide, and silicon nitride, by weight with respect to total solids of about 76.83%, 18.40%, and 4.77%, respectively. This mixture corresponds stoichiometrically to the molecular formula for N-apatite, $Y_5Si_3O_{12}N$. The powder mixture was suspended in water at a concentration of 4.08% by weight. The resulting slurry was ball milled overnight using silicon nitride media (6 mm diameter) in order to break up soft agglomerates and facilitate constituent mixing. Silicon nitride samples were dipped into the milled slurry, removed, and allowed to dry. Once the samples were dry, they were subjected to a heat treatment of about 1500° C. for about 30 minutes in a nitrogen atmosphere at a pressure of 1-2 pounds per square-inch.

A back-scattered electron micrograph of the resulting surface is shown in FIG. 19d. It is clear from this photograph that the particulate constituents reacted and formed a new phase that coated the underlying silicon nitride grains. The glaze formed in this example appears to be thinner and better conforming to the substrate morphology than the SiYAlON glaze produced in Example 5.

Contact angle goniometry, using an optical comparator and 20 μL deionized water droplets, yielded a static contact angle of 7.01±0.60° (5 specimens, 2 measurements each), a superhydrophilic surface, for this condition.

FIG. 20d shows the x-ray diffraction pattern obtained for the SiYON-apatite glaze surface relative to the untreated control represented by FIG. 20a. In addition to the $\beta$-$Si_3N_4$ peaks common with the control (labeled as $\beta$), the primary phase identified within the glaze, due to fitting of multiple peaks, is hexagonal N-apatite ($Y_5Si_3O_{12}N$, JCPDS 48-1625, labeled as A). This phase appears to make up the bulk of the glaze composition. This example demonstrates that specific targeted phases can be made to comprise the majority of the glaze on the silicon nitride surface.

As mentioned above, the processes and/or novel materials described herein may be used to, for example, change the surface chemistry of silicon nitride or other ceramics by forming a polycrystalline or glass coating consisting of high-nitrogen content SiYAlON or SiYON, as mentioned above. Alternatively, the SiYAlON/SiYON glass itself may be formulated and prepared separate from the silicon nitride and used as a filler, coating, or otherwise incorporated into other implants or materials.

In yet other embodiments, the processes and/or novel materials described herein may comprise other glassy and/or amorphous oxynitrides containing silicon along with yttrium and/or aluminum, such as SiAlONs. Thus, one or more of the specific references to SiYAlON/SiYONs disclosed herein, may, depending upon the desired application, comprise use of SiAlONs instead.

To provide another specific example, a coating of treated silicon nitride, SiYAlON/SiYON, and/or another synthetic apatite (e.g., $Y_5(SiO_4)_3N$) via any number of methods, such as, for example, biomimetic, thermal spraying, PVD, or CVD, may be applied to hip stems to enhance their osteointegration more so than the hydroxyapatite coatings that are currently used. These same methods and/or materials could be used to apply coatings to any other metallic material, such as screws, pins, plates, rods, dental posts, etc.

Still another specific example is bone void fillers. The silicon oxynitride compounds disclosed herein could be mixed with any reasonable biocompatible polymeric material or cement (either resorbable or non-resorbable) to aid in the osteointegration of bone defects. Potential polymers could include, for example, polymethylmethacrylate, cyanoacrylates, polyethylene, polyurethane, polyetheretherketone (PEEK), polylatic acid, poly(L, DL-lactide) and poly (L-lactide-co-glycolide), Poly(lactic-co-glycolic acid, and polycaprolactone, fibrin, or gelatin based systems, and inorganic cements based on calcium/magnesium phosphates or the like. Even mixtures of the silicon oxynitride compounds with hydroxyapatite or bioglass may be used for certain applications.

It should be further understood that certain preferred embodiments of the materials disclosed herein comprise both amorphous and crystalline phases. In some cases, a plurality of different crystalline phases, alone with one or more amorphous phases, may be provided. For instance, these crystalline phases could be comprised of $Y_5Si_3O_{12}N$ (N-apatite), $Y_2SiO_5$ (yttrium silicate) $Y_2Si_2O_7$ (yttrium disilicate), a range of nitrogen doped yittrium silicates such as $Y_4Si_2O_7N_4$, $YSiO_2N$, $Y_2Si_3O_3N_4$, and/or other similar compounds including $Y_2SiAlO_5N$, $Y_3AlSi_2O_2N_7$, $Y_4Al_2O_9$, $Y_3Al_5O_{12}$, and $Al_6Si_6O_9N_8$.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A silicon oxynitride material having osteoconductive properties, comprising:
   a first crystalline phase, wherein the first crystalline phase comprises monoclinic yttrium silicate;
   a second crystalline phase, wherein the second crystalline phase comprises hexagonal N-apatite; and
   a first amorphous phase, wherein the silicon oxynitride material has osteoconductive properties.

2. The material of claim 1, wherein the silicon oxynitride material comprises a surface glaze, and wherein the surface glaze comprises the first amorphous phase.

3. The material of claim 1, wherein the first amorphous phase comprises at least one of silicon yttrium aluminum oxynitride (SiYAlON), silicon yttrium oxynitride (SiYON), and silicon aluminum oxynitride (SiAlON).

4. The material of claim 1, wherein the first crystalline phase comprises at least one of silicon yttrium aluminum oxynitride (SiYAlON), silicon yttrium oxynitride (SiYON), and silicon aluminum oxynitride (SIAlON).

* * * * *